United States Patent
Chen et al.

(10) Patent No.: US 9,109,040 B2
(45) Date of Patent: Aug. 18, 2015

(54) TREATMENT AND PREVENTION OF MALARIA

(75) Inventors: Lin Chen, Melbourne (AU); Alan Cowman, Melbourne (AU); Tony Triglia, Melbourne (AU)

(73) Assignee: The Walter and Eliza Hall Institute of Medical Research, Parkville, Victoria (AU)

( * ) Notice: Subject to any disclaimer, the term of this patent is extended or adjusted under 35 U.S.C. 154(b) by 0 days.

(21) Appl. No.: 13/884,604

(22) PCT Filed: Nov. 8, 2011

(86) PCT No.: PCT/AU2011/001442
§ 371 (c)(1),
(2), (4) Date: Jul. 23, 2013

(87) PCT Pub. No.: WO2012/061882
PCT Pub. Date: May 18, 2012

(65) Prior Publication Data
US 2014/0010816 A1    Jan. 9, 2014

Related U.S. Application Data

(60) Provisional application No. 61/411,598, filed on Nov. 9, 2010, provisional application No. 61/435,602, filed on Jan. 24, 2011.

(51) Int. Cl.
*C07K 14/445* (2006.01)
*G01N 33/569* (2006.01)
*A61K 39/015* (2006.01)
*A61K 39/00* (2006.01)

(52) U.S. Cl.
CPC .......... *C07K 14/445* (2013.01); *A61K 39/015* (2013.01); *G01N 33/56905* (2013.01); *A61K 2039/505* (2013.01); *G01N 2333/445* (2013.01); *G01N 2500/02* (2013.01)

(58) Field of Classification Search
None
See application file for complete search history.

(56) References Cited

U.S. PATENT DOCUMENTS

| | | | |
|---|---|---|---|
| 8,703,147 B2 | 4/2014 | Cowman et al. | |
| 2009/0175895 A1* | 7/2009 | Cowman et al. | 424/191.1 |
| 2009/0202579 A1 | 8/2009 | Cowman et al. | |
| 2011/0311571 A1 | 12/2011 | Cowman et al. | |

OTHER PUBLICATIONS

Bowman et al. (Nature vol. 400, pp. 532-538, 1999).*
Breman, et al., Am J Trop Med Hyg, "Conquering the Intolerable Burden of Malaria: What's New, What's Needed: A Summary," 2004; 71(Suppl 2): 1-15.
Duraisingh, et al., The EMBO Journal, "Phenotypic variation of *Plasmodium falciparum* merozoite proteins directs receptor targeting for invastion of human erythrocytes," 2003; 22: 1047-1057.
George, et al., Protein Engineering, "An analysis of protein domain linkers: their classification and role in protein folding," 2003; 15: 871-879.
Harayama, Trends Biotech, "Artificial evolution by DNA shuffling," 1998; 16: 76-82.
Hay, et al., Lancet Infect Dis, "The global distribution and population at risk of malaria: past, present, and future," 2004; 4: 327-336.
Hoffmann, et al., J Infect Dis, "Protection of Humans against Malaria by Immunization with Radiated-Attenuated *Plasmodium falciparum* Sporozoites," 2002; 185: 1155-1164.
Needleman, et al., J Mol Biol, "A General Method Applicable to the Search for Similarities in the Amino Acid Sequence of Two Proteins," 1970; 48: 443-453.
Ohta, et al., Tokai J Exp Clin Med, "Screening of HLA-DR-Restricted Helper T-cell Epitopes of MSP1 of *Plasmodium falciparum* in Humans," 1998; 23: 85.
Paolicelli, et al., Nanomedicine, "Surface-modified PLGA-based nanoparticles that can efficiently associate and deliver virus-like particles," 2010; 5: 843-853.
Rammensee, Curr Opin Immunol, " Chemistry of peptides associated with MHC class I and class II molecules," 1995; 7: 85-96.
Singh, et al., PLoS One, "Helper T Cell Epitope-Mapping Reveals MHC-Peptide Binding Affinities that Correlate with T Helper Cell Responses to Pneumococcal Surface Protein A," 2010; 5: 39435.
Snow, et al., Am J Trop Med Hyg, "Pediatric Mortality in Africa: *Plasmodium falciparum* Malaria as a Cause or Risk?" 2004; 71(Suppl 2): 16-24.
Sun, et al., Vaccine, "Advances in saponin-based adjuvants," 2009; 27: 1787-1796.
Wang, et al., PNAS USA, "Induction of CDR+ T cell-dependent CD8+ type 1 responses in humans by a malaria DNA vaccine," 2001; 98: 10817-10822.
GenBank Accession No. CAB39049 & XM_001351269, Conserved *Plasmodium* protein, unknown function [*Plasmodium falciparum* 3D7].
Chen et al., "An EGF-like protein forms a complex with PfRh5 and is required for invasion of human erythrocytes by *Plasmodium falciparum*", PLOS Pathogens, 2011, 7:e1002199.
Healer et al., "Vaccination with conserved regions of erythrocyte-binding antigens induces neutralizing antibodies against multiple strains of *Plasmodium falciparum*", PLOS One, 2013, 8:e72504.
Reed et al., "Targeted disruption of an erythrocyte binding antigen in *Plasmodium falciparum* is associated with a switch toward a sialic acid-independent pathway of invasion", Proc National Acad Sci, 2000, 97:7509-7514.

* cited by examiner

*Primary Examiner* — Gary Nickol
*Assistant Examiner* — Khatol Shahnan Shah
(74) *Attorney, Agent, or Firm* — Klauber & Jackson LLC

(57) ABSTRACT

The present invention relates to polypeptides from *Plasmodium* and polynucleotides encoding the polypeptides. The invention further relates to compositions comprising the polypeptides and their use in the treatment and prevention of malaria.

10 Claims, 12 Drawing Sheets

A

B

TREATMENT AND PREVENTION OF MALARIA

CROSS REFERENCE TO RELATED APPLICATIONS

The present application is a National Stage Application claiming the priority of PCT Application No. PCT/AU2011/001442 filed Nov. 8, 2011, which in turn, claims priority from U.S. Provisional Application Ser. No. 61/411,598, filed Nov. 9, 2010, and U.S. Provisional Application Ser. No. 61/435,602, filed Jan. 24, 2011. Applicants claim the benefits of 35 U.S.C. §120 as to the PCT application and priority under 35 U.S.C. §119 as to the said U.S. provisional applications, and the entire disclosures of all applications are incorporated herein by reference in their entireties.

FIELD OF THE INVENTION

The present invention relates to polypeptides from *Plasmodium* and polynucleotides encoding the polypeptides. The invention further relates to compositions comprising the polypeptides and their use in the treatment and prevention of malaria.

BACKGROUND OF THE INVENTION

Human malaria is caused by infection with protozoan parasites of the genus *Plasmodium*. Four species are known to cause human disease: *Plasmodium falciparum, Plasmodium malariae, Plasmodium ovale* and *Plasmodium vivax*. However, *Plasmodium falciparum* is responsible for the majority of severe disease and death. Recent estimates of the annual number of clinical malaria cases worldwide range from 214 to 397 million (The world health report 2002: reducing risks, promoting healthy life. Geneva: World Health Organization; Breman et al., 2004), although a higher estimate of 515 million (range 300 to 660 million) clinical cases of *Plasmodium falciparum* in 2002 has been proposed (Snow et al., 2004). Annual mortality (nearly all from *Plasmodium falciparum* malaria) is thought to be around 1.1 million (Breman et al., 2004).

Malaria also significantly increases the risk of childhood death from other causes (Snow et al., 2004). Almost half of the world's population lives in areas where they are exposed to risk of malaria (Hay et al., 2004), and the increasing numbers of visitors to endemic areas are also at risk. Despite continued efforts to control malaria, it remains a major health problem in many regions of the world, and new ways to prevent and/or treat the disease are urgently needed.

Early optimism for vaccines based on malarial proteins (so called subunit vaccines) has been tempered over the last two decades as the problems caused by allelic polymorphism and antigenic variation, original antigenic sin, and the difficulty of generating high levels of durable immunity emerged, and with the notable failures of many promising subunit vaccines (such as SPf66) have led to calls for a change in approach towards a malaria vaccine. Consequently, this growing sense of frustration has lead to the pursuit of different approaches that focus on attenuated strains of malaria parasite or irradiated *Plasmodium falciparum* sporozoites (Hoffmann et al., 2002). Similarly, both the limited success achieved to date with protein-based vaccines and the recognition that cell mediated immunity may be critical to protection against hepatic and perhaps blood stages of the parasite has led to a push for DNA and vectored vaccines, which generate relatively strong cell mediated immunity. Unfortunately, DNA vaccines have demonstrated poor efficacy in humans with respect to antibody induction (Wang et al., 2001). Thus, there remains a need for methods of treating and preventing malaria.

SUMMARY OF THE INVENTION

The present inventors have identified a novel polypeptide from *Plasmodium* that is involved in the invasion of host cells. The present inventors have found that antibodies to these polypeptide inhibit merozoite binding and invasion of erythrocytes.

Accordingly, in one aspect, the present invention provides a composition comprising an isolated and/or recombinant polypeptide (referred to herein as a Rip polypeptide), wherein the polypeptide comprises or consists of:
  i) an amino acid sequence selected from any one of SEQ ID NOs:2 to 4,
  ii) an amino acid sequence which is at least 70% identical to any one or more of SEQ ID NOs:2 to 4, and/or
  iii) an antigenic fragment of 1) or ii).

In one embodiment, the polypeptide comprises or consists of an amino acid sequence which is at least 90% identical to any one or more of SEQ ID NOs:2 to 4, or an antigenic fragment thereof.

In a particularly preferred embodiment, the antigenic fragment comprises, more preferably or consists of, the amino acid sequence as set forth in SEQ ID NO:3, or an amino acid sequence at least 70% identical to SEQ ID NO:3.

In another preferred embodiment, the composition further comprises an Rh polypeptide or antigenic fragment thereof. Examples of Rh polypeptides include, but are not necessarily limited to, Rh1, Rh2a, Rh2b, Rh4 and Rh5.

In one particular embodiment, the Rh polypeptide, or antigenic fragment, comprises or consists of:
  i) an amino acid sequence selected from any one of SEQ ID NOs:10 to 28,
  ii) an amino acid sequence which is at least 70% identical to any one or more of SEQ ID NOs:10 to 28, and/or
  iii) an antigenic fragment of i) or ii).

In one embodiment, the composition comprises an Rh1 polypeptide or antigenic fragment thereof which comprises or consist of:
  i) an amino acid sequence as set forth in SEQ ID NO:10,
  ii) an amino acid sequence which is at least 70% identical to SEQ ID NO:10, and/or
  iii) an antigenic fragment of i) or ii).

In another embodiment, the composition comprises an Rh2 polypeptide or antigenic fragment thereof which comprises or consists of:
  i) an amino acid sequence selected from any one of SEQ ID NOs:11 to 14,
  ii) an amino acid sequence which is at least 70% identical to any one or more of SEQ ID NOs:11 to 14, and/or
  iii) an antigenic fragment of i) or ii).

In a preferred embodiment, the Rh2 antigenic fragment comprises, more preferably or consists of:
  i) the amino acid sequence as set forth in SEQ ID NO:12, or an amino acid sequence at least 70% identical to SEQ ID NO:12, or
  ii) the amino acid sequence as set forth in SEQ ID NO:13, or an amino acid sequence at least 70% identical to SEQ ID NO:13. Even more preferably, the Rh2 antigenic fragment comprises, more preferably or consists of:
  i) the amino acid sequence as set forth in SEQ ID NO:12, or an amino acid sequence at least 70% identical to SEQ ID NO:12.

In a further embodiment, the composition comprises an Rh4 polypeptide or antigenic fragment thereof which comprises or consists of:
  i) an amino acid sequence as set forth in SEQ ID NO:15 or SEQ ID NO:16,
  ii) an amino acid sequence which is at least 70% identical to SEQ ID NO: 15 and/or SEQ ID NO:16, and/or
  iii) an antigenic fragment of i) or ii).

In a preferred embodiment, the Rh4 antigenic fragment comprises, more preferably or consists of, the amino acid sequence as set forth in SEQ ID NO:16, or an amino acid sequence at least 70% identical to SEQ ID NO:16.

In a further embodiment, the composition comprises an Rh5 polypeptide or antigenic fragment thereof which comprises or consists of:
  i) an amino acid sequence selected from any one of SEQ ID NOs:17 to 28,
  ii) an amino acid sequence which is at least 70% identical to any one or more of SEQ ID NOs:17 to 28, and/or
  iii) an antigenic fragment of i) or ii). In a preferred embodiment, the Rh5 antigenic fragment comprises, more preferably or consists of, the amino acid sequence as set forth in SEQ ID NO:18, or an amino acid sequence at least 70% identical to SEQ ID NO:18.

In yet another preferred embodiment, the composition further comprises an EBA polypeptide or antigenic fragment thereof. Examples of EBA polypeptides include, but are not necessarily limited to, EBA175, EBA140 and EBA181. In a preferred embodiment, the EBA polypeptide is EBA175.

In an embodiment, the EBA polypeptide or antigenic fragment comprises or consist of:
  i) an amino acid sequence selected from any one of SEQ ID NOs:35 to 38,
  ii) an amino acid sequence which is at least 70% identical to any one or more of SEQ ID NOs:35 to 38, and/or
  iii) an antigenic fragment of i) or ii).

In one embodiment, the composition comprises an EBA175 polypeptide or antigenic fragment thereof which comprises or consist of:
  i) an amino acid sequence as set forth in SEQ ID NO:35 or SEQ ID NO:36,
  ii) an amino acid sequence which is at least 70% identical to SEQ ID NO:35 and/or SEQ ID NO:36, and/or
  iii) an antigenic fragment of i) or ii).

In a preferred embodiment, the EBA175 antigenic fragment comprises, more preferably or consists of, the amino acid sequence as set forth in SEQ ID NO:36, or an amino acid sequence at least 70% identical to SEQ ID NO:36.

In another preferred embodiment, the composition comprises:
  i) a polypeptide which comprises or consists of an amino acid sequence as set forth in SEQ ID NO:3,
  ii) a polypeptide which comprises or consists of an amino acid sequence as set forth in SEQ ID NO:12; and
  iii) a polypeptide which comprises or consists of an amino acid sequence as set forth in SEQ ID NO:36.

In another embodiment, the composition comprises an EBA181 polypeptide or antigenic fragment thereof which comprises or consist of:
  i) an amino acid sequence as set forth in SEQ ID NO:37,
  ii) an amino acid sequence which is at least 70% identical to SEQ ID NO:37, and/or
  iii) an antigenic fragment of i) or ii).

In another embodiment, the composition comprises an EBA140 polypeptide or antigenic fragment thereof which comprises or consist of:
  i) an amino acid sequence as set forth in SEQ ID NO:38,
  ii) an amino acid sequence which is at least 70% identical to SEQ ID NO:38, and/or
  iii) an antigenic fragment of i) or ii).

In a particularly preferred embodiment, the composition comprises:
  a) a Rip polypeptide or antigenic fragment thereof, namely a polypeptide which comprises or consists of
    i) an amino acid sequence selected from any one of SEQ ID NOs:2 to 4,
    ii) an amino acid sequence which is at least 70% identical to any one or more of SEQ ID NOs:2 to 4, and/or
    iii) an antigenic fragment of i) or ii)
  b) an Rh2 polypeptide or antigenic fragment thereof,
  c) an Rh4 polypeptide or antigenic fragment thereof,
  d) an Rh5 polypeptide or antigenic fragment thereof, and
  e) an EBA175 polypeptide or antigenic fragment thereof.

Preferably, a) comprises, more preferably consists of, the amino acid sequence as set forth in SEQ ID NO:3, or an amino acid sequence at least 70% identical to SEQ ID NO:3.

Preferably, b) comprises, more preferably consists of,
  i) the amino acid sequence as set forth in SEQ ID NO:12, or an amino acid sequence at least 70% identical to SEQ ID NO:12, or
  ii) the amino acid sequence as set forth in SEQ ID NO:13, or an amino acid sequence at least 70% identical to SEQ ID NO:13. More preferably, b) comprises, more preferably consists of, the amino acid sequence as set forth in SEQ ID NO:12, or an amino acid sequence at least 70% identical to SEQ ID NO:12.

Preferably, c) comprises, more preferably consists of, the amino acid sequence as set forth in SEQ ID NO:16, or an amino acid sequence at least 70% identical to SEQ ID NO:16.

Preferably, d) comprises, more preferably consists of, the amino acid sequence as set forth in SEQ ID NO:18, or an amino acid sequence at least 70% identical to SEQ ID NO:18.

Preferably, e) comprises, more preferably consists of, the amino acid sequence as set forth in SEQ ID NO:36, or an amino acid sequence at least 70% identical to SEQ ID NO:36.

A Rip polypeptide may also be referred to as Ripr herein.

The present inventors have also identified a 15 kDa region of the *Plasmodium* proteins pfRh2a and pfRh2b containing the erythrocyte binding domain. Antibodies to this region of pfRh2a/2b inhibit merozoite binding and invasion of erythrocytes.

Thus, in another aspect, the present invention provides a composition comprising an isolated and/or recombinant polypeptide, wherein the polypeptide comprises or consists of:
  i) an amino acid sequence as set forth in SEQ ID NO:12,
  ii) an amino acid sequence which is at least 70% identical to SEQ ID NO:12, and/or
  iii) an antigenic fragment of i) or ii).

In one embodiment, at least one of the polypeptides in a composition of the invention is a fusion protein comprising at least one other polypeptide sequence. The at least one other polypeptide may be, for example, a polypeptide that enhances the stability of a polypeptide of the present invention, or a polypeptide that assists in the purification or detection of the fusion protein, or a polypeptide capable of eliciting an immune response in an animal, especially a human.

In one embodiment, the fusion protein comprises a polypeptide at least 90% identical to MSP-1 (SEQ ID NO:43) or a fragment of at least about 50 amino acids thereof.

In a preferred embodiment, the MSP-1 fragment is MSP-1(42) (SEQ ID NO:44) or MSP-1(19) (SEQ ID NO:45).

In a particularly preferred embodiment, the composition is an immunogenic composition. In one particular embodiment, the composition is a vaccine.

In a particular embodiment, the composition comprises an adjuvant and/or pharmaceutically acceptable carrier.

In another aspect, the present invention provides an isolated and/or recombinant polypeptide, wherein the polypeptide comprises or consists of:
i) an amino acid sequence selected from any one of SEQ ID NOs:2 to 4,
ii) an amino acid sequence which is at least 70% identical to any one or more of SEQ ID NOs:2 to 4, and/or
iii) an antigenic fragment of i) or ii).

In one embodiment, the polypeptide of the above aspect comprises or consists of an amino acid sequence at least 90% identical to any one of SEQ ID NOs:2 to 4 or an antigenic fragment thereof.

In another aspect, the present invention provides an isolated and/or recombinant polypeptide, wherein the polypeptide comprises or consists of:
i) an amino acid sequence as provided in SEQ ID NO:12,
ii) an amino acid sequence which is at least 70% identical to SEQ ID NO:12, and/or
iii) an antigenic fragment of i) or ii).

In one embodiment, the polypeptide of the above aspect comprises or consists of an amino acid sequence at least 90% identical to SEQ ID NO:12 or an antigenic fragment thereof.

In an embodiment, a polypeptide of the invention, or a polypeptide in a composition of the invention, can be purified from a *Plasmodium*, for example *Plasmodium falicparum, Plasmodium vivax, Plasmodium ovale curtisi, Plasmodium ovale wallikeri, Plasmodium malariae,* and/or *Plasmodium knowlesi,* or is an antigenic fragment of the polypeptide. More preferably, *Plasmodium falicparum*.

In another embodiment, a polypeptide of the invention is a fusion protein comprising at least one other polypeptide sequence.

In yet another embodiment, a polypeptide of the invention is immunogenic.

In another aspect, the present invention provides an isolated and/or exogenous polynucleotide comprising or consisting of:
i) a sequence of nucleotides as set forth in any one of SEQ ID NOs:1, 39 or 42,
ii) a sequence of nucleotides encoding a polypeptide of the invention,
iii) a sequence of nucleotides which is at least 70% identical to any one or more of SEQ ID NOs:1, 39 or 42, and/or
iv) a sequence which hybridises with any one or more of i) to iii) under at least moderately stringent conditions.

In one embodiment, the isolated and/or exogenous polynucleotide comprises or consists of:
i) a sequence of nucleotides encoding a polypeptide comprising or consisting of the amino acid sequence set forth in SEQ ID NO:3 and
ii) a sequence of nucleotides encoding a polypeptide comprising or consisting of the amino acid sequence set forth in SEQ ID NO:12.

In yet another embodiment, the isolated and/or exogenous polynucleotide further comprises:
i) a sequence of nucleotides encoding a polypeptide comprising or consisting of the amino acid sequence as set forth in SEQ ID NO:36.

In another aspect, there is provided a vector comprising the isolated and/or exogenous polynucleotide of the invention. In a preferred embodiment, the polynucleotide is operably linked to a promoter.

In another aspect, the present invention provides a DNA vaccine comprising the isolated and/or exogenous polynucleotide of the invention and/or the vector of the invention.

In yet another aspect, the present invention provides a host cell comprising the polypeptide of the invention, the polynucleotide of the invention, and/or the vector of the invention.

In another aspect, the present invention provides a method of making a polypeptide of the invention, the method comprising:
(a) obtaining an expression vector comprising a polynucleotide sequence of the invention operably linked to a promoter; and
(b) introducing said expression vector into a cell or cell free expression system whereby said cell or cell free expression system produces the polypeptide encoded by said polynucleotide sequence.

In one embodiment, the method further comprises isolating said polypeptide.

In another aspect, the present invention provides a substantially purified antibody that specifically binds a polypeptide of the invention.

In one embodiment, the antibody is detectably labelled.

In another aspect, there is provided a method of treating or preventing malaria in a subject, the method comprising administering to the subject a composition of the invention, a polypeptide of the invention, a polynucleotide of the invention, a vector of the invention, a host cell of the invention, and/or an antibody of the invention.

In yet another aspect, there is provided a method for raising an immune response in a subject, the method comprising administering to the subject a composition of the invention, a polypeptide of the invention, a polynucleotide of the invention, a vector of the invention, and/or a host cell of the invention.

In one aspect, the present invention provides use of a composition of the invention, a polypeptide of the invention, a polynucleotide of the invention, a vector of the invention, a host cell of the invention, and/or an antibody of the invention in the manufacture of a medicament for the treatment or prevention of malaria.

In another aspect, the present invention provides a composition of the invention, a polypeptide of the invention, a polynucleotide of the invention, a vector of the invention, a host cell of the invention, and/or an antibody of the invention for use in the treatment or prevention of malaria.

In another aspect, the present invention provides a non-human transgenic organism comprising an exogenous polynucleotide encoding a polypeptide of the invention. In one embodiment, the non-human transgenic organism is a bacterium, for example, *E. coli.*

In another embodiment, the non-human transgenic organism is a plant. Preferably, the plant is selected from a fruit, vegetable or cereal.

In yet another aspect, the present invention provides a method of screening for an agonist or antagonist which modulates the activity of a polypeptide of the invention, the method comprising contacting the polypeptide with a candidate compound, and determining whether said compound binds the polypeptide.

In one embodiment, the antagonist prevents a Rip polypeptide binding an Rh5 polypeptide.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

KEY TO THE SEQUENCE LISTING

Figure 1:
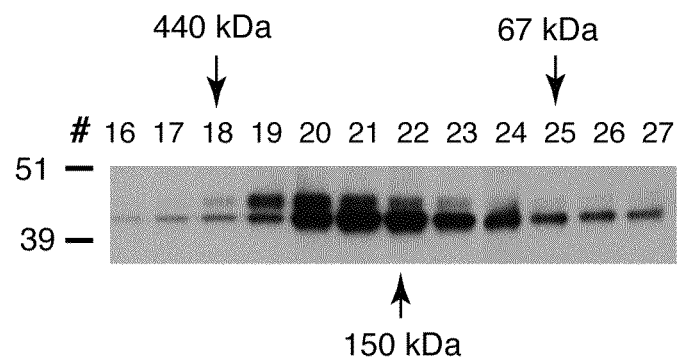
FIG. 1. Characterisation of processed 45 kDa pfRh5 C-terminal domain. (A) Gel-filtration chromatography of purified pfRh5a. Samples collected (# indicates fraction number) were separated by SDS-PAGE. (B) Blue native gel electrophoresis of purified pfRh5.
Figure 1:
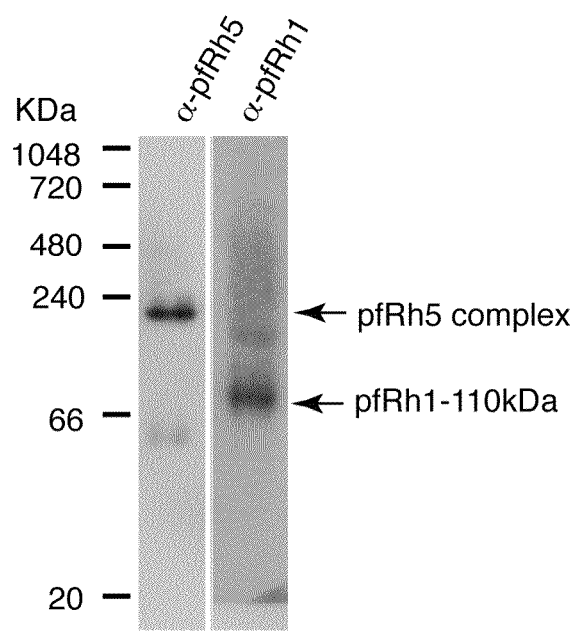
Figure 2:
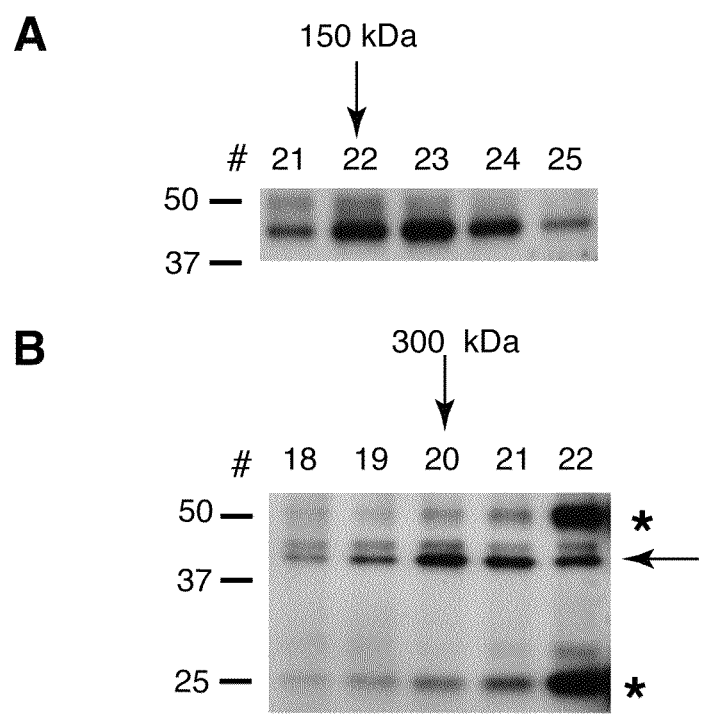
FIG. 2. (A) Gel-filtration chromatography of pfRh5 on a Superdex 200 analytical column. Samples collected (# indicates fraction number) were separated by SDS-PAGE. (B) Gel-filtration chromatography of pfRh5 incubated with pfRh5 antibody on a Superdex 200 column. Samples collected (# indicates fraction number) were separated by SDS-PAGE. * indicates IgG heavy and light chains; Arrow indicates pfRh5.
Figure 3:
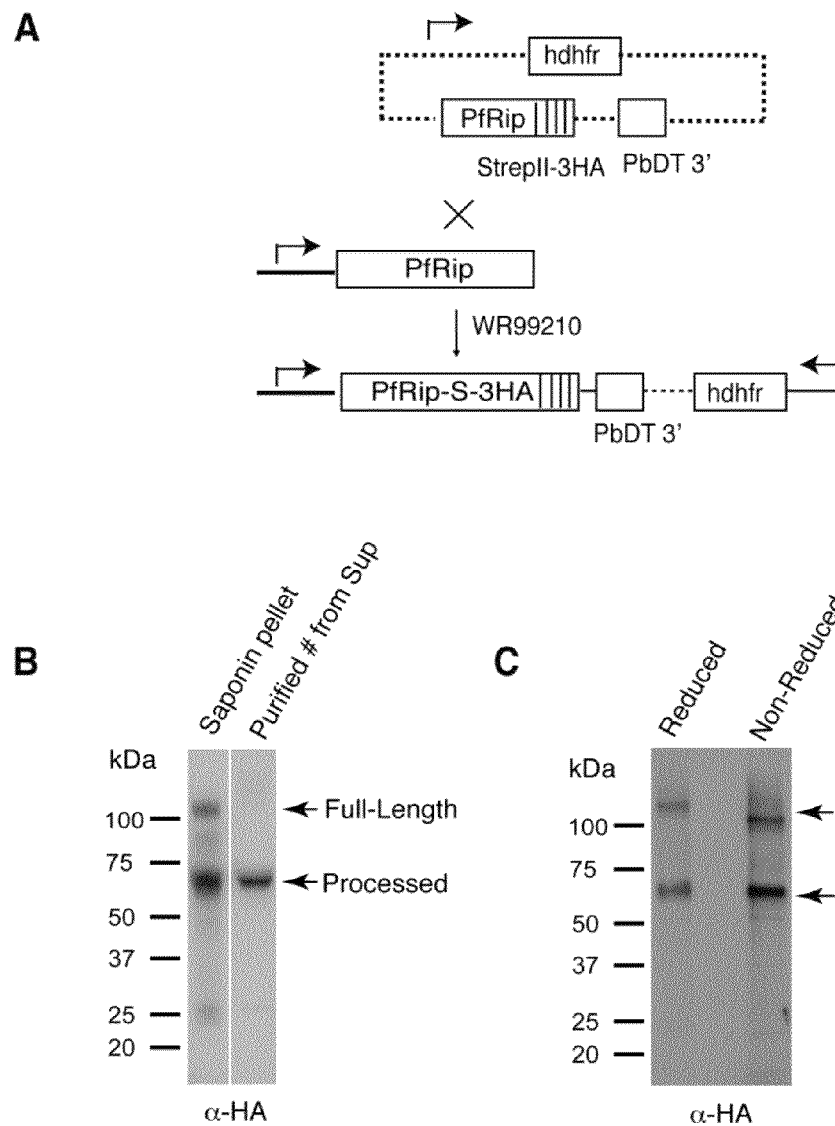
FIG. 3. Generation of C-terminus tagged pfRip parasite line (pfRipHA). (A) Diagram showing that a single Strep-tag and triple Haemaglutinin (HA) tag were added to the C-terminus of pfRip by 3'-single homologous cross-over recombination. (B) Immunoblotting of saponin pellet and HA-tagged protein purified from culture supernatant of pfRipHA line with anti-HA antibody. (C) PfRipHA analysed by SDS-PAGE under reducing and non-reducing conditions.

SEQ ID NO:1—pfRip coding sequence
SEQ ID NO:2—pfRip amino acid sequence
SEQ ID NO:3—pfRip antigenic fragment 791-900
SEQ ID NO:4—pfRip antigenic fragment 238-368
SEQ ID NO:5—pfRip peptide 93-100
SEQ ID NO:6—pfRip peptide 101-114
SEQ ID NO:7—pfRip peptide 699-708
SEQ ID NO:8—pfRip peptide 760-769
SEQ ID NO:9—pfRip peptide 963-972
SEQ ID NO:10—pfRh1 amino acid sequence
SEQ ID NO:11—pfRh2a amino acid sequence
SEQ ID NO:12—pfRh2a/b 15 kDa antigenic fragment
SEQ ID NO:13—pfRh2a/b antigenic fragment 2030-2528
SEQ ID NO:14—pfRh2b amino acid sequence
SEQ ID NO:15 pfRh4 amino acid sequence
SEQ ID NO:16—pfRh4 antigenic fragment 28-766
SEQ ID NO:17—pfRh5 amino acid sequence
SEQ ID NO:18—pfRh5 antigenic fragment (minus leader sequence)
SEQ ID NO:19—pfRh5 antigenic fragment
SEQ ID NO:20—pfRh5 antigenic fragment
SEQ ID NO:21—pfRh5 antigenic fragment
SEQ ID NO:22—pfRh5 antigenic fragment
SEQ ID NO:23—pfRh5 antigenic fragment
SEQ ID NO:24—pfRh5 antigenic fragment
SEQ ID NO:25—pfRh5 antigenic fragment
SEQ ID NO:26—pfRh5 antigenic fragment
SEQ ID NO:27—pfRh5 antigenic fragment
SEQ ID NO:28—pfRh5 antigenic fragment
SEQ ID NO:29—pfRh5 peptide 187-197
SEQ ID NO:30—pfRh5 peptide 212-221
SEQ ID NO:31—pfRh5 peptide 237-247
SEQ ID NO:32—pfRh5 peptide 303-310
SEQ ID NO:33—pfRh5 peptide 358-366
SEQ ID NO:34—pfRh5 peptide 437-443
SEQ ID NO:35—pfEBA175 amino acid sequence
SEQ ID NO:36—pfEBA175 antigenic fragment 760-1271
SEQ ID NO:37—pfEBA181 amino acid sequence
SEQ ID NO:38—pfEBA140 amino acid sequence
SEQ ID NO:39—pfRip 238-368 codon optimised
SEQ ID NO:40—pfRip 791-900 forward primer
SEQ ID NO:41 pfRip 791-900 reverse primer
SEQ ID NO:42—pfRh2a/b 15 kDa DNA sequence
SEQ ID NO:43—MSP-1 amino acid sequence
SEQ ID NO:44 MSP-1(42) amino acid sequence
SEQ ID NO:45—MSP-1(19) amino acid sequence
SEQ ID NOs:46 to 57—Peptide linkers

DETAILED DESCRIPTION

General Techniques and Selected Definitions

Unless specifically defined otherwise, all technical and scientific terms used herein shall be taken to have the same meaning as commonly understood by one of ordinary skill in the art (e.g., in immunology, protein chemistry, biochemistry, cell culture, microbiology, and molecular genetics).

Unless otherwise indicated, the immunological, microbiological and molecular genetic techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, 3$^{rd}$ ed., Cold Spring Harbour Laboratory Press (2001), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al., (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al., (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

As used herein, the term about, unless stated to the contrary, refers to +/−20%, more preferably +/−10%, of the designated value.

As used herein, the term "subject" refers to an animal, e.g., a mammal. In one embodiment, the subject is a human.

"Administering" as used herein is to be construed broadly and includes administering a composition or polypeptide as described herein to a subject as well as providing a composition or polypeptide as described herein to a cell.

As used herein the terms "treating", "treat" or "treatment" include administering a therapeutically effective amount of a composition, polypeptide, polynucleotide, vector, cell and/or antibody the invention sufficient to reduce the severity of or eliminate at least one symptom of malaria in a subject such as prostration, impaired consciousness, respiratory distress (acidotic breathing), multiple convulsions, circulatory collapse, pulmonary oedema (radiological), abnormal bleeding, jaundice, and/or haemoglobinuria.

The term "preventing" refers to protecting a subject from developing at least one symptom of malaria, or delaying the onset of a symptom of malaria in a subject.

Polypeptides and Antigenic Fragments

The terms "polypeptide" and "protein" as used herein are generally used interchangeably and refer to a polypeptide chain which may or may not be modified by addition of non-amino acid groups. Thus, the protein may be glycosylated, unglcosysolated, and/or may contain other molecules fused, linked, bound or otherwise associated to the protein such as amino acids, lipids, carbohydrates or other polypeptides. It would be understood that such polypeptide chains may associate with other polypeptides or proteins or other molecules such as co-factors. The terms "proteins" and "polypeptides" as used herein also include variants, mutants, biologically active fragments, modifications, analogous and/or derivatives of the polypeptides described herein.

By "isolated polypeptide" we mean a polypeptide that has generally been separated from the lipids, nucleic acids, other peptides, and other contaminating molecules with which it is associated in its native state. Preferably, the substantially purified polypeptide is at least 60% free, more preferably at least 75% free, and more preferably at least 90% free from other components with which it is naturally associated.

The term "recombinant" in the context of a polypeptide refers to the polypeptide when produced by a cell, or in a cell-free expression system, in an altered amount or at an altered rate compared to its native state. In one embodiment the cell is a cell that does not naturally produce the polypeptide. However, the cell may be a cell which comprises a non-endogenous gene that causes an altered, preferably increased, amount of the polypeptide to be produced. A recombinant polypeptide of the invention includes polypeptides which have not been separated from other components of the transgenic (recombinant) cell, or cell-free expression system, in which it is produced, and polypeptides produced in such cells or cell-free systems which are subsequently purified away from at least some other components.

The % identity of a polypeptide is determined by GAP (Needleman and Wunsch, 1970) analysis (GCG program) with a gap creation penalty=5, and a gap extension penalty=0.3. The query sequence is at least 15 amino acids in length, and the GAP analysis aligns the two sequences over a region of at least 15 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. More preferably, the query sequence is at least 250 amino acids in length and the GAP analysis aligns the two sequences over a region of at least 250 amino acids. More preferably, the query sequence is at least 500 amino acids in length and the GAP analysis aligns the two sequences over a region of at least 500 amino acids. More preferably, the two sequences are aligned over their entire length.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence mutants of the polypeptides of the present invention can be prepared by introducing appropriate nucleotide changes into a nucleic acid of the present invention, or by in vitro synthesis of the desired polypeptide. Such mutants include, for example, deletions, insertions or substitutions of residues within the amino acid sequence. A combination of deletion, insertion and substitution can be made to arrive at the final construct, provided that the final polypeptide product possesses the desired characteristics, for example immunogenicity.

Mutant (altered) polypeptides can be prepared using any suitable technique known in the art. For example, a polynucleotide of the invention can be subjected to in vitro mutagenesis. Such in vitro mutagenesis techniques include sub-cloning the polynucleotide into a suitable vector, transforming the vector into a "mutator" strain such as the E. coli XL-1 red (Stratagene) and propagating the transformed bacteria for a suitable number of generations. In another example, the polynucleotides of the invention are subjected to DNA shuffling techniques as broadly described by Harayama (1998). These DNA shuffling techniques may include orthologous genes from closely related species. Products derived from mutated/altered DNA can readily be screened using techniques described herein to determine if they possess desired characteristics.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. Amino acids are preferably substituted in a relatively conservative manner. Such conservative substitutions are shown in Table 1 under the heading of "exemplary substitutions".

TABLE 1

Exemplary substitutions.

| Original Residue | Exemplary Substitutions |
| --- | --- |
| Ala (A) | Val; Leu; Ile; Gly |
| Arg (R) | Lys |
| Asn (N) | Gln; His |
| Asp (D) | Glu |
| Cys (C) | Ser |
| Gln (Q) | Asn; His |
| Glu (E) | Asp |
| Gly (G) | Pro, Ala |
| His (H) | Asn; Gln |
| Ile (I) | Leu; Val; Ala |
| Leu (L) | Ile; Val; Met; Ala; Phe |
| Lys (K) | Arg |
| Met (M) | Leu; Phe |
| Phe (F) | Leu; Val; Ala |
| Pro (P) | Gly |
| Ser (S) | Thr |
| Thr (T) | Ser |
| Trp (W) | Tyr |
| Tyr (Y) | Trp; Phe |
| Val (V) | Ile; Leu; Met; Phe, Ala |

Furthermore, if desired, unnatural amino acids or chemical amino acid analogues can be introduced as a substitution or addition into the polypeptides of the present invention. Such amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general.

Also included within the scope of the invention are polypeptides of the present invention which are differentially modified during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or immunogenicity of the polypeptide of the invention.

Polypeptides of the present invention can be produced in a variety of ways, including production and recovery of natural polypeptides, production and recovery of recombinant polypeptides, and chemical synthesis of the polypeptides. In one embodiment, an isolated polypeptide of the present invention is produced by culturing a cell capable of expressing the polypeptide under conditions effective to produce the polypeptide, and recovering the polypeptide. A preferred cell to culture is a host cell of the present invention. Effective culture conditions include, but are not limited to, effective media, bioreactor, temperature, pH and oxygen conditions that permit polypeptide production. An effective medium refers to any medium in which a cell is cultured to produce a polypeptide of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

The terms "antigen", "antigenic", "antigenic fragmant" and the like are well understood in the art and refer to the portion of a macromolecule, for example a polypeptide defined herein, which is specifically recognized by a component of the immune system, for example, an antibody or a T-cell antigen receptor. The term "antigen" therefore refers to a peptide, a polypeptide, or other macromolecule to which an immune response can be induced in a host. Thus, the invention includes an antigenic fragment of a polypeptide defined herein. Preferably, the antigenic fragment is capable of raising an immune response against a pathogen of the genus Plasmodium, for example Plasmodium falicparum, Plasmodium vivax, Plasmodium ovale curtisi, Plasmodium ovale wallikeri, Plasmodium malariae, and/or Plasmodium knowlesi. In one embodiment, the antigenic fragment is 6 amino acids in length, more preferably 7 amino acids in length, more preferably 8 amino acids in length, more preferably 9 amino acids in length, more preferably at least 10 amino acids in length. Alternatively the antigenic fragment is at least 20, 30, 40, 50, 60, 70, 80, 90, 100 or more amino acids in length. In an embodiment, the antigenic fragment when administered to a subject is able to elicit an immune response against at least one polypeptide comprising an amino acid sequence as provided in any one of SEQ ID NOs:2 to 4, 10 to 28 or 35 to 38. Further examples of antigenic fragments useful for the invention are described in WO 2010/022452, US 2009/0175895 and US 2009/0202579, some of which are outlined in further detail below.

Rip

In a particularly preferred embodiment, a composition of the invention comprises a Rip polypeptide, or antigenic fragment thereof. An example of an *P. falciparum* Rip polypeptide is provided as SEQ ID NO:2. It is known to the skilled person that there are a large number of single nucleotide polymorphism in Rip and these and any other mutations are included within the scope of the invention. Particular polymorphisms include changes to amino acids N144 to K, V190 to A, H511 to R, L673 to V, A755 to G, Y985 to N, and/or I1039 to M.

In a particularly preferred embodiment, the Rip antigenic fragment comprises, more preferably consists of, EGF domains 5 and 6 of the group of 8 EGF domains (see FIG. 6A), such as i) an amino acid sequence as set forth in SEQ ID NO:3, ii) an amino acid sequence which is at least 70% identical to SEQ ID NO:3, and/or iii) an antigenic fragment of i) or ii).

Examples of other RIP antigenic fragments include those comprising or consisting of, one, preferably two or more, and up to all 8 (such as about amino acid 636 to about amino acid 979) of the EGF domains towards the C-terminal end of pfRip (see FIGS. 6A and 6B).

Rh1

In an embodiment, a composition of the invention comprises or consists of an Rh1 polypeptide, or antigenic fragment thereof. An example of an *P. falciparum* Rh1 polypeptide is provided as SEQ ID NO:10. It is known to the skilled person that there are a large number of single nucleotide polymorphism in Rh1 and these and any other mutations are included within the scope of the invention.

In one embodiment, the antigenic fragment comprises or consists of the region between about amino acid residue 1 to the transmembrane domain of Rh1.

Rh2a

In an embodiment, a composition of the invention comprises or consists of an Rh2a polypeptide, or antigenic fragment thereof. An example of an *P. falciparum* Rh2a polypeptide is provided as SEQ ID NO:11. It is known to the skilled person that there are a large number of single nucleotide polymorphism in Rh2a and these and any other mutations are included within the scope of the invention. Examples of such mutations are whereby A at amino acid 2546 is replaced with D, E at amino acid 2613 is replaced with G, R at amino acid 2723 is replaced with K, or K at amino acid 2725 replaced with Q.

In one embodiment, the antigenic fragment of Rh2a comprises or consists of the region between about 31 amino acids N-terminal of the Prodom PD006364 homology region to about the transmembrane domain of Rh2a. The antigenic fragment may also comprise or consist of the region from about residue 2133 to about residue 3065, the region from about residue 2098 to about residue 2597, or the region from about residue 2616 to about residue 3115, of Rh2a.

In a particularly preferred embodiment, the Rh2a antigenic fragment comprises, more preferably consists of, i) an amino acid sequence as set forth in SEQ ID NO:12, ii) an amino acid sequence which is at least 70% identical to SEQ ID NO:12, and/or iii) an antigenic fragment of i) or ii).

In another particularly preferred embodiment, the Rh2a antigenic fragment comprises, more preferably consists of,
i) an amino acid sequence as set forth in SEQ ID NO:13,
ii) an amino acid sequence which is at least 70% identical to SEQ ID NO:13, and/or
iii) an antigenic fragment of i) or ii).

Rh2b

In an embodiment, a composition of the invention comprises or consists of an Rh2b polypeptide, or antigenic fragment thereof. An example of an *P. falciparum* Rh2a polypeptide is provided as SEQ ID NO:14. It is known to the skilled person that there are a large number of single nucleotide polymorphism in Rh2b and these and any other mutations are included within the scope of the invention. Examples of such mutations are whereby D at amino acid 2546 is replaced with A, K at amino acid 2635 is replaced with E, K at amino acid 3165 is replaced with N, or N at amino acid 3191 replaced with T or Y.

In one embodiment, the antigenic fragment of Rh2b comprises or consists of the region between about 31 amino acids N-terminal of the Prodom PD006364 homology region to about the transmembrane domain of Rh2b. The antigenic fragment may comprise or consist of the region from about residue 2027 to about residue 3115, more particularly from about residue 2027 to about residue 2533, of Rh2b. In other examples, the antigenic fragment may comprise or consist of the region from about residue 2098 to about residue 2597, or the region from about 2616 to 3115, of Rh2b.

In a particularly preferred embodiment, the Rh2b antigenic fragment comprises, more preferably consists of,
i) an amino acid sequence as set forth in SEQ ID NO:12,
ii) an amino acid sequence which is at least 70% identical to SEQ ID NO:12, and/or
iii) an antigenic fragment of i) or ii).

In another particularly preferred embodiment, the Rh2b antigenic fragment comprises, more preferably consists of,
i) an amino acid sequence as set forth in SEQ ID NO:13,
ii) an amino acid sequence which is at least 70% identical to SEQ ID NO:13, and/or
iii) an antigenic fragment of i) or ii).

Rh4

In an embodiment, a composition of the invention comprises or consists of an Rh4 polypeptide, or antigenic fragment thereof. An example of an *P. falciparum* Rh4 polypeptide is provided as SEQ ID NO:15. It is known to the skilled person that there are a large number of single nucleotide polymorphism in Rh4 and these and any other mutations are included within the scope of the invention. Examples of such mutations are whereby Y at amino acid 12 is replaced with A, L at amino acid 143 is replaced with I, N at amino acid 435 is replaced with K, Q at amino acid 438 is replaced with K, T at amino acid 506 replaced with K, N at amino acid 771 is replaced with S, N at amino acid 844 is replaced with I, K at amino acid 1482 is replaced with R, or N at amino acid 1498 is replaced with I.

In one embodiment, the antigenic fragment of Rh2b comprises or consists of the region from about the MTH1187/YkoF-like superfamily domain to about the transmembrane domain of Rh4. The antigenic fragment may comprise or consist of the region from about residue 1160 to about residue 1370 of Rh4.

In another particularly preferred embodiment, the Rh4 antigenic fragment comprises, more preferably consists of,
i) an amino acid sequence as set forth in SEQ ID NO:16,
ii) an amino acid sequence which is at least 70% identical to SEQ ID NO:16, and/or
iii) an antigenic fragment of i) or ii).

Rh5

In an embodiment, a composition of the invention comprises or consists of an Rh5 polypeptide, or antigenic fragment thereof. An example of an *P. falciparum* Rh5 polypeptide is provided as SEQ ID NO:17. It is known to the skilled person that there are a large number of single nucleotide polymorphism in Rh5 and these and any other mutations are included within the scope of the invention. Examples of such mutations are whereby E at amino acid 48 is replaced with K, Y at amino acid 147 is replaced with H, H at amino acid 148 is replaced with N, S at amino acid 197 is replaced with Y, C at amino acid 203 is replaced with Y, I at amino acid 204 is replaced with K or R, N at amino acid 347 is replaced with Y or D, Y at amino acid 358 is replaced with F, E at amino acid 362 is replaced with D, V at amino acid 371 is replaced with I, I at amino acid 407 is replaced with V, I at amino acid 410 is replaced with M, or K at amino acid 429 is replaced with N.

In one embodiment, the antigenic fragment lacks the 23 amino acid N-terminal leader sequence (SEQ ID NO:18). In alternate embodiments, the antigenic fragment may comprise or consist of one of the amino acid sequences provided as SEQ ID NO:19 to SEQ ID NO:28, or variants thereof such as where one or more of the above-mentioned mutations of Rh5 are present. In further embodiments, the antigenic fragment may comprise or consist of residues from about residue 203 to about residue 224, 317, 329, 345, or 351; or residues from about residue 224 to about residue 317, 329, 345, or 351; or residues from about residue 329 to about residue 345 or 351, or residues from about residue 345 to about residue 351. In one embodiment, cysteines 203 (polymorphic in *P. falciparum*) and 329 (absent in *P. reichenowi*) pair in the molecule by way of disulfide bridge to form a loop. Accordingly, in one form of the invention the antigenic fragment may comprise or consist of amino acid residues from about residue 203 to about residue 329. It is further proposed that cysteines 224 and 317 pair with either cysteine 345 or cysteine 351, such that the antigenic fragment may comprise or consist of residues from about residue 224 to about residue 345 or 351; or from about residue 317 to about residue 345 or 351.

EBA175

In a further embodiment, a composition of the invention comprises or consists of EBA175, or antigenic fragment thereof. An example of an *P. falciparum* EBA175 polypeptide is provided as SEQ ID NO:35. It is known to the skilled person that there are a large number of single nucleotide polymorphism in EBA175 and these and any other mutations are included within the scope of the invention. Examples of such mutations are whereby N at amino acid 157 replaced with S, E at amino acid 274 replaced with K, K at amino acid 279 replaced with E, K at amino acid 286 replaced with E, D at amino acid 336 replaced with Y, K at amino acid 388 replaced with N, P at amino acid 390 replaced with S, E at amino acid 403 replaced with K, K at amino acid 448 replaced with E, K at amino acid 478 replaced with N K at amino acid 481 replaced with I, N at amino acid 577 replaced with K, Q at amino acid 584 replaced with K, R at amino acid 664 replaced with S, S at amino acid 768 replaced with N, E at amino acid 923 replaced with K, K at amino acid 932 replaced with E, E at amino acid 1058 replaced with V, or G at amino acid 1100 replaced with D.

In one embodiment, the antigenic fragment is found in the region between the F2 domain and the transmembrane domain of the EBA175 protein.

In a particularly preferred embodiment, the EBA175 antigenic fragment comprises, more preferably consists of,
i) an amino acid sequence as set forth in SEQ ID NO:36,
ii) an amino acid sequence which is at least 70% identical to SEQ ID NO:36, and/or
iii) an antigenic fragment of i) or ii).

EBA181

In a further embodiment, a composition of the invention comprises or consists of EBA181, or antigenic fragment thereof. An example of an *P. falciparum* EBA181 polypeptide is provided as SEQ ID NO:37. It is known to the skilled person that there are a large number of single nucleotide polymorphism in EBA181 and these and any other mutations are included within the scope of the invention. Examples of such mutations are whereby V at amino acid 64 replaced with L, Q at amino acid 364 replaced with H, V at amino acid 363 replaced with D, R at amino acid 358 replaced with K, N at amino acid 414 replaced with I, K at amino acid 443 replaced with Q, P at amino acid 878 replaced with Q, E at amino acid 884 replaced with Q, E at amino acid 1885 replaced with K, Q at amino acid 890 replaced with E, P at amino acid 1197 replaced with L, K at amino acid 1219 replaced with N, D at amino acid 1433 replaced with Y or N, or K at amino acid 1518 replaced with E.

In one embodiment, the antigenic fragment is found in the region between the F2 domain and the transmembrane domain of the EBA181 protein. The antigenic fragment may comprise or consist of the region from about residue 755 to about residue 1339 of EBA181.

EBA140

In a further embodiment, a composition of the invention comprises or consists of EBA140, or antigenic fragment thereof. An example of an *P. falciparum* EBA140 polypeptide is provided as SEQ ID NO:38. It is known to the skilled person that there are a large number of single nucleotide polymorphism in EBA140 and these and any other mutations are included within the scope of the invention. Examples of such mutations are whereby V at amino acid 19 replaced with I, L at amino acid 112 replaced with F, I at amino acid 185 replaced with V, N at amino acid 239 replaced with S, K at amino acid 261 replaced with T.

In one embodiment, the antigenic fragment is found in the region between the F2 domain and the transmembrane domain of the EBA140 protein. The antigenic fragment may comprise or consist of the region from about residue 746 to about residue 1045 of EBA140.

Fusion Proteins

In one embodiment, a composition of the invention comprises a polypeptide which is a fusion protein comprising at least one other polypeptide sequence. The at least one other polypeptide may be, for example, a polypeptide that enhances the stability of a polypeptide of the present invention, or a polypeptide that assists in the purification or detection of the fusion protein, or preferably a polypeptide capable of eliciting an immune response in an animal, especially a human. By way of non-limiting example, the at least one other polypeptide sequence may comprise one or more T cell epitopes for recruitment of T helper cells or activation of cytotoxic T cells, or one or more antigens, cytokines and/or chemokines.

In an embodiment, the at least one other polypeptide is a polypeptide from *Plasmodium falciparum*. Preferably, the at least one other polypeptide from *Plasmodium falciparum* comprises one or more T cell epitopes for recruitment of T helper cells, and/or one or more MHC class I or MHC class II motifs. Methods for the identification of T cell epitopes and MHC class I and MHC class II motifs are known in the art and described in, for example, Rammensee (1995), Ohta et al. (1998), and Singh et al. (2010).

In one particular embodiment, the at least one other polypeptide is merozoite surface protein-1 (MSP-1) or a fragment of at least 50 amino acids thereof. An example of MSP-1 is provided as SEQ ID NO:43 (GenBank Accession No. BAF62268.1 and related molecules). Examples of MSP-1 fragments include MSP-1(42) provided as SEQ ID NO:44 and MSP-1(19) provided as SEQ ID NO:45.

In addition, the fusion protein may comprise one or more linkers or spacers. A "linker" or "spacer" as used herein refers to a peptide, polypeptide or other molecule, for example a straight or branched-chain carbon linker or heterocyclic carbon linker, that may be included between two polypeptides in a fusion protein to enhance expression of the protein in a bacterial or eukaryotic cell or to decrease steric hindrance such that one or more of the polypeptides in the fusion protein may assume its desired tertiary structure and/or interact appropriately with its target molecule, such as, for example, a B cell receptor or T cell receptor. Thus, the fusion protein may comprise one or more spacers before, after, or between one or more polypeptide domains in the fusion polypeptide. Suitable linkers are well known to those of skill in the art and include, but are not limited to, straight or branched-chain carbon linkers, heterocyclic carbon linkers, or peptide linkers. For spacers and methods of identifying desirable spacers, see, for example, George, et al. (2003).

In one embodiment, the spacer comprises one or more amino acid sequences that are, between 1-50 amino acid residues in length, or about 1-25 residues, or about 5-15 residues in length.

Non-limiting examples of peptide linkers include AAA, GGG, SGG, GGSGGS (SEQ ID NO:46), SAT, PYP, PSPSP (SEQ ID NO:47), ASA, ASASA (SEQ ID NO:48), PSPSP (SEQ ID NO:49), KKKK (SEQ ID NO:50), RRRR (SEQ ID NO:51), GGGG (SEQ ID NO:52), GGGGS (SEQ ID NO:53), GGGGS GGGGS (SEQ ID NO:54), GGGGS GGGGS GGGGS GGGGS (SEQ ID NO:55), GGGGS GGGGS GGGGS GGGGS (SEQ ID NO:56), and GGGGS GGGGS GGGGS GGGGS GGGGS (SEQ ID NO:57).

As known in the art, various chemical groups may be incorporated in the spacer segment instead of amino acids. Examples are described in U.S. Pat. No. 5,910,300. In one embodiment the spacer is comprised of an aliphatic chain optimally interrupted by heteroatoms, for example a $C_2$-$C_6$ alkylene, or =N—$(CH_2)_{2-6}$—N=. Alternatively, a spacer may be composed of alternating units, for example of hydrophobic, lipophilic, aliphatic and aryl-aliphatic sequences, optionally interrupted by heteroatoms such as O, N, or S. Such components of a spacer are preferably chosen from the following classes of compounds: sterols, alkyl alcohols, polyglycerides with varying alkyl functions, alkyl-phenols, alkyl-amines, amides, hydroxyphobic polyoxyalkylenes, and the like. Other examples are hydrophobic polyanhydrides, polyorthoesters, polyphosphazenes, polyhydroxy acids, polycaprolactones, polylactic, polyglycolic polyhydroxy-butyric acids. A spacer may also contain repeating short aliphatic chains, such as polypropylene, isopropylene, butylene, isobutylene, pentamethlyene, and the like, separated by oxygen atoms.

Antibodies

The term "antibody" as used in this invention includes polyclonal, monoclonal, chimeric and humanised antibodies, and includes intact molecules as well as molecules comprising or consisting of fragments thereof, such as Fab, F(ab')2, and Fv which are capable of binding an epitopic determinant.

Thus, antibodies may exist as intact immunoglobulins, or as modifications in a variety of forms including, for example, but not limited to, domain antibodies including either the VH or VL domain, a dimer of the heavy chain variable region (VHH, as described for a camelid), a dimer of the light chain variable region (VLL), Fv fragments containing only the light and heavy chain variable regions, or Fd fragments containing the heavy chain variable region and the CH1 domain. A scFv consisting of the variable regions of the heavy and light chains linked together to form a single-chain antibody and oligomers of scFvs such as diabodies and triabodies are also encompassed by the term "antibody". As outlined above, also encompassed are fragments of antibodies such as Fab, (Fab')$_2$ and FabFc$_2$ fragments which contain the variable regions and parts of the constant regions. CDR-grafted antibody fragments and oligomers of antibody fragments are also encompassed. The heavy and light chain components of an Fv may be derived from the same antibody or different antibodies thereby producing a chimeric Fv region. The antibody may be of animal (for example mouse, rabbit, chicken or rat) or human origin or may be chimeric or humanized.

The antibodies may be Fv regions comprising a variable light ($V_L$) and a variable heavy ($V_H$) chain. The light and heavy chains may be joined directly or through a linker. As used herein a linker refers to a molecule that is covalently linked to the light and heavy chain and provides enough spacing and flexibility between the two chains such that they are able to achieve a conformation in which they are capable of specifically binding the epitope to which they are directed. Protein linkers are particularly preferred as they may be expressed as an intrinsic component of the Ig portion of the fusion polypeptide.

As used herein, the term "specifically binds" shall be taken to mean a protein of the invention reacts or associates more frequently, more rapidly, with greater duration and/or with greater affinity with a particular antigen or antigens or cell expressing same than it does with alternative antigens or cells. For example, a protein that specifically binds to an antigen binds that antigen with greater affinity, avidity, more readily, and/or with greater duration than it binds to other antigens. It is also understood by reading this definition that, for example, a protein that specifically binds to a first antigen may or may not specifically bind to a second antigen. As such, "specific binding" does not necessarily require exclusive binding or non-detectable binding of another antigen, this is meant by the term "selective binding". Generally, but not necessarily, reference to binding means specific binding, and each term shall be understood to provide explicit support for the other term.

The antibody may be detectably labelled, such as for example, labelled with a fluorescent label (e.g. FITC or Texas Red), radiolabel, or an enzyme (e.g. horseradish peroxidase (HRP)), alkaline phosphatase (AP) or β-galactosidase.

A variety of immunoassay formats may be used to select antibodies specifically immunoreactive with the polypeptides of the invention. For example, surface labelling and flow cytometric analysis or solid-phase ELISA immunoassays are routinely used to select antibodies specifically immunoreactive with a protein or carbohydrate. See Harlow & Lane (supra) for a description of immunoassay formats and conditions that can be used to determine specific immunoreactivity.

Polynucleotides

By "isolated polynucleotide" we mean a polynucleotide which has generally been separated from the polynucleotide sequences with which it is associated or linked in its native state. Preferably, the isolated polynucleotide is at least 60% free, more preferably at least 75% free, and more preferably at least 90% free from other components with which it is naturally associated. Furthermore, the term "polynucleotide" is used interchangeably herein with the terms "nucleic acid molecule", "gene" and "mRNA".

The term "exogenous" in the context of a polynucleotide refers to the polynucleotide when present in a cell, or in a cell-free expression system, in an altered amount compared to its native state. In one embodiment, the cell is a cell that does not naturally comprise the polynucleotide. However, the cell may be a cell which comprises a non-endogenous polynucleotide resulting in an altered, preferably increased, amount of production of the encoded polypeptide. An exogenous polynucleotide of the invention includes polynucleotides which have not been separated from other components of the transgenic (recombinant) cell, or cell-free expression system, in which it is present, and polynucleotides produced in such cells or cell-free systems which are subsequently purified away from at least some other components.

"Polynucleotide" as used herein refers to a oligonucleotide, polynucleotide or any fragment thereof. It may be DNA or RNA of genomic or synthetic origin, double-stranded or single-stranded, and combined with carbohydrate, lipids, protein, or other materials to perform a particular activity defined herein.

The % identity of a polynucleotide is determined by GAP (Needleman and Wunsch, 1970) analysis (GCG program) with a gap creation penalty=5, and a gap extension penalty=0.3. The query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. Even more preferably, the query sequence is at least 300 nucleotides in length and the GAP analysis aligns the two sequences over a region of at least 300 nucleotides. More preferably, the two sequences are aligned over their entire length.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 40%, more preferably at least 45%, more preferably at least 50%, more preferably at least 55%, more preferably at least 60%, more preferably at least 65%, more preferably at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Polynucleotides of the present invention may possess, when compared to naturally occurring molecules, one or more mutations which are deletions, insertions, or substitutions of nucleotide residues. Mutants can be either naturally occurring (that is to say, isolated from a natural source) or synthetic (for example, by performing site-directed mutagenesis or DNA shuffling on the nucleic acid as described above).

It is thus apparent that polynucleotides of the invention can be either naturally occurring or recombinant.

Polynucleotides of the invention include those which hybridize under stringent conditions to a polynucleotide comprising a sequence of nucleotides which is at least 50% identical, preferably at least 70% identical, more preferably at least 90% identical, to SEQ ID NO:1, SEQ ID NO:39 or SEQ ID NO:42. The term "stringent hybridization conditions" and the like as used herein refers to parameters with which the art is familiar, including the variation of the hybridization temperature with length of an oligonucleotide. Nucleic acid hybridization parameters may be found in references which compile such methods, Sambrook, et al. (supra), and Ausubel, et al. (supra). For example, "moderately stringent" hybridization conditions, as used herein, can refer to hybridization at 20° C. to 64° C. in 3.5×SSC, 0.1% w/v SDS, and "high stringency" conditions can refer to hybridization at 65° C. in 0.2×SSC, 0.02% Ficoll, 0.02% polyvinyl pyrrolidone, 0.02% Bovine Serum Albumin, 2.5 mM $NaH_2PO_4$ (pH7), 0.5% SDS, 2 mM EDTA.

Vectors and Host Cells

One embodiment of the present invention includes a recombinant vector, which comprises at least one isolated polynucleotide molecule of the present invention, inserted into any vector capable of delivering the polynucleotide molecule into a host cell. Such a vector contains heterologous polynucleotide sequences, that is polynucleotide sequences that are not naturally found adjacent to polynucleotide molecules of the present invention and that preferably are derived from a species other than the species from which the polynucleotide molecule(s) are derived. The vector can be either RNA or DNA, either prokaryotic or eukaryotic, and may be a transposon, a virus or a plasmid.

"Operably linked" as used herein refers to a functional relationship between two or more nucleic acid (e.g., DNA) segments. Typically, it refers to the functional relationship of a transcriptional regulatory element to a transcribed sequence. For example, a promoter is operably linked to a coding sequence, such as a polynucleotide defined herein, if it stimulates or modulates the transcription of the coding sequence in an appropriate cell. Generally, promoter transcriptional regulatory elements that are operably linked to a transcribed sequence are physically contiguous to the transcribed sequence, i.e., they are cis-acting. However, some transcriptional regulatory elements, such as enhancers, need not be physically contiguous or located in close proximity to the coding sequences whose transcription they enhance.

As used herein, an expression vector is a DNA or RNA vector that is capable of transforming a host cell and of effecting expression of a specified polynucleotide molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, arthropod, animal, and plant cells.

In particular, expression vectors of the present invention contain regulatory sequences such as transcription control sequences, translation control sequences, origins of replication, and other regulatory sequences that are compatible with the recombinant cell and that control the expression of polynucleotide molecules of the present invention. In particular, expression vectors of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art.

Recombinant molecules of the present invention may also (a) contain secretory signals (i.e., signal segment nucleic acid sequences) to enable an expressed polypeptide of the present invention to be secreted from the cell that produces the polypeptide and/or (b) contain fusion sequences which lead to the expression of nucleic acid molecules of the present invention as fusion proteins. Examples of suitable signal segments include any signal segment capable of directing the secretion of a polypeptide of the present invention. Recombinant molecules may also include intervening and/or untranslated sequences surrounding and/or within the nucleic acid sequences of nucleic acid molecules of the present invention.

Another embodiment of the present invention includes a host cell comprising one or more recombinant molecules of the present invention. Transformation of a polynucleotide molecule into a cell can be accomplished by any method by which a polynucleotide molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed polynucleotide molecules of the present invention can remain extrachromosomal or can integrate into one or more sites within a chromosome of the transformed (i.e., recombinant) cell in such a manner that their ability to be expressed is retained.

Suitable host cells to transform include any cell that can be transformed with a polynucleotide of the present invention. Host cells of the present invention either can be endogenously (i.e., naturally) capable of producing polypeptides of the present invention or can be capable of producing such polypeptides after being transformed with at least one polynucleotide molecule of the present invention. Host cells of the present invention can be any cell capable of producing at least one protein of the present invention, and include animal, plant, bacterial, fungal (including yeast), parasite, and arthropod cells. Preferably, the host cell is a bacterial cell, for example *E. coli*.

Recombinant DNA technologies can be used to improve expression of a transformed polynucleotide molecule by manipulating, for example, the number of copies of the polynucleotide molecule within a host cell, the efficiency with which those polynucleotide molecules are transcribed, the efficiency with which the resultant transcripts are translated, and the efficiency of post-translational modifications. Recombinant techniques useful for increasing the expression of polynucleotide molecules of the present invention include, but are not limited to, operatively linking polynucleotide molecules to high-copy number plasmids, integration of the polynucleotide molecule into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of polynucleotide molecules of the present invention to correspond to the codon usage of the host cell, and the deletion of sequences that destabilize transcripts.

Compositions and Administration

The present invention provides compositions comprising the polypeptide, including antigenic fragments, defined herein. In one embodiment, the composition is an immunogenic composition. An "immunogenic composition" refers to a composition that comprises materials that elicit a desired immune response and includes a "vaccine". The term "vaccine" covers any composition that induces an at least partially protective immune response against a targeted pathogen or which efficaciously protects against the pathogen; for instance, after administration or injection into the subject (for example, a mammal such as a human), elicits an at least partially protective immune response against the targeted pathogen or provides efficacious protection against the pathogen (e.g., *Plasmodium falciparum*). By inducing an "at least partially protective" immune response it is meant that a vaccine reduces infection and/or reduces at least one symptom caused by infection with a pathogen expressing at least one polypeptide as defined herein.

An immunogenic composition may select, activate or expand cells of the immune system including memory B and T cells to, for example, enable the elimination of infectious agents, such as pathogens expressing at least one polypeptide as defined herein.

In some embodiments, an immunogenic composition includes a suitable carrier, such as an adjuvant, which is an agent that acts in a non-specific manner to increase the immune response to a specific antigen, or to a group of antigens, enabling the reduction of the quantity of antigen in any given dose, or the reduction of the frequency of dosage required to generate the desired immune response. A desired immune response may include, for example, full or partial protection against infection by a *Plasmodium* species or full or partial protection from developing one or more symptoms of malaria. For example, a desired immune response may include any value from between 10% to 100%, e.g., 10%, 20%, 30%, 40%, 50%, 60%, 70%, 80%, 90%, 100%, protection against infection by *Plasmodium* in a vaccinated subject when compared to a non-vaccinated subject.

Adjuvants are useful for improving the immune response and/or increasing the stability of vaccine preparations. Adjuvants are typically described as non-specific stimulators of the immune system, but also can be useful for targeting specific arms of the immune system. One or more compounds which have this activity may be added to the vaccine. Therefore, particular vaccines of the present invention further comprise an adjuvant. Examples of chemical compounds that can be used as adjuvants include, but are not limited to aluminum compounds (e.g., alum, aluminum hydroxide), metabolizable and non-metabolizable oils, mineral oils including mannide oleate derivatives in mineral oil solution (e.g., MONTANIDE ISA 70 from Seppic SA, France), and light mineral oils such as DRAKEOL 6VR, block polymers, ISCOM's (immune stimulating complexes), vitamins and minerals (including but not limited to: vitamin E, vitamin A, selenium, and vitamin B12), saponin-based adjuvants (for example as described in Sun et al. (2009)) and CARBOPOL®. Other suitable adjuvants, which sometimes have been referred to as immune stimulants, include, but are not limited to: cytokines, growth factors, chemokines, supernatants from cell cultures of lymphocytes, monocytes, cells from lymphoid organs, cell preparations and/or extracts from plants, bacteria or parasites (*Staphylococcus aureus* or lipopolysaccharide preparations) or mitogens. Specific adjuvants include MPL, adjuvants from GSK's Adjuvant Systems such as the AS range, eg. AS01, AS02, AS03, AS04, AS15, fractions from *Quillaja saponaria* such as QH-B fraction, QS-7, QS-17, QS-18 and QS-21 fractions (Antigenics, New York, N.Y.). Further details regarding suitable adjuvants are provided in the following passages.

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. (e.g. see chapters 8 & 9 of Powell & Newman (eds.) Vaccine Design (1995) Plenum), or mixtures of different mineral compounds, with the compounds taking any suitable form (e.g. gel, crystalline, amorphous, etc.), and with adsorption being preferred. The mineral containing compositions may also be formulated as a particle of metal salt (WO 00/23105).

A typical aluminium phosphate adjuvant is amorphous aluminium hydroxyphosphate with $PO_4/Al$ molar ratio between 0.84 and 0.92, included at 0.6 mg $Al^{3+}$/ml. Adsorption with a low dose of aluminium phosphate may be used e.g. between 50 and 100 µg $Al^{3+}$ per conjugate per dose. Where an aluminium phosphate it used and it is desired not to adsorb an antigen to the adjuvant, this is favoured by including free phosphate ions in solution (e.g. by the use of a phosphate buffer).

Oil emulsion compositions suitable for use as adjuvants in the invention include oil-in-water emulsions and water-in-oil emulsions.

A submicron oil-in-water emulsion may include squalene, Tween 80, and Span 85 e.g. with a composition by volume of about 5% squalene, about 0.5% polysorbate 80 and about 0.5% Span 85 (in weight terms, 4.3% squalene, 0.5% polysorbate 80 and 0.48% Span 85), known as 'MF595' (57-59 chapter 10 of Powell & Newman (eds.) Vaccine Design (1995) Plenum; chapter 12 of O'Hagen (ed.) Vaccine Adjuvants: Preparation Methods and Research Protocols (Volume 42 of Methods in Molecular Medicine series)). The MF59 emulsion advantageously includes citrate ions e.g. 10 mM sodium citrate buffer.

An emulsion of squalene, a tocopherol, and Tween 80 can be used. The emulsion may include phosphate buffered saline. It may also include Span 85 (e.g. at 1%) and/or lecithin. These emulsions may have from 2 to 10% squalene, from 2 to 10% tocopherol and from 0.3 to 3% Tween 80, and the weight ratio of squalene tocopherol is preferably <1 as this provides a more stable emulsion. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm.

An emulsion of squalene, a tocopherol, and a Triton detergent (e.g. Triton X-100) can be used. An emulsion of squalane, polysorbate 80 and poloxamer 401 ("Pluronic™ L121") can be used. The emulsion can be formulated in phosphate buffered saline, pH 7.4. This emulsion is a useful delivery vehicle for muramyl dipeptides, and has been used with threonyl-MDP in the "SAF-I" adjuvant, (0.05-1% Thr-MDP, 5% squalane, 2.5% Pluronic L121 and 0.2% polysorbate 80). It can also be used without the Thr-MDP, as in the "AF" adjuvant (Hariharan et al. (1995) Cancer Res 55:3486-9) (5% squalane, 1.25% Pluronic L121 and 0.2% polysorbate 80). Microfluidisation is preferred.

Complete Freund's adjuvant (CFA) and incomplete Freund's adjuvant (IFA) may also be used.

Saponin formulations may also be used as adjuvants in the invention (see for example Chapter 22 of Powell & Newman (eds.) Vaccine Design (1995) Plenum). Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS 17, QS18, QS21, QH-A, QH-B and QH-C. Preferably, the saponin is QS21. Saponin formulations may also comprise a sterol, such as cholesterol (WO 96/33739).

As discussed supra, combinations of saponins and cholesterols can be used to form unique particles called immunostimulating complexes (ISCOMs) (see for example Chapter 23 of Powell & Newman (eds.) Vaccine Design (1995) Plenum). ISCOMs typically also include a phospholipid such as phosphatidylethanolamine or phosphatidylcholine. Any known saponin can be used in ISCOMs. Preferably, the ISCOM includes one or more of QuilA, QHA and QHC. ISCOMs are further described in WO 96/33739, EP-A-0109942, WO 96/11711). Optionally, the ISCOMS may be devoid of additional detergent WO 00/07621.

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein pi). VLPs are discussed further in WO03/024480 and WO03/024481.

Adjuvants suitable for use in the invention include bacterial or microbial derivatives such as non-toxic derivatives of enterobacterial lipopolysaccharide (LPS), Lipid A derivatives, immunostiinulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 77. Such "small particles" of 3dMPL are small enough to be sterile filtered through a 0.22 μm membrane (EP-A-0689454). Other non-toxic LPS derivatives include monophosphoryl lipid A mimics, such as aminoalkyl glucosamine de phosphate derivatives e.g. RC-529. Lipid A derivatives include derivatives of lipid A from *E. coli* such as 0M-174. OM-174.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory. The CpG's can include nucleotide modifications/analogs such as phosphorothioate modifications and can be double-stranded or single-stranded. WO02/26757 and WO99/62923 disclose possible analog substitutions e.g. replacement of guanosine with 2'-deoxy-7-deazaguanosine. The adjuvant effect of CpG oligonucleotides is further discussed in WO 98/40100, U.S. Pat. No. 6,207,646, U.S. Pat. No. 6,239,116 and U.S. Pat. No. 6,429, 199. The CpG sequence may be directed to TLR9, such as the motif GTCGTT or TTCGTT. The CpG sequence may be specific for inducing a TH1 immune response, such as a CpG-A ODN, or it may be more specific for inducing a B cell response, such a CpG-B ODN. CpG-A and CpG-B ODNs. Preferably, the CpG oligonucleotide is constructed so that the 5' end is accessible for receptor recognition. Optionally, two CpG oligonucleotide sequences may be attached at their 3' ends to form "immunomers" (see, for example, WO03/035836).

Other immunostimulatory oligonucleotides include a double-stranded RNA or an oligonucleotide containing a palindromic sequence, or an oligonucleotide containing a poly (dG) sequence.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in WO 95/17211 and as parenteral adjuvants in WO 98/42375. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192.

Human immunomodulators suitable for use as adjuvants in the invention include cytokines, such as interleukins (e.g. IL-15 IL-2, IL-4, IL-5, IL-6, IL-7, IL-12, IL-17, IL-18, IL-23, IL-27), interferons (e.g. interferon-γ), macrophage colony stimulating factor, tumor necrosis factor and macrophage inflammatory protein-1 alpha (MIP-1 alpha) and MIP-1 beta.

Bioadhesives and mucoadhesives may also be used as adjuvants in the invention. Suitable bioadhesives include esterified hyaluronic acid microspheres or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention (WO 99/27960).

Microparticles may also be used as adjuvants in the invention. Microparticles (i.e. a particle of ~100 nm to ~150 μm in diameter, more preferably ~0.200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

Examples of liposome formulations suitable for use as adjuvants are described in U.S. Pat. No. 6,090,406, U.S. Pat. No. 5,916,588, EP-A-0626169.

Adjuvants suitable for use in the invention include polyoxyethylene ethers and polyoxyethylene esters (WO 99/52549). Such formulations further include polyoxyethylene sorbitan ester surfactants in combination with an octoxynol (WO 01/21207) as well as polyoxyethylene alkyl ethers or ester surfactants in combination with at least one additional non-ionic surfactant such as an octoxynol (WO 01/21152).

Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

Phosphazene adjuvants include poly(di(carboxylatophenoxy)phosphazene) ("PCPP").

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

Imidazoquinoline adjuvants include Imiquimod ("R-837") (U.S. Pat. No. 4,680,338 and U.S. Pat. No. 4,988,815), Resiquimod ("R-848") (WO92/15582), and their analogs; and salts thereof (e.g. the hydrochloride salts). Further details about immunostimulatory imidazoquinolines can be found in U.S. Pat. Nos. 4,689,338, 4,929,624, 5,238,944, 5,266,575, 5,268,376, 5,346,905, 5,352,784, 5,389,640, 5,395,937, 5,482,936, 5,494,916, 5,525,612, 6,083,505, 6,440,992, 6,627,640, 6,656,938, 6,660,735, 6,660,747, 6,664,260, 6,664,264, 6,664,265, 6,667,312, 6,670,372, 6,677,347, 6,677,348, 6,677,349, 6,683,088, 6,703,402, 6,743,920, 6,800,624, 6,809,203, 6,888,000 and 6,924,293.

Thiosemicarbazone adjuvants include those disclosed in WO 2004/060308. Methods of formulating, manufacturing, and screening for active compounds are also described in WO 2004/060308. The thiosemicarbazones are particularly effective in the stimulation of human peripheral blood mononuclear cells for the production of cytokines, such as TNF-α.

Tryptanthrin adjuvants include those disclosed in WO 2004/064759. Methods of formulating, manufacturing, and screening for active compounds are also described in WO 2004/064759. The thiosemicarbazones are particularly effective in the stimulation of human peripheral blood mononuclear cells for the production of cytokines, such as TNF-α.

Various nucleoside analogs can be used as adjuvants, such as (a) Isatorabine (ANA-245; 7-thia-8-oxoguanosine) and prodrugs thereof; (b) ANA975; (c) ANA-025-1; (d) ANA380; (e) the compounds disclosed in U.S. Pat. No. 6,924,271, US 2005/0070556 and U.S. Pat. No. 5,658,731, or (f) a pharmaceutically acceptable salt of any of (a) to (g), a tautomer of any of (a) to (g), or a pharmaceutically acceptable salt of the tautomer.

Small molecule immunopotentiators useful as adjuvants include N2-methyl-1-(2-methylpropyl)-1H-imidazo(4,5-c) quinoline-2,4-diamine; N2,N2-dimethyl-1-(2-methylpropyl)-1H-imidazo(4,5-c)quinoline-2,4-diamine; N2-ethyl-N2-m ethyl-1-(2-methylpropyl)-1H-imidazo(4,5-c) quinoline-2,4-diamine; N2-methyl-1-(2-methylpropyl)-N2-propyl-1H-imidazo(4,5-c) quinoline-2,4-diamine; 1-(2-methylpropyl)-N2-propyl-1H-imidazo(4,5-c) quinoline-2,4-diamine; N2-butyl-1-(2-methylpropyl)-1H-imidazo(4,5-c) quinoline-2,4-diamine; N2-butyl-N2-methyl-1-(2-methylpropyl)-1H-imidazo(4,5-c)quinoline-2,4-diamine; N2-methyl-1-(2-methylpropyl)-N2-pentyl-1H-imidazo(4,5-c)quinoline-2,4-diamine; N2-methyl-1-(2-methylpropyl)-N2-prop-2-enyl-1H-imidazo(4,5-c)quinoline-2,4-diamine; 1-(2-methylpropyl)-2-((phenylmethyl)thio)-1H-imidazo (4,5-c)quinolin-4-amine; 1-(2-methylpropyl)-2-(propylthio)-1H-imidazo(4,5-c) quinolin-4-amine; 2-((4-amino-1-(2-methylpropyl)-1H-imidazo(4,5-c) quinolin-2-yl)(methyl) amino)ethanol; 2-((4-amino-1-(2-methylpropyl)-1H-imidazo(4,5-c)quinolin-2-yl)(methyl)amino)ethyl acetate; 4-amino-1-(2-methylpropyl)-1,3-dihydro-2H imidazo(4,5-c)quinolin-2-one; N2-butyl-1-(2-methylpropyl)-N4,N4-bis (phenylmethyl)-1H-imidazo(4,5-c) quinoline-2,4-diamine; N2-butyl-N2-methyl-1-(2-methylpropyl)-N4,N4-bis(phenylmethyl)-1H-imidazo(4,5-c) quinoline-2,4-diamine; N2-methyl-1-(2-methylpropyl)-N4,N4-bis(phenylmethyl)-1H-imidazo(4,5-c)quinoline-2,4-di amine; N2,N2-dimethyl-1-(2-methylpropyl)-N4,N4-bis(phenylmethyl)-1H-imidazo (4,5-c) quinoline-2,4-diamine; 1-(4-amino-2-(methyl (propyl)amino)-1H-imidazo(4,5-c) quinolin-1-yl}-2-methylpropan-2-ol; 1-(4-amino-2-(propylamino)-1H-imidazo(4,5-c) quinolin-1-yl)-2-methylpropan-2-ol; N43N4-dibenzyl-1-(2-methoxy-2-methylpropyl)-N2propyl-1H-imidazo(4,5-c)quinoline-2,4-diamine.

One potentially useful adjuvant is an outer membrane protein proteosome preparation prepared from a first Gram-negative bacterium in combination with a liposaccharide preparation derived from a second Gram-negative bacterium, wherein the outer membrane protein proteosome and liposaccharide preparations form a stable non-covalent adjuvant complex. Such complexes include "IVX-908", a complex comprised of *Neisseria meningitidis* outer membrane and lipopolysaccharides. They have been used as adjuvants for influenza vaccines (WO 02/072012).

Other substances that act as immunostimulating agents are disclosed in Vaccine Design ((1995) eds. Powell & Newman. ISBN: 030644867X. Plenum) and Vaccine Adjuvants: Preparation Methods and Research Protocols (Volume 42 of Methods in Molecular Medicine series) (ISBN: 1-59259-083-7. Ed. O'Hagan). Further useful adjuvant substances include: Methyl inosine 5'-monophosphate ("MIMP"); a polyhydroxlated pyrrolizidine compound (WO 2004/064715), examples include, but are not limited to: casuarine, casuarine-6-α-D-glucopyranose, 3-epz-casuarine, 7-epz-casuarine, 3,7-diepz-casuarine, etc; a gamma inulin or derivative thereof, such as algammulin; compounds disclosed in PCT/US2005/022769; compounds disclosed in WO 2004/87153, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds (U.S. Pat. No. 6,606,617, WO 02/018383), Hydrapthalamide compounds, Benzophenone compounds, Isoxazole compounds, Sterol compounds, Quinazilinone compounds, Pyrrole compounds (WO 04/018455), Anthraquinone compounds, Quinoxaline compounds, Triazine compounds, Pyrazalopyrimidine compounds, and Benzazole compounds (WO 03/082272); loxoribine (7-allyl-8-oxoguanosine) (U.S. Pat. No. 5,011,828); a formulation of a cationic lipid and a (usually neutral) co-lipid, such as aminopropyl dimethyl-myristoleyloxy-propanaminium bromide-diphytanoylphosphatidyl-ethanolamine ("Vaxfectin™") or aminopropyl-dimethyl-bis-dodecyloxy-propanaminium bromide-di oleoylphosphatidyl-ethanolamine ("GAP-DLRIE: DOPE"). Formulations containing (±)-N-(3-aminopropyl)-N,N-dimethyl-2,3-bis(syn-9-tetradeceneyloxy)-1-propanaminium salts are preferred (U.S. Pat. No. 6,586,409).

The invention may also comprise combinations of aspects of one or more of the adjuvants identified above. For example, the following adjuvant compositions may be used in the invention: (1) a saponin and an oil-in-water emulsion (WO 99/11241); (2) a saponin (e.g. QS21)+a nontoxic LPS derivative (e.g. 3dMPL) (WO 94/00153); (3) a saponin (e.g. QS21)+a non-toxic LPS derivative (e.g. 3dMPL)+a cholesterol; (4) a saponin (e.g. QS21)+3dMPL+IL-12 (optionally+a sterol) (WO 98/57659); (5) combinations of 3dMPL with, for example, QS21 and/or oil-in-water emulsions (EP 0835318, EP 0735898, EP 0761231); (6) Ribi™ adjuvant system (RAS), (Ribi Immunochem) containing 2% squalene, 0.2%

Tween 80, and one or more bacterial cell wall components from the group consisting of monophosphorylipid A (MPL), trehalose dimycolate (TDM), and cell wall skeleton (CWS), preferably MPL+CWS (Detox™); and (7) one or more mineral salts (such as an aluminum salt)+a non-toxic derivative of LPS (such as 3dMPL).

Generally, an adjuvant is administered at the same time as the antigen. However, adjuvants can also, or alternatively be administered within a two-week period prior to the vaccination, and/or for a period of time after vaccination, i.e., so long as the antigen persists in the tissues.

Vaccine may be administered in various ways known to the skilled person, for example in particulate form, such as on a microcarrier or a nanocarrier (Paolicelli et al., 2010). One particular system uses PRINT® technology by delivering the vaccine antigen on a dissolvable particle (Liquidia Technologies, NC, USA).

The immunogenic compositions and vaccines according to the invention may be further supplemented by the addition of other recombinant or purified antigens which may result in the production of antibodies of a variety of specificities when administered to a subject. Not all of these antibodies need to be protective against a disease. In a particular embodiment of this type, such antigens are also from *Plasmodium*, for example, from *Plasmodium falciparum*. Thus, a vaccine of the present invention may contain various other active or inactivated pathogenic factors, along with at least one polypeptide defined herein. Therefore, in accordance with the present invention, at least one polypeptide defined herein can be combined with other *Plasmodium* and non-*Plasmodium* antigens.

In one embodiment, the composition of the invention comprises an Rh polypeptide or antigenic fragment thereof. As would be known to the person skilled in the art, Rh polypeptides belong to the family of reticulocyte binding-like proteins in *Plasmodium* spp. that are important for invasion of erythrocytes by merozoites. In *Plasmodium falciparum*, the Rh polypeptide family includes pfRh1 (e.g., PlasmoDB accession PFD0110w (www.plasmodb.org); Genbank accession AF533700; AF411933; AF411930), pfRh2a (e.g., PlasmoDB accession PF13_0198; Genbank accession AY138497; AY138498; AY138499), pfRh2b (e.g., PlasmoDB accession MAL13P1.176; Genbank accession AY138500; AY138501; AY138502; AY138503), pfRh4 (e.g., PlasmoDB PFD1150c; Genbank accession AF432854; AF420309), and pfRh5 (e.g., PlasmoDB PFD1145c; Genbank accession XP_001351544). Further details of Rh polypeptides and antigenic fragments thereof are provided above.

In another embodiment, the composition of the invention comprises an EBA polypeptide or antigenic fragment thereof. As would be understood in the art, EBA polypeptides belong to the *Plasmodium* erythrocyte binding-like (ebl) protein family which have also been shown to be important in merozoite invasion of erythrocytes. In *Plasmodium falciparum*, the EBA polypeptide family includes EBA-175 (e.g., PlasmoDB accession MAL7P1.176; Genbank accession XP_001349207), EBA-181 (e.g., PlasmoDB accession PFA0125c; Genbank accession ACN62280), EBA-165 (e.g., PlasmoDB accession PFD1155w; Genbank accession XP_001351546), and EBA-140 (e.g., PlasmoDB accession MAL13P1.60; Genbank accession XP_001349859). Further details of EBA polypeptides and antigenic fragments thereof are provided above.

A composition of the invention typically comprises a pharmaceutically acceptable carrier. Such carriers include any excipient that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose, trehalose, lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier.

The pH of the composition is preferably between 6 and 8, preferably about 7. The pH may be maintained by the use of a buffer. A phosphate buffer is typical. The composition may be sterile and/or pyrogen-free. The composition may be isotonic with respect to humans. Compositions may include sodium salts (e.g. sodium chloride) to give tonicity. A concentration of 10+/−2 mg/ml NaCl is typical. Compositions may also comprise a detergent e.g. a Tween (polysorbate), such as Tween 80. Detergents are generally present at low levels e.g. <0.01%.

Compositions may comprise a sugar alcohol (e.g. mannitol) or a disaccharide (e.g. sucrose or trehalose) e.g. at around 15-30 mg/ml (e.g. 25 mg/ml), particularly if they are to be lyophilised or if they include material which has been reconstituted from lyophilised material. The pH of a composition for lyophilisation may be adjusted to around 6.1 prior to lyophilisation.

The composition may further comprise an antimalarial that is useful for the treatment of Plasmodial infection. Preferred antimalarials for use in the compositions include the chloroquine phosphate, proguanil, primaquine, doxycycline, mefloquine, clindamycin, halofantrine, quinine sulphate, quinine dihydrochloride, gluconate, primaquine phosphate and sulfadoxine.

The compositions of the invention may also comprise one or more immunoregulatory agents. Preferably, one or more of the immunoregulatory agents include(s) an adjuvant. The adjuvant may be selected from one or more of the group consisting of a TH1 adjuvant and TH2 adjuvant, further discussed below.

The immunogenic compositions and vaccines of the present invention may be administered in any suitable form such as a liquid, emulsion, dried powder and/or in a mist through any parenteral route, intravenously, intraperitoneally, intradermally, by scarification, subcutaneously, intramuscularly, or inoculated by a mucosal route, e.g., orally.

The immunogenic compositions and vaccines of the present invention may be administered using a variety of vaccination regimes familiar to the skilled person. In one form of the invention, the vaccine composition may be administered post antimalarial treatment. For example, blood stage parasitaemia may be cleared with Fansidar (25 mg sulfadoxine/0.75 mg pyrimethamine per kg body weight) before each vaccination. In another form of the invention antimalarial (e.g. Fansidar) treatment is given 1 to 2 weeks before the doses (e.g. first and third doses). In another form of the invention antimalarial (e.g. Fansidar) treatment is given before the first dose.

In another form of the invention, 3 doses of vaccine composition (e.g. 0.5 mg adsorbed onto 0.312 g alum in 0.125 mL) is administered in 3 doses, 2 mg per dose to >5 year olds, 1 mg to under 5 year olds, at weeks 0, 4, and 25. In another form of the invention, 3 doses of vaccine composition (e.g. 1 mg per dose) are given subcutaneously at weeks 0, 4, and 26. In another form of the invention, 3 doses of vaccine composition is administered on days 0, 30, and 180 at different doses (e.g. 1 mg; 0.5 mg). In another form of the invention, 3 doses of vaccine composition is administered at 3 to 4 month intervals either intramuscularly or subcutaneously. In another form of the invention 3 doses of vaccine composition is administered subcutaneously on days 0, 30, and about day 180. In another form of the invention, the vaccine composition is administered in 2 doses at 4-week intervals (e.g. 0.55 mL per dose containing 4 µg or 15 µg or 13.3 µg of each antigen). In another form of the invention, 3 doses of the vaccine composition is administered (e.g. 25 µg in 250 µL AS02A adjuvant) intramuscularly in deltoid (in alternating arms) at 0, 1, and 2 months. In another form of the invention 4 doses of the vaccine composition is given (e.g. 50 µg per 0.5 mL dose) on days 0, 28, and 150; and dose 4 given in the following year. In another form of the invention, where the vaccine is a DNA vaccine, the vaccine composition is administered in two doses (e.g. 2 mg on days 0 and 21 (2 intramuscular injections each time, 1 into each deltoid muscle). In another form of the invention, where the vaccine composition comprises an immunogenic molecule covalently linked to another molecule (e.g. *Pseudomonas aeruginosa* toxin A) the composition is administered in 3 doses (e.g. at 1, 8, and 24 weeks).

Screening Assays

The polypeptides of the invention may be employed in a screening process for compounds which activate (agonists) or inhibit (antagonists) the ability of the polypeptide to bind an erythrocyte receptor (receptor binding).

Examples of potential antagonists include antibodies, oligosaccharides and derivatives thereof. A potential antagonist includes a small molecule which binds to the polypeptide of the invention, making it inaccessible to a binding partner of the polypeptide. Examples of small molecules include, but are not limited to, small organic compounds, small peptides or peptide-like molecules. The small molecules may mimic the structure of a binding partner of the polypeptide according to the invention.

Figure 4:
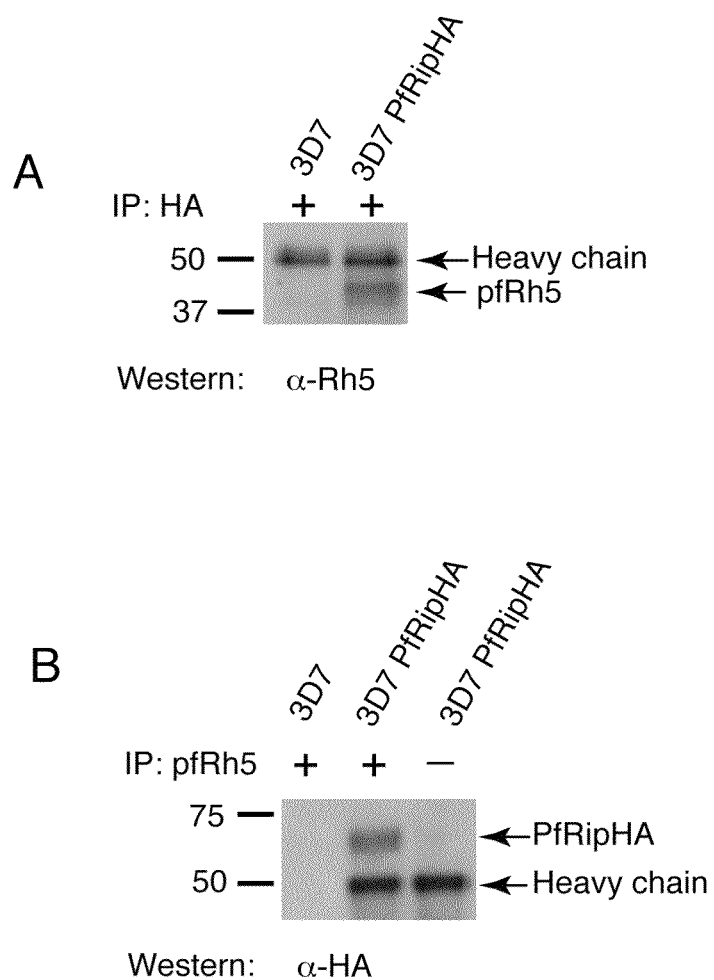
FIG. 4. Reciprocal immunoprecipitation confirm pfRh5 and pfRip form a complex. (A) Immunoblot of protein immunoprecipitated from culture supernatants of 3D7 and 3D7-pfRipHA with anti-HA-Sepharose beads and probed with monoclonal anti-pfRh5 antibody. (B) Immunoprecipitation of culture supernatants from both wt 3D7 and 3D7-pfRipHA parasite lines with monoclonal anti-pfRh5 antibody coupled to Mini-bead.

The invention also comprehends high-throughput screening (HTS) assays to identify compounds that interact with or inhibit the biological activity (i.e., affect receptor binding activity) of a polypeptide of the invention. HTS assays permit screening of large numbers of compounds in an efficient manner. HTS assays are designed to identify "hits" or "lead compounds" having the desired property, from which modifications can be designed to improve the desired property. Chemical modification of the "hit" or "lead compound" is often based on an identifiable structure/activity relationship between the "hit" and the polypeptide.

EXAMPLES

Example 1

Identification of pfRip as Rh5 Complex Partner

Processed 45 kDa pfRh5 from parasite culture supernatant was purified by ion-exchange chromatography. Analysis of pfRH5 by size exclusion chromatography on a Superdex 200 analytical column demonstrated that pfRh5 was eluted as an ~150-200 kDa species (FIG. 1A). Blue native gel electrophoresis confirmed that pfRh5 migrates on a gel as an ~150-200 kDa species (FIG. 1B).

To determine whether pfRh5 is in complex with other molecules or if it forms a homo-oligomer, the protein was incubated with pfRh5 antibody and analysed by size exclusion chromatography. A 300 μl pfRh5-containing fraction isolated from culture supernatant was loaded onto a Superdex 200 analytical column and eluted with PBS (FIG. 2A). An identical 300 μl sample was pre-incubated with 25 μg monoclonal pfRh5 antibody at room temperature for 15 minutes and then on ice for 2 hours before loading onto being loaded onto a Superdex 200 analytical column and eluted with PBS. The pfRh5 eluted as an ~300 kDa species (FIG. 2B) indicating one antibody molecule bound to the 150-200 kDa pfRh5-containing species. This suggested that the 45 kDa pfRh5 fragment is in complex with other molecules rather than forming a homo-oligomer.

PfRh5 complex purified from culture supernatant of Rh5HA parasite line by anti-HA affinity resin was subjected to trypsin digestion in solution and the resulting peptides analysed by mass spectrometry (LC-MS/MS) and identified by searching databases (Table 2). The results show that PfRh5 binds pfRip (SEQ ID NO:2).

TABLE 2

Mass spectrometry identified PfRip as pfRh5 complex partner.

| Protein name | Peptide position | Peptide sequence |
|---|---|---|
| pfRh5 | 187-197 | (K)HLSYNSIYHK(S) (SEQ ID NO: 29) |
| | 212-221 | (K)KINETYDKVK(S) (SEQ ID NO: 30) |
| | 237-247 | (K)KLEHPYDINNK(N) (SEQ ID NO: 31) |
| | 303-310 | (K)MMDEYNTK(K) (SEQ ID NO: 32) |
| | 358-366 | (R)YHYDEYIHK(L) (SEQ ID NO: 33) |
| | 437-443 | (K)IIQDKIK(L) (SEQ ID NO: 34) |
| PfRip | 93-100 | (K)ScDYFISK(E) (SEQ ID NO: 5) |
| | 101-114 | (K)EYNSSDKTNQIcYK(K) (SEQ ID NO: 6) |
| | 699-708 | (K)LIcQcEEGYK(N) (SEQ ID NO: 7) |
| | 760-769 | (K)MEDGINcIAK(N) (SEQ ID NO: 8) |
| | 963-972 | (K)INcTcKENYK(N) (SEQ ID NO: 9) |

Example 2

Shedding of pfRip into Culture Supernatant

A single Strep-tag and triple Haemaglutinin (HA) tag were added to the C-terminus of pfRip by 3'-single homologous cross-over recombination (FIG. 3A). Immunoblotting of saponin pellet and HA-tagged protein purified from culture supernatant of pfRipHA line with anti-HA antibody demonstrated that PfRip was processed and shed to culture supernatant (FIG. 3B). PfRipHA was also analysed by SDS-PAGE under reducing and non-reducing conditions and transferred to nitrocellulose membrane. Immunobloting with anti-HA antibody showed that the processed C-terminal fragment migrates similarly under both reducing and non-reducing condition, suggesting that N-terminal and C-terminal of pfRip is not linked by any disulphide bond after processing (FIG. 3C).

Example 3

Immunoprecipitation of pfRip

Culture supernatants from both wt 3D7 and 3D7-pfRipHA parasite lines were immunoprecipitated with anti-HA-Sepharose bead. Bound materials were separated by SDS-PAGE, transferred to nitrocellulose membrane to probe for pfRh5 using monoclonal anti-pfRh5 antibody (clone 2F1). Detection of pfRh5 in the bound material only from 3D7- pfRipHA line indicated that pfRh5 was specifically co-immunoprecipitated with pfRipHA (FIG. 4A).

Culture supernatants from both wt 3D7 and 3D7-pfRipHA parasite lines were immunoprecipitated with monoclonal anti-pfRh5 antibody coupled to Mini-bead, and culture supernatant of 3D7-pfRipHA parasites was incubated with just Mini-bead as additional control. Bound materials were separated by SDS-PAGE, transferred to nitrocellulose membrane to probe for pfRipHA using anti-HA antibody (FIG. 4B). Detection of pfRipHA in the bound material only from 3D7-pfRipHA parasite line immunoprecipitated with anti-pfRh5-Mini-bead indicated that pfRip was specifically co-immunoprecipitated with pfRh5.

Example 4

Expression of pfRh5 and pfRip in Life-Cycle of *P. Falciparum*

Figure 5:
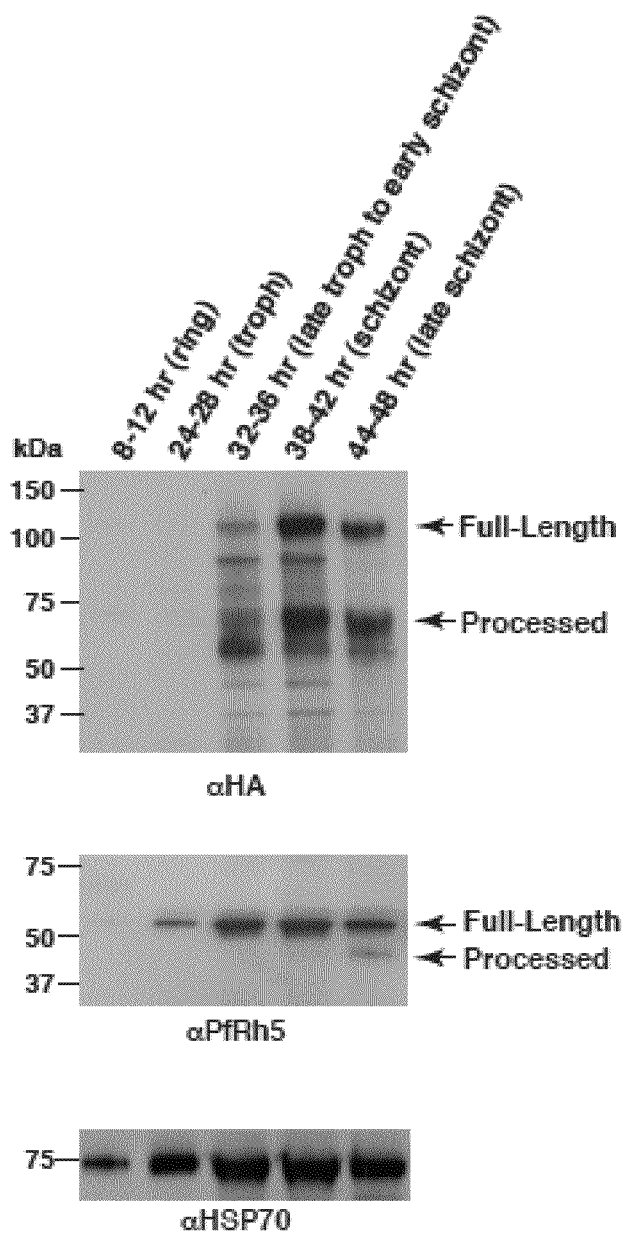
FIG. 5. Both pfRh5 and pfRip express at late life cycle of parasite development. Immunoblot of saponin pellets obtained from triple synchronized pfRipHA parasite culture probed with monoclonal anti-HA antibody, and then stripped and probed with antibodies to pfRh5 and pfhsp70.

A 30 ml-dish of triple synchronized pfRipHA parasite culture (the third synchronization was done when the parasites were in the 8-12 hours ring stage) was distributed into six 5-ml dishes. One dish of culture was harvested for preparing saponin pellet immediately after the third synchronization. The second dish was harvested 16 hr later, the third dish another 8 hr later and subsequent dishes every 6 hr later until the end of schizogony. The saponin pellets prepared from the harvested parasites were separated by SDS-PAGE and transferred to nitrocellulose membrane. The membrane was firstly probed with monoclonal anti-HA antibody for pfRipHA and then stripped to probe for pfRh5 and pfhsp70. Both pfRh5 and pfRip were shown to be expressed at late life cycle stage of parasite development (FIG. 5).

Example 5

Generation of Recombinant pfRip-791-900 and pfRip-238-368

To generate recombinant fragment of pfRip-791-900 (amino acid 791 to 900), oligonucleotides 5' C GCTAGCCATATGAATGAAGAAACAGATATTGTAAA ATG 3' (SEQ ID NO:40) and 5' CGA GGATCCCTAATCTTCTAAAACACATTTTCC 3' (SEQ ID NO:41) were used to PCR amplify the fragment from genomic DNA prepared from 3D7 parasite. The resulting PCR fragment was then cloned into pET14b vector with NdeI and BamHI site, transformed into BL21 RIL *E. coli* strain for expressing recombinant pfRip-791-900 as a hexa-His-tagged protein. The His-tagged protein was purified from soluble lysate of bacteria cells by Ni-resin affinity purification followed by gel-filtration chromatography on Superdex 75 column.

The construct for producing the recombinant fragment of pfRip-238-368 (amino acid 238 to 368) was made by synthesizing codon-optimized DNA sequence coding for pfRip amino acid sequence 238 to 368 and cloned into pET28a vector with NheI and BamHI sites. The construct was then transformed into BL21 RIL *E. coli* strain and produced hexa-His-tagged protein as inclusion body. The protein solubilised from the inclusion body was refolded, purified by Ni-resin affinity column.

Example 6

Production of Antibodies and Western Blot Analysis

The diagram in FIG. 6A shows the region of pfRip that was produced as recombinant protein. Coomassie blue stain of Ni-resin and gel-filtration column purified recombinant protein in shown in FIG. 6B. Immunoblot analysis of native pfRip probed with antibodies raised against recombinant protein is shown in FIG. 6C.

Figure 7:
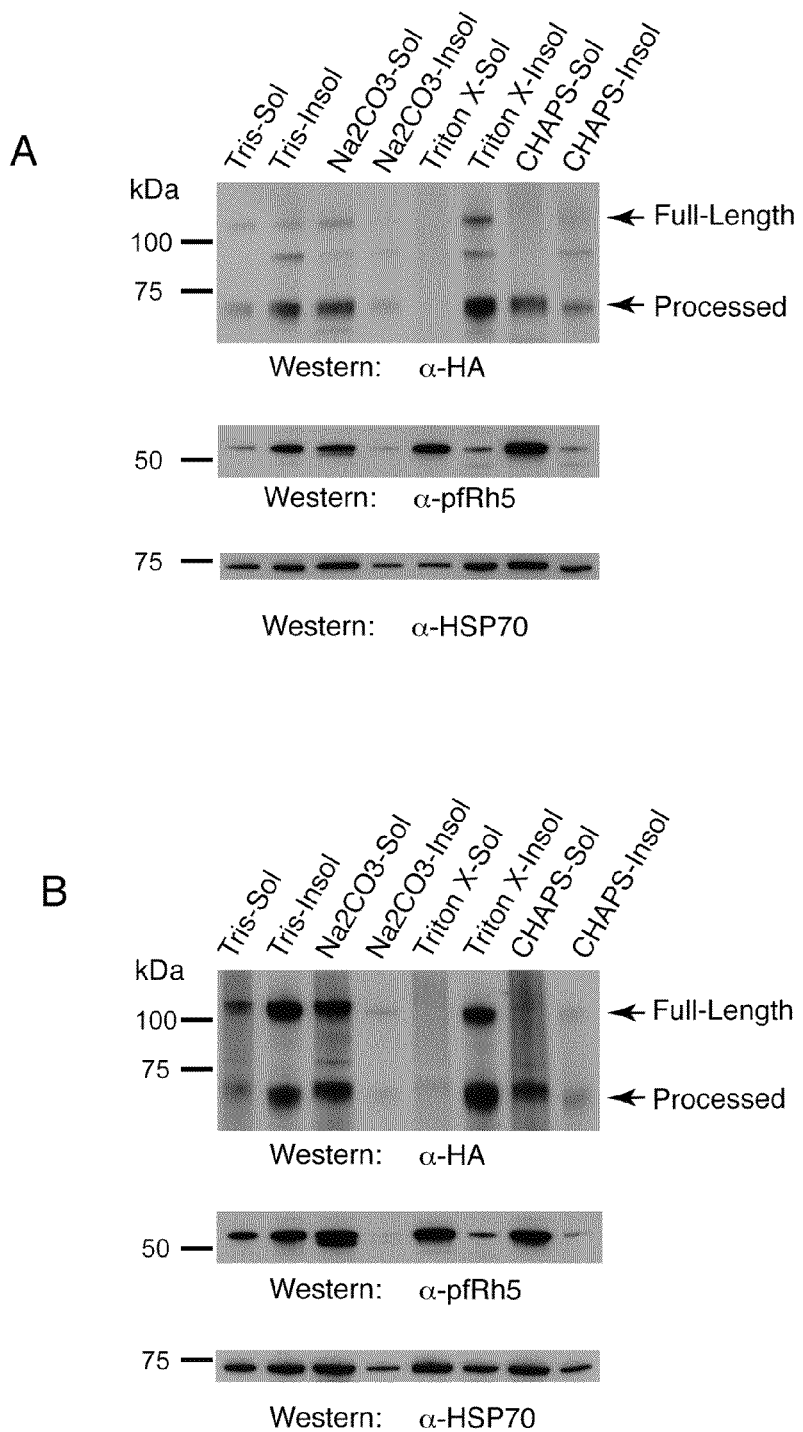
FIG. 7. PfRip is a peripheral membrane protein and carries its complex partner pfRh5 onto the surface of merozoites. (A) Immunoblot of soluble and insoluble fractions from pellet prepared by hypotonically lysis of the late schitzont stage PfRipHA parasite infected red blood cells. (B) Immunoblot of saponin pellet prepared from the late schitzont stage pfRipHA parasite-infected red blood cells.

PfRipHA parasite (late schitzont stage)-infected red blood cells were hypotonically lysed with water, centrifuged and pellet fraction washed with PBS twice. The pellet fraction was then divided into four eppendorfs and incubated on ice for 2 hours with 10 mM Tris/pH 8.0; 100 mM sodium carbonate/pH 11.5; 2% Triton X100 and 2% CHAPS in 50 mM Tris/pH8.0, 1 mM EDTA and 100 mM sodium chloride respectively. The samples were centrifuged to separate soluble and insoluble fractions. The insoluble fraction was washed twice with PBS and analysed by western blot together with the soluble fraction (FIG. 7A). Saponin pellet prepared from the pfRipHA parasite (late schitzont stage)-infected red blood cells were subjected to the same analyses described above (FIG. 7B). The results demonstrate that PfRip is a peripheral membrane protein and carries its complex partner pfRh5 onto the surface of merozoites.

Example 7

Inhibition of Parasite Attachment and Growth

Figure 8:
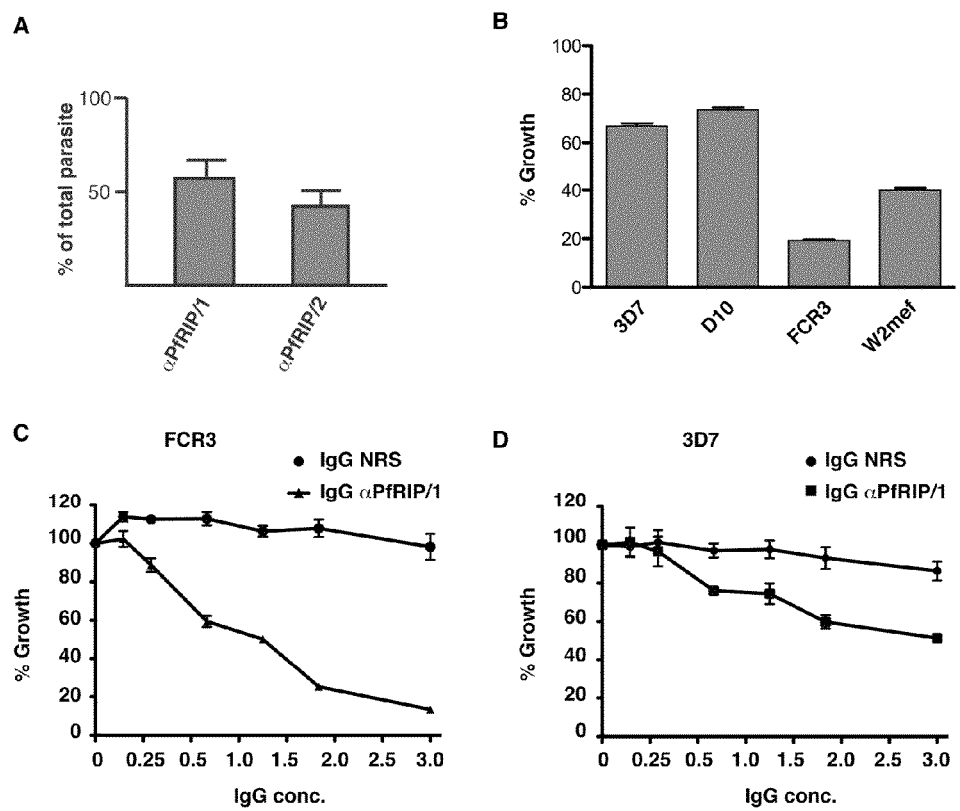
FIG. 8. (A) Pre-incubation of purified merozoites with Protein-A purified rabbit polyclonal antibodies (R1155 & R1156 at 2 mg/ml) raised against recombinant pfRip for 2 minutes at 37° C. inhibited merozoites attachment to uninfected red blood cells by 40-55%. (B) Growth Inhibition assay (GIA) for different strains of *P. falciparum* using anti-PfRIP-1 IgG antibodies. (C) Titration of IgG anti-PfRIP-1 antibodies with FCR3. (D) Titration of IgG anti-PfRIP-1 antibodies with 3D7.

Pre-incubation of purified merozoites with Protein-A purified rabbit polyclonal antibodies [R1155 (αpfRIP/1) and R1156 (αpfRJP/2) at 2 mg/ml] raised against recombinant pfRip for 2 minutes at 37° C. inhibited merozoites attachment to uninfected red blood cells by 40-55% (FIG. 8A). Protein-A purified antibodies from normal serum were used as control (NRS). Growth inhibition assay (GIA) for *P. falciparum* strains 3D7, D10, FCR3 and W2mef are shown in FIG. 8B. Shown in FIG. 8C is the Titration of IgG anti-PfRIP-1 antibodies with FCR3. The titration of IgG anti-PfRIP-1 antibodies with 3D7 is shown in FIG. 8D.

Figure 9:
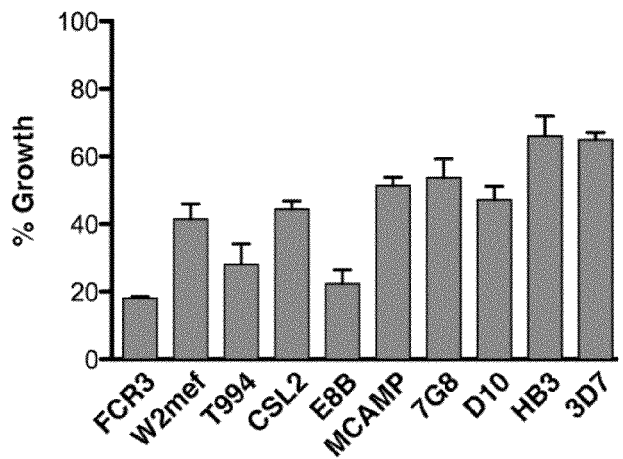
FIG. 9. Antibodies to a C-terminal region of PfRipr inhibit attachment of merozoites to erythrocytes and parasite growth. (A) Anti-PfRipr/1 antibodies inhibit invasion of *P. falciparum* strains into erythrocytes. Shown are growth inhibition assays of the parasite strains FCR3, W2mef, T994, CSL2, EBB, MCAMP, 7G8, D10, HB3 and 3D7. The graph represents three independent experiments done in triplicate with each normalised to the negative control (Protein A purified IgG from normal rabbit serum). The error bars represent standard error of the mean of the three independent experiments. (B) GIA assay using different combinations of antibodies on invasion of the 3D7 strain. Shown are IgG antibodies: αPfRIP/1, αPfRIP/2, αPfRIP/1+αEBA-175, αPfRIP/1+αPfRh4, αPfRIP/1+αPfRh2a/b and αPfRIP/1+αPfRh2a/b+αPfRh4 (shown as αPfRIP/1+αP fRh2a/b/PfRh4).
Figure 9:
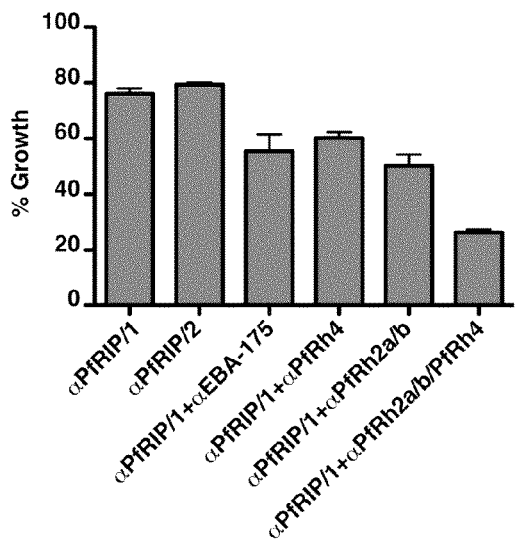

The present inventors tested the anti-PfRIP/1 and anti-PfRIP/2 antibodies (αPfRIP/1 and 2 antibodies) for their ability to block parasite growth (growth inhibition assays, GIA) using the *P. falciparum* strains FCR3, W2mef, T994, CSL2, E8B, MCAMP, 7G8, D10, HB3, and 3D7 (FIG. 9A). Significantly, the FCR3 strain was inhibited to 80% whilst in comparison 3D7 was inhibited to 35% with αPfRIP/1 at 2 mg/ml (FIG. 9A). The inhibition observed for 3D7 was comparable to that observed for other antibodies raised to regions of the PfRh or EBL protein families. Similar results were observed for 3D7 using the αPfRIP/2 (data not shown). The level of growth inhibition activity observed with the αPfRIP/1 and αPfRIP/2 antibodies for 3D7 parasites was similar to that observed in the attachment assays demonstrating that the inhibitory effect was occurring at merozoite invasion rather than during the growth of the parasite (FIG. 8A).

Among other *P. falciparum* strains tested αPfRIP/1 antibody exhibited significantly higher inhibitory activity for those that invade erythrocyte preferentially using sialic acid-dependent receptors (ie. glycophorins), which includes FCR3, W2mef, T994, CSL2 and E8B. The αPfRIP/1 antibody was titrated in GIAs in comparison with IgG from normal serum for both FCR3 and 3D7 parasite strains. Growth of FCR3, a parasite that invades preferentially by sialic acid-dependent pathways, was almost completely abolished at 3 mg/ml and significant inhibition still remained even at 1 mg/ml (40%). In comparison, the 3D7 parasite strain, which can efficiently use sialic acid-independent invasion pathways primarily by using the ligand PfRh4 and complement receptor 1, was inhibited at significantly lower levels with 40% at 3 mg/ml and this decreased to 25% at 1 mg/ml of antibody. This suggests that the PfRIP/PfRh5 complex may be more functionally important in *P. falciparum* strains that efficiently use sialic acid-dependent invasion pathways.

Figure 6:
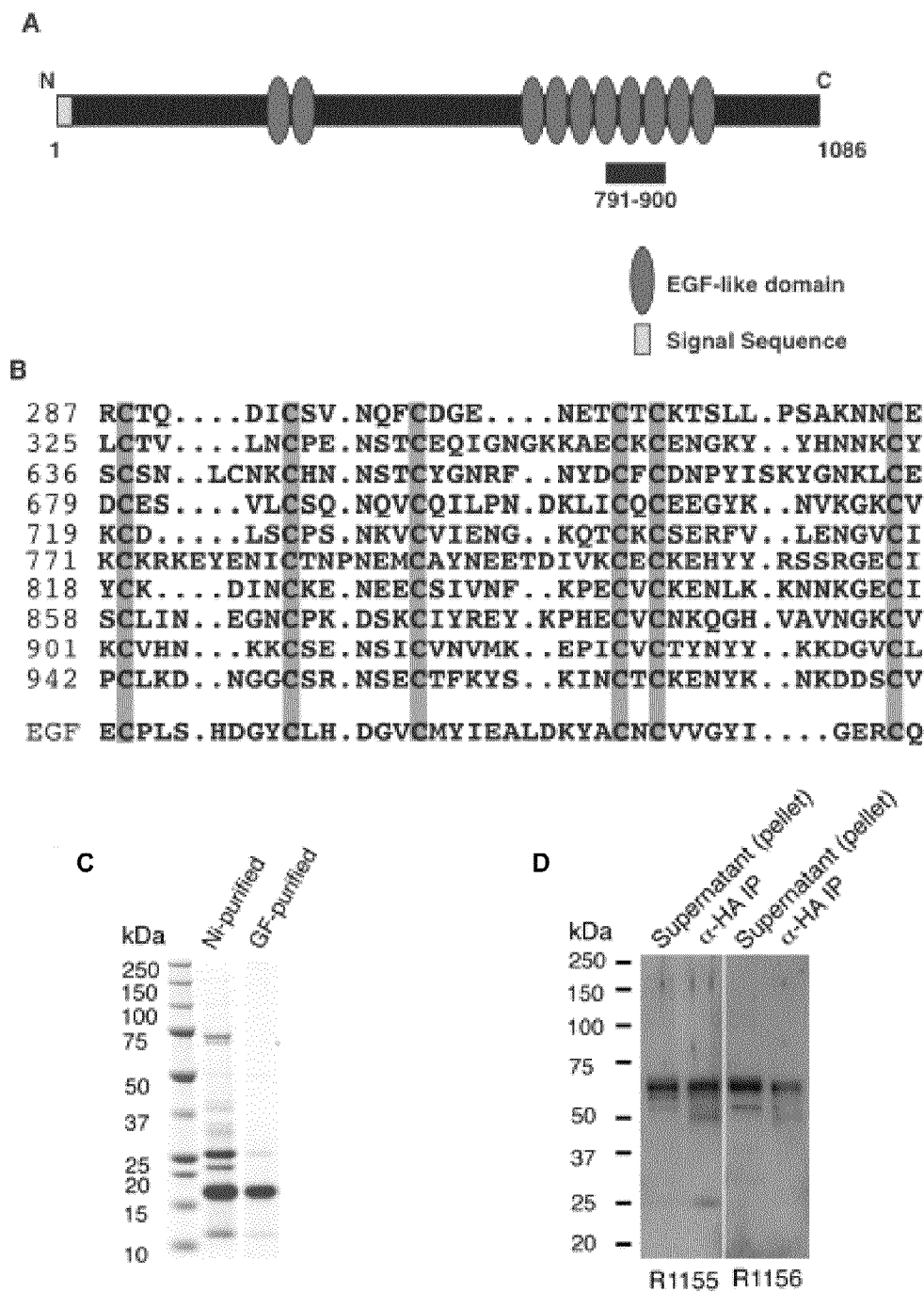
FIG. 6. The domain structure and expression of PfRip in *P. falciparum*. (A) The domain structure of the PfRip protein. PfRip is 1,086 amino acids with a signal sequence and 10 EGF-like domains. Two are grouped in the N-terminus with a further eight clustered towards the C-terminus. The EGF-like domains are shown as the elipse-shaped objects. (B) A lineup of the ten EGF-like domains showing the conserved cysteine residues that define these domains. The amino acid residues in PfRip are shown at the left. Also in the alignment is the epidermal growth factor domain. (C) Expression of amino acid residues 791-900 of PfRip as a recombinant protein in *E. coli*. Shown are the protein eluate after Ni-chelate chromatography (lane 1) and size exclusion chromatography (lane 2). (D) Antibodies raised to the PfRip recombinant protein react with PfRip in schizont preparations of *P. falciparum*. Shown are two immunoblots probed with antibodies raised in two rabbits (anti-PfRip/1 and anti-PfRip/2).

The region of PfRIP to which the anti-PfRIP antibodies were raised was from the 3D7 strain of *P. falciparum*; however, this domain does not show any polymorphisms in other strains that have been sequenced (http://plasmodb.org/). Also, the present inventors did not observe any cross-reactivity of the antibodies with other proteins that contain EGF-like domains such as MSP1. This was not surprising as the only conserved amino acids was the six cytseine residues that define each EGF-like domain (FIG. 6). Therefore the differences in inhibition observed in GIA with the various strains was unlikely due to cross reactivity with other proteins containing EGF-like domains or polymorphisms within this region of PfRIP. It is more likely reflects the reliance of them on the PfRh5/PfRIP complex to mediate a specific invasion pathway in comparison to the function of other members of the PfRh and EBA protein families. To test this we used a combination of IgG antibodies raised to PfRIP, EBA-175, PfRh4, PfRh2a and PfRh2b to determine if they increased the level of inhibition in GIAs for 3D7 parasites (FIG. 9B). Both αPfRIP/1 and αPfRIP/2 antibodies inhibited 3D7 parasites to 25 and 20% respectively (FIG. 9B), similar to our previous experiment (FIG. 8B). The combination of αPfRIP/1 with αEBA-175 antibodies showed an additive inhibition of 45% (FIG. 9B). This was a similar result to that observed for the combination of αPfRIP/1 with αPfRh4 or αPfRh2a/b antibodies. Significantly, a combination of αPfRIP/1, αPfRh2a/b and αPfRh4 showed a much higher level of inhibition (74%). This additive effect was consistent with parasites using multiple invasion pathways to gain entry to the erythrocyte.

Example 8

Identification of the pfRh2a/b Erythrocyte Binding Site

Figure 10:
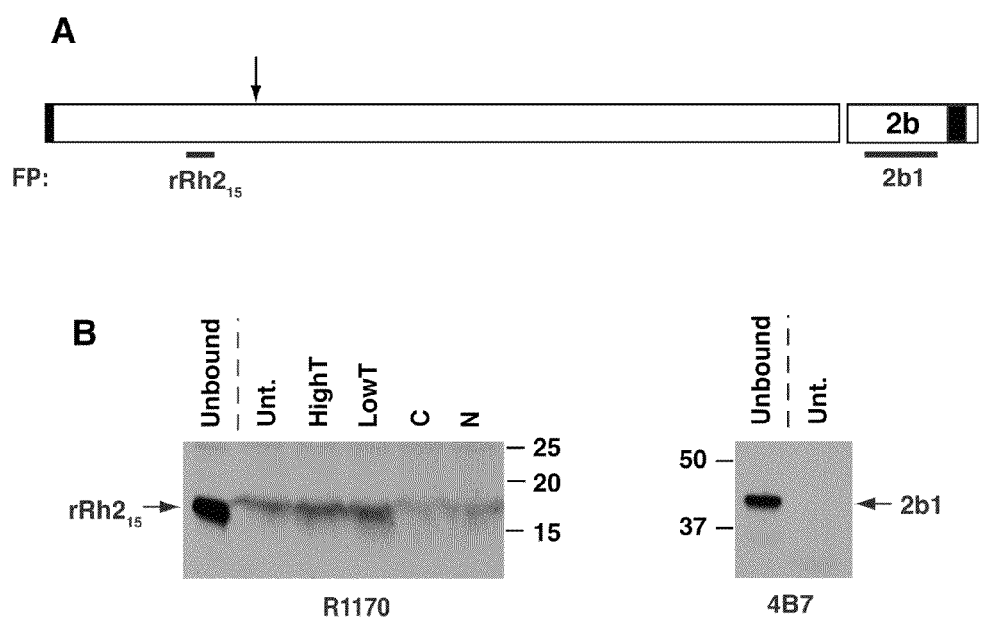
FIG. 10. Recombinant $rRh2_{15}$ binds erythrocytes. (A) Schematic diagram of the PfRh2 protein showing the location of the $rRh2_{15}$ and 2b1 fusion proteins. The $rRh2_{15}$ is located within the 85 kDa binding domain of PfRh2. The processing event leading to the 85 kDa product is indicated by the arrow. The 2b1 fusion protein is from a Rh2b unique region at the C-terminus of the protein. The regions of the protein in black at the N and C-termini represent the signal sequence and transmembrane domains respectively. (B) Recombinant $rRh2_{15}$ was bound to untreated (Unt.), Low trypsin (LowT; 0.067 mg/ml), High Trypsin (HighT; 1 mg/ml), neuraminidase (N) or chymotrypsin-treated (C) erythrocytes. Bound proteins were eluted with 1.5M NaCl, separated on SDS-PAGE gels, Western blotted and probed with an antibody (R1170) to the $rRh2_{15}$ fusion protein. Recombinant $rRh2_{15}$ binding to erythrocytes was partially sensitive to neuraminidase and chymotrypsin, but resistant to both Low and High Trypsin concentrations. Unbound proteins removed from the Untreated erythrocytes are also shown. The 2b1 fusion protein was bound to untreated erythrocytes. Bound proteins were eluted with 1.5M NaCl, separated on SDS-PAGE gels, Western blotted and probed with the 4B7 antibody raised to the 2b1 fusion protein. The 2b1 fusion protein showed no binding to Untreated erythrocytes but was clearly present in the Unbound fraction.

To confirm the 85 kDa PfRh2a and b protein was directly responsible for binding to human erythrocytes recombinant proteins were made of different portions that covered this region. A protein of 15 kDa corresponding to amino acids 446 to 557 of the PfRh2a/b N-terminus (rRh2$_{15}$), expressed as an *E. coli* hexa-His tagged protein, bound to erythrocytes whereas the 2b1 protein from the C-terminal region of PfRh2b showed no detectable binding (FIG. 10). The rRh2$_{15}$ erythrocyte binding was resistant to trypsin treatment but partially sensitive to chymotrypsin and neuraminidase treatment, a pattern of binding observed for the *P. falciparum* expressed 85 kDa protein from culture supernatants.

Figure 11:
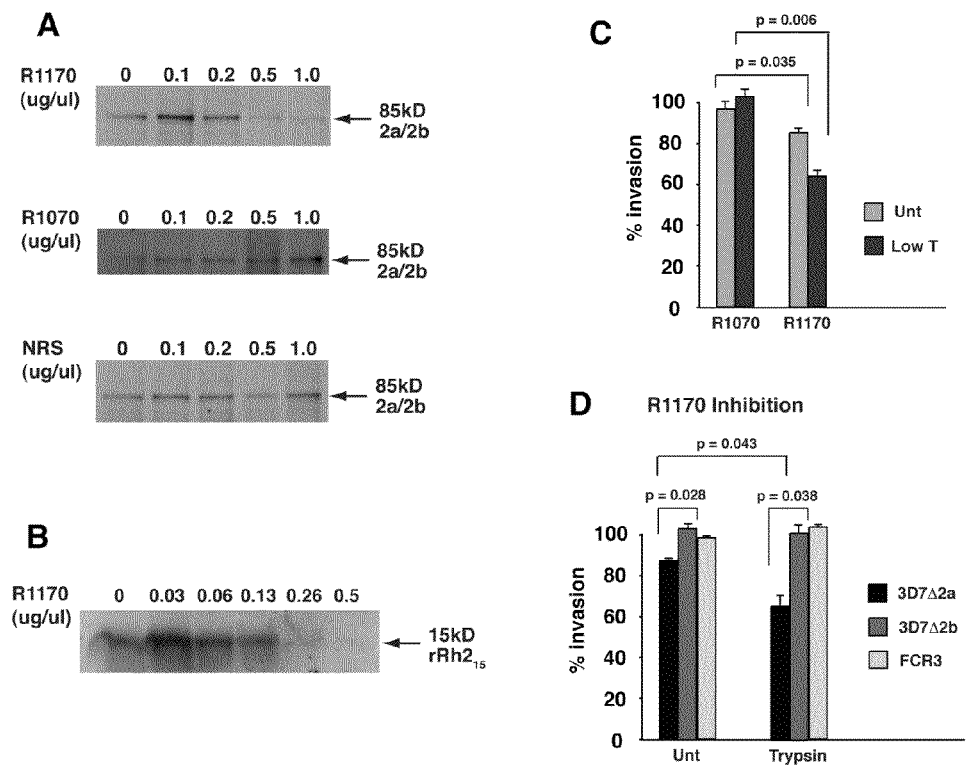
FIG. 11. Antibodies to $rRh2_{15}$ block native PfRh2 binding and invasion. (A) R1170 antibodies made to $rRh2_{15}$ block binding of native PfRh2 to erythrocytes. Protein G-purified R1070, R1170 or normal rabbit serum antibodies at final concentrations from 0.1 to 1.0 µg/µl were preincubated with 3D7 culture supernatant before adding Untreated erythrocytes. Bound proteins were eluted with 1.5M NaCl, separated on SDS-PAGE gels, Western blotted and probed with an antibody (6F12) to the 85 kDa PfRh2 binding domain. Only antibodies to the $rRh2_{15}$ (R1170) block binding of native PfRh2 to erythrocytes. Antibodies to another region of the 85 kDa binding domain and normal rabbit serum antibodies do not block binding. B) R1170 antibodies block binding of $rRh2_{15}$ to erythrocytes. Protein G-purified R1170 antibodies at final concentrations from 0.03 to 0.5 µg/µl were pre-incubated with 0.5 µg $rRh2_{15}$ fusion protein before adding Untreated erythrocytes. Bound proteins were eluted with 1.5 M NaCl, separated by SDS-PAGE, Western blotted and probed with Protein G-purified R1170. (C) Antibodies to rRh2$_{15}$ block invasion of both untreated and Low trypsin-treated erythrocytes. Protein G-purified IgG at 2 mg/ml final concentration from both R1070 and R1170 pre-bleeds and kill bleed sera were added to 3D7 parasites at the trophozoite stage together with target erythrocytes that were untreated or Low trypsin (0.067 mg/ml)-treated. Following reinvasion in the presence of antibodies, cultures were continued to the trophozoite stage, when parasite numbers were determined in order to see the effect of antibodies on invasion. Percent invasion in the absence of antibodies was adjusted to 100% invasion. Experiments were done at least twice in triplicate. Error bars show the standard error of the mean. (D) Antibodies to rRh2$_{15}$ block invasion of PfRh2b but not Rh2a in 3D7 parasites. Protein G-purified IgG from R1170 kill bleed serum at 2 mg/ml final concentration was added to 3D702a (express Rh2b only), 3D7Δ2b (express Rh2a only) and FCR3 (express neither Rh2a nor Rh2b) parasites at the trophozoite stage together with target erythrocytes that were untreated or treated with 0.03 mg/ml Trypsin. Other details of the experiments were the same as in (C) above.

To show that binding of rRh2$_{15}$ to erythrocytes was specific it was determined if IgG antibodies raised to this domain block binding of both the 85 kDa fragment from parasite supernatants and the rRh2$_{15}$ fragment. The antibodies R1170 showed a dose-dependent inhibition of binding of the 85 kDa fragment in contrast to antibodies raised to a second recombinant protein of PfRH2a/b made from the N-terminus and IgG from normal rabbit serum (FIG. 11A). The same R1170 antibodies also blocked binding of the rRh2$_{15}$ recombinant protein in a dose-dependent manner (FIG. 11B). Therefore the erythrocyte-binding domain of PfRh2a and b is located within the region defined by the 15 kDa rRh2$_{15}$ recombinant protein.

Example 9

Antibodies to the PfRh2a/b Binding Site Inhibit Merozoite Invasion

To determine if antibodies to rRh2$_{15}$ (R1170) inhibit invasion they were tested in growth inhibition assays with normal and trypsin-treated erythrocytes. The anti-rRh2$_{15}$ antibodies showed approximately 18% inhibition into normal erythrocytes compared to no inhibition for antibodies to a second fusion protein close to the receptor binding site and this was increased for trypsin-treated cells to 38% (FIG. 11C). The enhancement of inhibition occurred as a result of removal of trypsin-sensitive receptors from erythrocytes thus limiting those available. The PfRh2a/b erythrocyte receptor is trypsin-resistant and removal of other receptors by this treatment increases the potency of these inhibitory antibodies (Duraisingh et al., 2003).

To show that the inhibitory effect was specific and also to determine if it was acting on the function of both PfRh2a and PfRh2b the *P. falciparum* lines in which each gene had been specifically disrupted were used (Duraisingh et al., 2003). For normal erythrocytes anti-rRh2$_{15}$ antibodies inhibited growth at approximately the same level for 3D7Δ2a, which lacks expression of PfRh2a, and the 3D7 parent and this was enhanced for trypsin-treated erythrocytes. In contrast, the *P. falciparum* lines 3D7Δ2b (lacks expression of PfRh2b) and FCR3 (lacks expression of PfRh2a and PfRh2b) were not inhibited (FIG. 11D). Therefore the anti-rRh2$_{15}$ antibodies to the receptor-binding site directly inhibit PfRh2b function but not PfRh2a as it was not functional in 3D7.

Example 10

Inhibition of *P. Falciparum* Invasion of Human Red Blood Cells

Antibodies against a combination of antigens were tested for their ability to inhibit invasion of *P. falciparum* into human red blood cells in vitro.

Rabbits were immunized with a total of 225 µg protein comprising 75 µg of each the following antigens: EBA175 R3-5 (amino acids 760-1271; SEQ ID NO:36), PfRh2a/b (15 kDa fragment; SEQ ID NO:12) and PfRIPr (791-900; SEQ ID NO:3).

Blood was taken and IgG fraction purified 34 days following a single immunization with the three antigens. Serial dilutions were made of the IgG with 2 mg/ml starting concentration. Antibodies were incubated together with *P. falciparum* parasites 3D7. Control Ab was non-immune rabbit IgG. Percentage invasion is calculated as 100×(mean invasion (triplicate wells) of control IgG/test IgG).

Figure 12:
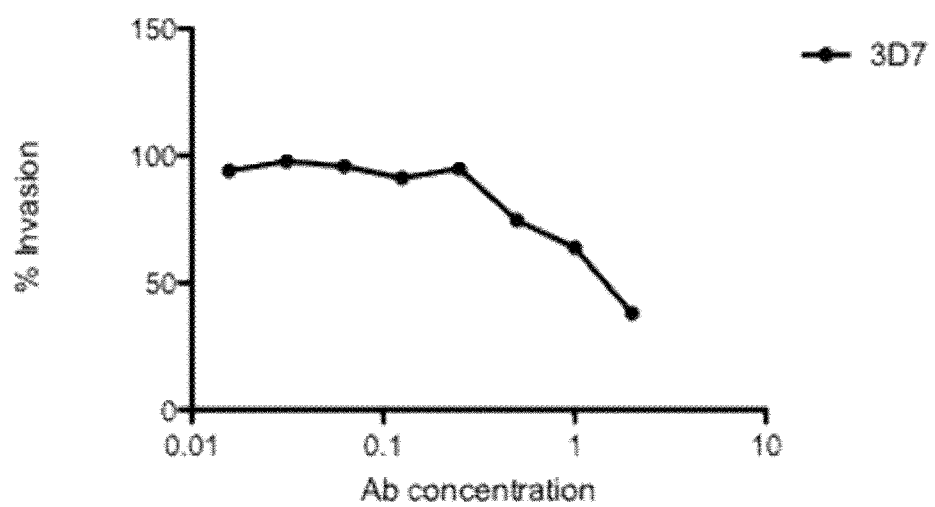
FIG. 12. Antibodies against a combination of antigens inhibit invasion of *P. falciparum* into human red blood cells in vitro. Percentage invasion is calculated as 100×(mean invasion (triplicate wells) of control IgG/test IgG).

FIG. 12 shows titration of the growth inhibitory response against wild type 3D7 parasites, with a reduction of invasion of 62% at 2 mg/ml compared to non-immune serum.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

All publications discussed and/or referenced herein are incorporated herein in their entirety.

The present application claims priority from U.S. 61/411, 598 and U.S. 61/435,602, the entire contents of which are incorporated herein by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to

REFERENCES

Breman et al. (2004) Am J Trop Med Hyg, 71 Suppl 2:1-15.
Duraisingh et al. (2003) EMBO J, 22:1047-1057.
George, et al. (2003) Protein Engineering, 15:871-879.
Harayama (1998) Trends Biotech, 16; 76-82.
Hay et al. (2004) Lancet Infect Dis, 4:327-336.
Hoffmann et al. (2002) J Infect Dis, 185:1155-1164.
Needleman and Wunsch (1970) J Mol Biol, 48:443-453.
Ohta et al. (1998) Tokai J Exp Clin Med, 23:85.
Paolicelli et al. (2010) Nanomedicine, 5:843-853.
Rammensee (1995) Curr Opin Immunol, 7:85-96.
Singh et al. (2010) PLos One, 5:e9435.
Snow et al. (2004) Am J Trop Med Hyg, 71 Suppl 2:16-24.
Sun et al. (2009) Vaccine 27:1787-1796.
Wang et al. (2001) Proc Natl Acad Sci USA, 98:10817-10822.

the present invention as it existed before the priority date of each claim of this application.

The invention claimed is:

1. A recombinant combination vaccine composition comprising an isolated and/or recombinant first and second polypeptide, wherein the first polypeptide comprises an amino acid sequence comprising SEQ ID NO: 2 or an antigenic fragment thereof, or an amino acid sequence of SEQ ID NO: 2 comprising one or more point mutations selected from the group consisting of:

N at amino acid position 144 replaced with K,
V at amino acid position 190 replaced with A,
H at amino acid position 511 replaced with R,
L at amino acid position 673 replaced with V,
A at amino acid position 755 replaced with G,
Y at amino acid position 985 replaced with N, and
I at amino acid position 1039 replaced with M;

and wherein said second polypeptide consists of SEQ ID NO: 36 or consists of SEQ ID NO: 36 having one or more point mutations selected from the group consisting of:

S at amino acid position 9 replaced with N,
E at amino acid position 164 replaced with K,
K at amino acid position 173 replaced with E,
E at amino acid position 299 replaced with V, and
G at amino acid position 341 replaced with D;

and an immunologically effective amount of an adjuvant.

2. The composition of claim 1, wherein the composition further comprises a Rh polypeptide.

3. The composition of claim 2, wherein the Rh polypeptide comprises:
   i) an amino acid sequence selected from any one of SEQ ID NOs:10 to 28, or
   ii) an amino acid sequence which is at least 70% identical to any one of SEQ ID NOs:10 to 28.

4. The composition of claim 2, wherein the Rh polypeptide is an Rh1 polypeptide selected from the group consisting of:
   i) an amino acid sequence as set forth in SEQ ID NO:10, or
   ii) an amino acid sequence which is at least 70% identical to SEQ ID NO:10.

5. The composition of claim 2, wherein the Rh polypeptide is an Rh2 polypeptide selected from the group consisting of:
   i) an amino acid sequence selected from any one of SEQ ID NOs:11 to 14, or
   ii) an amino acid sequence which is at least 70% identical to any one or more of SEQ ID NOs:11 to 14.

6. The composition of claim 2, wherein the Rh polypeptide is an Rh4 polypeptide selected from the group consisting of:
   i) an amino acid sequence as set forth in SEQ ID NO:15 or SEQ ID NO:16, or
   ii) an amino acid sequence which is at least 70% identical to SEQ ID NO: 15 or SEQ ID NO:16.

7. The composition of claim 2, wherein the Rh polypeptide is an Rh5 polypeptide selected from the group consisting of:
   i) an amino acid sequence selected from any one of SEQ ID NOs:17 to 28, or
   ii) an amino acid sequence which is at least 70% identical to any one of SEQ ID NOs:17 to 28, or
   iii) or an amino acid sequence of SEQ ID NO: 18 comprising one or more point mutations selected from the group consisting of:

E at amino acid position 25 replaced with K,
Y at amino acid position 124 replaced with H,
H at amino acid position 125 replaced with N,
S at amino acid position 174 replaced with Y,
C at amino acid position 180 replaced with Y, I at amino acid position 181 replaced with K or R,
N at amino acid position 324 replaced with Y or D,
Y at amino acid position 335 replaced with F,
E at amino acid position 339 replaced with D,
V at amino acid position 348 replaced with I,
I at amino acid position 384 replaced with V,
I at amino acid position 387 replaced with M, and
K at amino acid position 406 replaced with N.

8. The composition of claim 1, wherein the antigenic fragment of SEQ ID NO: 2 consists of the amino acid sequence of SEQ ID NO:3.

9. The composition of claim 1, wherein at least one of the polypeptides in the composition is a fusion protein comprising at least one other polypeptide sequence.

10. The composition of claim 1, wherein the antigenic fragment of the first polypeptide consists of the amino acid sequence of any one of SEQ ID NOs: 3, 7, 8, or 9.

* * * * *

SEQUENCE LISTING

```
<160> NUMBER OF SEQ ID NOS: 57

<210> SEQ ID NO 1
<211> LENGTH: 3261
<212> TYPE: DNA
<213> ORGANISM: Plasmodium falciparum

<400> SEQUENCE: 1
atgttcagaa ttttttttac ccttcttata ataatattaa tcaagaaaac atcggcaatt      60
gatttaatag aaggaatttt ttatgaaaaa aatgaaatag ataaattaac attttctctc     120
gatcatagag ttagagataa tttaaaaaca gatttgattt taaataataa tggggaaaat     180
gattatgctt atttaaacaa atacgtttat actatattaa atcgtgattc aacagaaaaa     240
attaaaacat ttttttctca taataaagac atgaaatcat gtgattattt tatatcaaaa     300
gaatataatt caagtgataa aacaaatcaa atatgttata aaaaaacatt ttgcggagta     360
gtaataccaa atagtgaaga aataaaaaca aataaaataa caaatgacaa actttattgt     420
gcacatttca attctacaca tataatcatt tattacatat cacaaccact tttattagaa     480
cctcatgttg tttatgaaga aacatttttt gaaaaggaa aaaatgatca aattaattgc     540
caaggtatgt atatatctct aagatctgta catgtacata cacacaatgc tatattacaa     600
caagaaacac ttacatatat taaaaattta tgtgacggaa aaaacaattg taaattcgat     660
tttgattcaa taaaatatga aaataaatca cttactcatt atttgttttt tattaatata     720
caatatcaat gcataagtcc tctgaatcta caggaaaatg aaatgtgtga cgtatataat     780
gatgatacac ataaagcaac atgcaaatat ggttttaata aaatagaatt attaaaaaat     840
gtttgtgaag aaaattatag atgtacacaa gatatatgtt cagtaaatca attttgtgac     900
ggagaaaatg aaacatgtac atgcaaaaca tcattattac catcagctaa aaacaattgt     960
gaatacaacg atttatgtac agtttttaaat tgtcctgaaa attccacatg tgaacaaata    1020
ggaaatggga aaaagctga atgtaaatgt gaaaatggta atattatca caataataaa    1080 tgttatacaa aaaatgattt agaattagcc ataaaaatag aaccacataa aaaagaaaaa    1140
ttttataaaa ataatttata tcaaggaaaa gcattaaaac cagaatatat ttttatgcaa    1200
tgtgaaaatg ggttctctat agaagttatt aatgcatatg tatcatgtta tagagtttca    1260
ttcaatctaa acaaattgaa atatgttaca gaatcattaa aaaaaatgtg tgatgggaaa    1320
accaaatgtg cttatggaaa tacaatagat ccaatagatg atttaaatca tcataatata    1380
tgtaataatt ttaatacaat atttaaatat gattatttat gtgtattcaa taatcaaaat    1440
attacttcag ataagaattc acatcttcat tctaatatac catcattata taattcaagt    1500
attctaccag atattaataa atctaaattc catttgattt caagaaatag tcgaaccaac    1560
caatatcctc ataacaatat atccatgcta gaaatacaaa atgaaatatc ctcacacaat    1620
tcaaatcagt ttagtacaga tccacacaca aatagtaata atataaacaa tatgaatatt    1680
```

```
aaaaaggtag aaatcttcag aagtcgtttt tcaagtaaat tacaatgtca aggggggaaaa   1740 ataaatattg ataaagcaat tttaaaaggt ggggaaggat gtaatgattt gcttttgacg   1800
aattctttaa aatcatattg taatgattta tcagaatgtg atattggttt aatataccat   1860
tttgatactt attgtattaa tgatcaatat cttttgtat cttacagctg ctccaattta   1920
tgtaataaat gtcataacaa ttctacatgc tatgggaaca gatttaatta tgattgtttt   1980
tgtgataatc cttatatttc aaaatatgga aataaattat gtaacgtcc aaatgattgt   2040 gaatctgttt tgtgttcaca aaatcaagtt tgtcaaattc ttccaaatga taaattaata   2100
tgtcaatgtg aagaaggata taaaaatgtt aaaggtaaat gtgttccaga caacaaaatgt   2160 gatctttcat gcccatcaaa caaagtttgt gttatcgaaa atggaaaaca acatgtaaaa   2220
tgttcagaac gttttgttct agagaatggt gtgtgtatat gtgctaatga ttataaaatg   2280
gaagatggta ttaattgtat agccaaaaat aaatgtaaaa gaaagaata tgaaaatatt   2340 tgtacaaatc caaatgaaat gtgtgcttat aatgaagaaa cagatattgt aaaatgtgaa   2400
tgtaaagaac attattatag atcatcaaga ggtgaatgta tattaaatga ttattgtaaa   2460
gatattaatt gtaaagaaaa tgaagaatgt tctattgtaa actttaaacc agaatgtgta   2520
tgtaaagaaa atcttaaaaa aataataaaa ggagaatgta tttatgaaaa ctcctgttta   2580
attaatgaag ggaattgtcc aaaagattca aaatgtattt atagagaata taaaccacat   2640
gaatgtgtat gtaataaaca aggtcatgta gctgtcaatg gaaaatgtgt tttagaagat   2700
aaatgtgtac ataataaaaa atgttcagaa aattctatat gtgtaaatgt aatgaataaa   2760
gaaccaatat gtgtatgtac atataattat tataaaaaag atggtgtatg tttaatacaa   2820
aacccttgtc taaaagataa tggaggctgc tctagaaatt cagagtgtac atttaaatat   2880
agtaaaatta attgtacatg taaagaaaat tataaaaata aagatgattc ttgtgtacct   2940
aatacaaatg agtatgatga agttttaca ttccaatata tgacgatgc atctattatt   3000 cttggagcat gtggtatgat cgaattttca tatatatata accaaattat ttggaaaata   3060
aataactcaa aagaatctta cgtattttat tatgattatc caacagcagg taatatagaa   3120
gttcaaatta aaaatgaaat atttcacact attatatatt tgaaaaaaaa aataggcaat   3180
agtgttatct atgatgattt ccaagtagat catcaaacat gtatatatga aaatgtattt   3240
tattatagta atcagaatta g                                              3261
```

<210> SEQ ID NO 2
<211> LENGTH: 1086
<212> TYPE: PRT
<213> ORGANISM: Plasmodium falciparum

<400> SEQUENCE: 2

```
Met Phe Arg Ile Phe Phe Thr Leu Leu Ile Ile Leu Ile Lys Lys
1               5                   10                  15

Thr Ser Ala Ile Asp Leu Ile Glu Gly Ile Phe Tyr Glu Lys Asn Glu
            20                  25                  30

Ile Asp Lys Leu Thr Phe Ser Leu Asp His Arg Val Arg Asp Asn Leu
        35                  40                  45

Lys Thr Asp Leu Ile Leu Asn Asn Asn Gly Glu Asn Asp Tyr Ala Tyr
    50                  55                  60

Leu Asn Lys Tyr Val Tyr Thr Ile Leu Asn Arg Asp Ser Thr Glu Lys
65                  70                  75                  80

Ile Lys Thr Phe Phe Ser His Asn Lys Asp Met Lys Ser Cys Asp Tyr
                85                  90                  95
```

```
Phe Ile Ser Lys Glu Tyr Asn Ser Ser Asp Lys Thr Asn Gln Ile Cys
            100                 105                 110
Tyr Lys Lys Thr Phe Cys Gly Val Val Ile Pro Asn Ser Glu Glu Ile
            115                 120                 125
Lys Thr Asn Lys Ile Thr Asn Asp Lys Leu Tyr Cys Ala His Phe Asn
            130                 135                 140
Ser Thr His Ile Ile Ile Tyr Tyr Ile Ser Gln Pro Leu Leu Leu Glu
145                 150                 155                 160
Pro His Val Val Tyr Glu Glu Thr Phe Phe Glu Lys Gly Lys Asn Asp
                    165                 170                 175
Gln Ile Asn Cys Gln Gly Met Tyr Ile Ser Leu Arg Ser Val His Val
            180                 185                 190
His Thr His Asn Ala Ile Leu Gln Gln Glu Thr Leu Thr Tyr Ile Lys
            195                 200                 205
Asn Leu Cys Asp Gly Lys Asn Asn Cys Lys Phe Asp Phe Asp Ser Ile
            210                 215                 220
Lys Tyr Glu Asn Lys Ser Leu Thr His Tyr Leu Phe Phe Ile Asn Ile
225                 230                 235                 240
Gln Tyr Gln Cys Ile Ser Pro Leu Asn Leu Gln Glu Asn Glu Met Cys
                    245                 250                 255
Asp Val Tyr Asn Asp Asp Thr His Lys Ala Thr Cys Lys Tyr Gly Phe
            260                 265                 270
Asn Lys Ile Glu Leu Leu Lys Asn Val Cys Glu Glu Asn Tyr Arg Cys
            275                 280                 285
Thr Gln Asp Ile Cys Ser Val Asn Gln Phe Cys Asp Gly Glu Asn Glu
            290                 295                 300
Thr Cys Thr Cys Lys Thr Ser Leu Leu Pro Ser Ala Lys Asn Asn Cys
305                 310                 315                 320
Glu Tyr Asn Asp Leu Cys Thr Val Leu Asn Cys Pro Glu Asn Ser Thr
                    325                 330                 335
Cys Glu Gln Ile Gly Asn Gly Lys Lys Ala Glu Cys Lys Cys Glu Asn
                    340                 345                 350
Gly Lys Tyr Tyr His Asn Asn Lys Cys Tyr Thr Lys Asn Asp Leu Glu
            355                 360                 365
Leu Ala Ile Lys Ile Glu Pro His Lys Glu Lys Phe Tyr Lys Asn
            370                 375                 380
Asn Leu Tyr Gln Gly Lys Ala Leu Lys Pro Glu Tyr Ile Phe Met Gln
385                 390                 395                 400
Cys Glu Asn Gly Phe Ser Ile Glu Val Ile Asn Ala Tyr Val Ser Cys
                    405                 410                 415
Tyr Arg Val Ser Phe Asn Leu Asn Lys Leu Lys Tyr Val Thr Glu Ser
                    420                 425                 430
Leu Lys Lys Met Cys Asp Gly Lys Thr Lys Cys Ala Tyr Gly Asn Thr
            435                 440                 445
Ile Asp Pro Ile Asp Asp Leu Asn His His Asn Ile Cys Asn Asn Phe
            450                 455                 460
Asn Thr Ile Phe Lys Tyr Asp Tyr Leu Cys Val Phe Asn Asn Gln Asn
465                 470                 475                 480
Ile Thr Ser Asp Lys Asn Ser His Leu His Ser Asn Ile Pro Ser Leu
                    485                 490                 495
Tyr Asn Ser Ser Ile Leu Pro Asp Ile Asn Lys Ser Lys Phe His Leu
                    500                 505                 510
```

-continued

```
Ile Ser Arg Asn Ser Arg Thr Asn Gln Tyr Pro His Asn Asn Ile Ser
        515                 520                 525

Met Leu Glu Ile Gln Asn Glu Ile Ser Ser His Asn Ser Asn Gln Phe
530                 535                 540

Ser Thr Asp Pro His Thr Asn Ser Asn Asn Ile Asn Asn Met Asn Ile
545                 550                 555                 560

Lys Lys Val Glu Ile Phe Arg Ser Arg Phe Ser Ser Lys Leu Gln Cys
                565                 570                 575

Gln Gly Gly Lys Ile Asn Ile Asp Lys Ala Ile Leu Lys Gly Gly Glu
            580                 585                 590

Gly Cys Asn Asp Leu Leu Leu Thr Asn Ser Leu Lys Ser Tyr Cys Asn
        595                 600                 605

Asp Leu Ser Glu Cys Asp Ile Gly Leu Ile Tyr His Phe Asp Thr Tyr
    610                 615                 620

Cys Ile Asn Asp Gln Tyr Leu Phe Val Ser Tyr Ser Cys Ser Asn Leu
625                 630                 635                 640

Cys Asn Lys Cys His Asn Asn Ser Thr Cys Tyr Gly Asn Arg Phe Asn
                645                 650                 655

Tyr Asp Cys Phe Cys Asp Asn Pro Tyr Ile Ser Lys Tyr Gly Asn Lys
            660                 665                 670

Leu Cys Glu Arg Pro Asn Asp Cys Glu Ser Val Leu Cys Ser Gln Asn
        675                 680                 685

Gln Val Cys Gln Ile Leu Pro Asn Asp Lys Leu Ile Cys Gln Cys Glu
    690                 695                 700

Glu Gly Tyr Lys Asn Val Lys Gly Lys Cys Val Pro Asp Asn Lys Cys
705                 710                 715                 720

Asp Leu Ser Cys Pro Ser Asn Lys Val Cys Val Ile Glu Asn Gly Lys
                725                 730                 735

Gln Thr Cys Lys Cys Ser Glu Arg Phe Val Leu Glu Asn Gly Val Cys
            740                 745                 750

Ile Cys Ala Asn Asp Tyr Lys Met Glu Asp Gly Ile Asn Cys Ile Ala
        755                 760                 765

Lys Asn Lys Cys Lys Arg Lys Glu Tyr Glu Asn Ile Cys Thr Asn Pro
    770                 775                 780

Asn Glu Met Cys Ala Tyr Asn Glu Glu Thr Asp Ile Val Lys Cys Glu
785                 790                 795                 800

Cys Lys Glu His Tyr Tyr Arg Ser Ser Arg Gly Glu Cys Ile Leu Asn
                805                 810                 815

Asp Tyr Cys Lys Asp Ile Asn Cys Lys Glu Asn Glu Glu Cys Ser Ile
            820                 825                 830

Val Asn Phe Lys Pro Glu Cys Val Cys Lys Glu Asn Leu Lys Lys Asn
        835                 840                 845

Asn Lys Gly Glu Cys Ile Tyr Glu Asn Ser Cys Leu Ile Asn Glu Gly
    850                 855                 860

Asn Cys Pro Lys Asp Ser Lys Cys Ile Tyr Arg Glu Tyr Lys Pro His
865                 870                 875                 880

Glu Cys Val Cys Asn Lys Gln Gly His Val Ala Val Asn Gly Lys Cys
                885                 890                 895

Val Leu Glu Asp Lys Cys Val His Asn Lys Lys Cys Ser Glu Asn Ser
            900                 905                 910

Ile Cys Val Asn Val Met Asn Lys Glu Pro Ile Cys Val Cys Thr Tyr
        915                 920                 925

Asn Tyr Tyr Lys Lys Asp Gly Val Cys Leu Ile Gln Asn Pro Cys Leu
```

-continued

```
    930                 935                 940

Lys Asp Asn Gly Gly Cys Ser Arg Asn Ser Glu Cys Thr Phe Lys Tyr
945                 950                 955                 960

Ser Lys Ile Asn Cys Thr Cys Lys Glu Asn Tyr Lys Asn Lys Asp Asp
                965                 970                 975

Ser Cys Val Pro Asn Thr Asn Glu Tyr Asp Glu Ser Phe Thr Phe Gln
            980                 985                 990

Tyr Asn Asp Asp Ala Ser Ile Ile Leu Gly Ala Cys Gly Met Ile Glu
        995                 1000                1005

Phe Ser Tyr Ile Tyr Asn Gln Ile Ile Trp Lys Ile Asn Asn Ser Lys
    1010                1015                1020

Glu Ser Tyr Val Phe Tyr Tyr Asp Tyr Pro Thr Ala Gly Asn Ile Glu
1025                1030                1035                1040

Val Gln Ile Lys Asn Glu Ile Phe His Thr Ile Ile Tyr Leu Lys Lys
                1045                1050                1055

Lys Ile Gly Asn Ser Val Ile Tyr Asp Asp Phe Gln Val Asp His Gln
            1060                1065                1070

Thr Cys Ile Tyr Glu Asn Val Phe Tyr Tyr Ser Asn Gln Asn
        1075                1080                1085

<210> SEQ ID NO 3
<211> LENGTH: 110
<212> TYPE: PRT
<213> ORGANISM: Artificial Sequence
<220> FEATURE:
<223> OTHER INFORMATION: plasmodium falciparum pfRIP antigenic fragment

<400> SEQUENCE: 3

Asn Glu Glu Thr Asp Ile Val Lys Cys Glu Cys Lys Glu His Tyr Tyr
1               5                   10                  15

Arg Ser Ser Arg Gly Glu Cys Ile Leu Asn Asp Tyr Cys Lys Asp Ile
            20                  25                  30

Asn Cys Lys Glu Asn Glu Glu Cys Ser Ile Val Asn Phe Lys Pro Glu
        35                  40                  45

Cys Val Cys Lys Glu Asn Leu Lys Lys Asn Asn Lys Gly Glu Cys Ile
    50                  55                  60

Tyr Glu Asn Ser Cys Leu Ile Asn Glu Gly Asn Cys Pro Lys Asp Ser
65                  70                  75                  80

Lys Cys Ile Tyr Arg Glu Tyr Lys Pro His Glu Cys Val Cys Asn Lys
                85                  90                  95

Gln Gly His Val Ala Val Asn Gly Lys Cys Val Leu Glu Asp
            100                 105                 110

<210> SEQ ID NO 4
<211> LENGTH: 131
<212> TYPE: PRT
<213> ORGANISM: Artificial Sequence
<220> FEATURE:
<223> OTHER INFORMATION: plasmodium falciparum pfRIP antigenic fragment

<400> SEQUENCE: 4

Ile Asn Ile Gln Tyr Gln Cys Ile Ser Pro Leu Asn Leu Gln Glu Asn
1               5                   10                  15

Glu Met Cys Asp Val Tyr Asn Asp Asp Thr His Lys Ala Thr Cys Lys
            20                  25                  30

Tyr Gly Phe Asn Lys Ile Glu Leu Leu Lys Asn Val Cys Glu Glu Asn
        35                  40                  45
```

```
Tyr Arg Cys Thr Gln Asp Ile Cys Ser Val Asn Gln Phe Cys Asp Gly
    50                  55                  60

Glu Asn Glu Thr Cys Thr Cys Lys Thr Ser Leu Leu Pro Ser Ala Lys
 65                  70                  75                  80

Asn Asn Cys Glu Tyr Asn Asp Leu Cys Thr Val Leu Asn Cys Pro Glu
                 85                  90                  95

Asn Ser Thr Cys Glu Gln Ile Gly Asn Gly Lys Lys Ala Glu Cys Lys
            100                 105                 110

Cys Glu Asn Gly Lys Tyr Tyr His Asn Asn Lys Cys Tyr Thr Lys Asn
        115                 120                 125

Asp Leu Glu
    130

<210> SEQ ID NO 5
<211> LENGTH: 10
<212> TYPE: PRT
<213> ORGANISM: Artificial Sequence
<220> FEATURE:
<223> OTHER INFORMATION: plasmodium falciparum Tryptic peptide

<400> SEQUENCE: 5

Lys Ser Cys Asp Tyr Phe Ile Ser Lys Glu
1               5                   10

<210> SEQ ID NO 6
<211> LENGTH: 16
<212> TYPE: PRT
<213> ORGANISM: Artificial Sequence
<220> FEATURE:
<223> OTHER INFORMATION: plasmodium falciparum Tryptic peptide

<400> SEQUENCE: 6

Lys Glu Tyr Asn Ser Ser Asp Lys Thr Asn Gln Ile Cys Tyr Lys Lys
1               5                   10                  15

<210> SEQ ID NO 7
<211> LENGTH: 12
<212> TYPE: PRT
<213> ORGANISM: Artificial Sequence
<220> FEATURE:
<223> OTHER INFORMATION: plasmodium falciparum Tryptic peptide

<400> SEQUENCE: 7

Lys Leu Ile Cys Gln Cys Glu Glu Gly Tyr Lys Asn
1               5                   10

<210> SEQ ID NO 8
<211> LENGTH: 12
<212> TYPE: PRT
<213> ORGANISM: Artificial Sequence
<220> FEATURE:
<223> OTHER INFORMATION: plasmodium falciparum Tryptic peptide

<400> SEQUENCE: 8

Lys Met Glu Asp Gly Ile Asn Cys Ile Ala Lys Asn
1               5                   10

<210> SEQ ID NO 9
<211> LENGTH: 12
<212> TYPE: PRT
<213> ORGANISM: Artificial Sequence
<220> FEATURE:
<223> OTHER INFORMATION: plasmodium falciparum Tryptic peptide

<400> SEQUENCE: 9
```

```
Lys Ile Asn Cys Thr Cys Lys Glu Asn Tyr Lys Asn
 1               5                  10
```

<210> SEQ ID NO 10
<211> LENGTH: 2971
<212> TYPE: PRT
<213> ORGANISM: Plasmodium falciparum

<400> SEQUENCE: 10

```
Met Gln Arg Trp Ile Phe Cys Asn Ile Val Leu His Ile Leu Ile Tyr
 1               5                  10                  15

Leu Ala Glu Phe Ser His Glu Gln Ser Tyr Ser Ser Asn Glu Lys
             20                  25                  30

Ile Arg Lys Asp Tyr Ser Asp Asn Asn Tyr Glu Pro Thr Phe Ser
         35                  40                  45

Tyr Glu Lys Arg Lys Lys Glu Tyr Gly Lys Asp Glu Ser Tyr Ile Lys
 50                  55                  60

Asn Tyr Arg Gly Asn Asn Phe Ser Tyr Asp Leu Ser Lys Asn Ser Ser
 65                  70                  75                  80

Ile Phe Leu His Met Gly Asn Gly Ser Asn Ser Lys Thr Leu Lys Arg
                 85                  90                  95

Cys Asn Lys Lys Lys Asn Ile Lys Thr Asn Phe Leu Arg Pro Ile Glu
                100                 105                 110

Glu Glu Lys Thr Val Leu Asn Asn Tyr Val Tyr Lys Gly Val Asn Phe
            115                 120                 125

Leu Asp Thr Ile Lys Arg Asn Asp Ser Ser Tyr Lys Phe Asp Val Tyr
130                 135                 140

Lys Asp Thr Ser Phe Leu Lys Asn Arg Glu Tyr Lys Glu Leu Ile Thr
145                 150                 155                 160

Met Gln Tyr Asp Tyr Ala Tyr Leu Glu Ala Thr Lys Glu Val Leu Tyr
                165                 170                 175

Leu Ile Pro Lys Asp Lys Asp Tyr His Lys Phe Tyr Lys Asn Glu Leu
            180                 185                 190

Glu Lys Ile Leu Phe Asn Leu Lys Asp Ser Leu Lys Leu Leu Arg Glu
        195                 200                 205

Gly Tyr Ile Gln Ser Lys Leu Glu Met Ile Arg Ile His Ser Asp Ile
    210                 215                 220

Asp Ile Leu Asn Glu Phe His Gln Gly Asn Ile Ile Asn Asp Asn Tyr
225                 230                 235                 240

Phe Asn Asn Glu Ile Lys Lys Arg Lys Glu Asp Met Glu Lys Tyr Ile
                245                 250                 255

Arg Glu Tyr Asn Leu Tyr Ile Tyr Lys Tyr Glu Asn Gln Leu Lys Ile
            260                 265                 270

Lys Ile Gln Lys Leu Thr Asn Glu Val Ser Ile Asn Leu Asn Lys Ser
        275                 280                 285

Thr Cys Glu Lys Asn Cys Tyr Asn Tyr Ile Leu Lys Leu Glu Lys Tyr
    290                 295                 300

Lys Asn Ile Ile Lys Asp Lys Ile Asn Lys Trp Lys Asp Leu Pro Glu
305                 310                 315                 320

Ile Tyr Ile Asp Asp Lys Ser Phe Ser Tyr Thr Phe Leu Lys Asp Val
                325                 330                 335

Ile Asn Asn Lys Ile Asp Ile Tyr Lys Thr Ile Ser Ser Phe Ile Ser
            340                 345                 350

Thr Gln Lys Gln Leu Tyr Tyr Phe Glu Tyr Ile Tyr Ile Met Asn Lys
```

-continued

```
                355                 360                 365
Asn Thr Leu Asn Leu Leu Ser Tyr Asn Ile Gln Lys Thr Asp Ile Asn
370                 375                 380
Ser Ser Ser Lys Tyr Thr Tyr Thr Lys Ser His Phe Leu Lys Asp Asn
385                 390                 395                 400
His Ile Leu Leu Ser Lys Tyr Tyr Thr Ala Lys Phe Ile Asp Ile Leu
                405                 410                 415
Asn Lys Ile Tyr Tyr Tyr Asn Leu Tyr Lys Asn Lys Ile Leu Leu Phe
                420                 425                 430
Asn Lys Tyr Ile Ile Lys Leu Arg Asn Asp Leu Lys Glu Tyr Ala Phe
                435                 440                 445
Lys Ser Ile Gln Phe Ile Gln Asp Lys Ile Lys Lys His Lys Asp Glu
                450                 455                 460
Leu Ser Ile Glu Asn Ile Leu Gln Glu Val Asn Asn Ile Tyr Ile Lys
465                 470                 475                 480
Tyr Asp Thr Ser Ile Asn Glu Ile Ser Lys Tyr Asn Asn Leu Ile Ile
                485                 490                 495
Asn Thr Asp Leu Gln Ile Val Gln Gln Lys Leu Leu Glu Ile Lys Gln
                500                 505                 510
Lys Lys Asn Asp Ile Thr His Lys Val Gln Leu Ile Asn His Ile Tyr
                515                 520                 525
Lys Asn Ile His Asp Glu Ile Leu Asn Lys Lys Asn Asn Glu Ile Thr
530                 535                 540
Lys Ile Ile Ile Asn Asn Ile Lys Asp His Lys Lys Asp Leu Gln Asp
545                 550                 555                 560
Leu Leu Leu Phe Ile Gln Gln Ile Lys Gln Tyr Asn Ile Leu Thr Asp
                565                 570                 575
His Lys Ile Thr Gln Cys Asn Asn Tyr Tyr Lys Glu Ile Ile Lys Met
                580                 585                 590
Lys Glu Asp Ile Asn His Ile His Ile Tyr Ile Gln Pro Ile Leu Asn
                595                 600                 605
Asn Leu His Thr Leu Lys Gln Val Gln Asn Asn Lys Ile Lys Tyr Glu
                610                 615                 620
Glu His Ile Lys Gln Ile Leu Gln Lys Ile Tyr Asp Lys Lys Glu Ser
625                 630                 635                 640
Leu Lys Lys Ile Ile Leu Leu Lys Asp Glu Ala Gln Leu Asp Ile Thr
                645                 650                 655
Leu Leu Asp Asp Leu Ile Gln Lys Gln Thr Lys Lys Gln Thr Gln Thr
                660                 665                 670
Gln Thr Gln Thr Gln Lys Gln Thr Leu Ile Gln Asn Asn Glu Thr Ile
                675                 680                 685
Gln Leu Ile Ser Gly Gln Glu Asp Lys His Glu Ser Asn Pro Phe Asn
                690                 695                 700
His Ile Gln Thr Tyr Ile Gln Gln Lys Asp Thr Gln Asn Lys Asn Ile
705                 710                 715                 720
Gln Asn Leu Leu Lys Ser Leu Tyr Asn Gly Asn Ile Asn Thr Phe Ile
                725                 730                 735
Asp Thr Ile Ser Lys Tyr Ile Leu Lys Gln Lys Asp Ile Glu Leu Thr
                740                 745                 750
Gln His Val Tyr Thr Asp Glu Lys Ile Asn Asp Tyr Leu Glu Glu Ile
                755                 760                 765
Lys Asn Glu Gln Asn Lys Ile Asp Lys Thr Ile Asp Asp Ile Lys Ile
                770                 775                 780
```

```
Gln Glu Thr Leu Lys Gln Ile Thr His Ile Val Asn Asn Ile Lys Thr
785                 790                 795                 800

Ile Lys Lys Asp Leu Leu Lys Glu Phe Ile Gln His Leu Ile Lys Tyr
                805                 810                 815

Met Asn Glu Arg Tyr Gln Asn Met Gln Gln Gly Tyr Asn Asn Leu Thr
            820                 825                 830

Asn Tyr Ile Asn Gln Tyr Glu Glu Asn Asn Asn Met Lys Gln Tyr
        835                 840                 845

Ile Thr Thr Ile Arg Asn Ile Gln Lys Ile Tyr Tyr Asp Asn Ile Tyr
        850                 855                 860

Ala Lys Glu Lys Glu Ile Arg Ser Gly Gln Tyr Tyr Lys Asp Phe Ile
865                 870                 875                 880

Thr Ser Arg Lys Asn Ile Tyr Asn Ile Arg Glu Asn Ile Ser Lys Asn
                885                 890                 895

Val Asp Met Ile Lys Asn Glu Glu Lys Lys Ile Gln Asn Cys Val
            900                 905                 910

Asp Lys Tyr Asn Ser Ile Lys Gln Tyr Val Lys Met Leu Lys Asn Gly
                915                 920                 925

Asp Thr Gln Asp Glu Asn Asn Asn Asn Asn Asp Ile Tyr Asp Lys
            930                 935                 940

Leu Ile Val Pro Leu Asp Ser Ile Lys Gln Asn Ile Asp Lys Tyr Asn
945                 950                 955                 960

Thr Glu His Asn Phe Ile Thr Phe Thr Asn Lys Ile Asn Thr His Asn
                965                 970                 975

Lys Lys Asn Gln Glu Met Met Glu Glu Phe Ile Tyr Ala Tyr Lys Arg
                980                 985                 990

Leu Lys Ile Leu Lys Ile Leu Asn Ile Ser Leu Lys Ala Cys Glu Lys
                995                 1000                1005

Asn Asn Lys Ser Ile Asn Thr Leu Asn Asp Lys Thr Gln Glu Leu Lys
                1010                1015                1020

Lys Ile Val Thr His Glu Ile Asp Leu Leu Gln Lys Asp Ile Leu Thr
1025                1030                1035                1040

Ser Gln Ile Ser Asn Lys Asn Val Leu Leu Asn Asp Leu Leu Lys
                1045                1050                1055

Glu Ile Glu Gln Tyr Ile Ile Asp Val His Lys Leu Lys Lys Lys Ser
                1060                1065                1070

Asn Leu Leu Phe Thr Tyr Tyr Glu Gln Ser Lys Asn Tyr Phe Tyr Phe
                1075                1080                1085

Lys Asn Lys Lys Asp Asn Phe Asp Ile Gln Lys Thr Ile Asn Lys Met
                1090                1095                1100

Asn Glu Trp Leu Ala Ile Lys Asn Tyr Ile Asn Glu Ile Asn Lys Asn
1105                1110                1115                1120

Tyr Gln Thr Leu Tyr Glu Lys Lys Ile Asn Val Leu Leu His Asn Ser
                1125                1130                1135

Lys Ser Tyr Val Gln Tyr Phe Tyr Asp His Ile Ile Asn Leu Ile Leu
                1140                1145                1150

Gln Lys Lys Asn Tyr Leu Glu Asn Thr Leu Lys Thr Lys Ile Gln Asp
                1155                1160                1165

Asn Glu His Ser Leu Tyr Ala Leu Gln Gln Asn Glu Glu Tyr Gln Lys
                1170                1175                1180

Val Lys Asn Glu Lys Asp Gln Asn Glu Ile Lys Lys Ile Lys Gln Leu
1185                1190                1195                1200
```

-continued

Ile Glu Lys Asn Lys Asn Asp Ile Leu Thr Tyr Glu Asn Asn Ile Glu
        1205                1210                1215

Gln Ile Glu Gln Lys Asn Ile Glu Leu Lys Thr Asn Ala Gln Asn Lys
    1220                1225                1230

Asp Asp Gln Ile Val Asn Thr Leu Asn Glu Val Lys Lys Lys Ile Ile
        1235                1240                1245

Tyr Thr Tyr Phe Lys Val Asp Asn Gln Ile Ser Asn Val Leu Lys Asn
    1250                1255                1260

Tyr Glu Glu Gly Lys Val Glu Tyr Asp Lys Asn Val Val Gln Asn Val
1265                1270                1275                1280

Asn Asp Ala Asp Asp Thr Asn Asp Ile Asp Glu Ile Asn Asp Ile Asp
            1285                1290                1295

Glu Ile Asn Asp Ile Asp Glu Ile Asn Asp Ile Asp Glu Ile Asn Asp
        1300                1305                1310

Ile Asp Glu Ile Lys Asp Ile Asp His Ile Lys His Phe Asp Asp Thr
        1315                1320                1325

Lys His Phe Asp Asp Ile Tyr His Ala Asp Asp Thr Arg Asp Glu Tyr
    1330                1335                1340

His Ile Ala Leu Ser Asn Tyr Ile Lys Thr Glu Leu Arg Asn Ile Asn
1345                1350                1355                1360

Leu Gln Glu Ile Lys Asn Asn Ile Ile Lys Ile Phe Lys Glu Phe Lys
        1365                1370                1375

Ser Ala His Lys Glu Ile Lys Lys Glu Ser Glu Gln Ile Asn Lys Glu
        1380                1385                1390

Phe Thr Lys Met Asp Val Val Ile Asn Gln Leu Arg Asp Ile Asp Arg
    1395                1400                1405

Gln Met Leu Asp Leu Tyr Lys Glu Leu Asp Glu Lys Tyr Ser Glu Phe
    1410                1415                1420

Asn Lys Thr Lys Ile Glu Glu Ile Asn Asn Ile Arg Glu Asn Ile Asn
1425                1430                1435                1440

Asn Val Glu Ile Trp Tyr Glu Lys Asn Ile Ile Glu Tyr Phe Leu Arg
        1445                1450                1455

His Met Asn Asp Gln Lys Asp Lys Ala Ala Lys Tyr Met Glu Asn Ile
        1460                1465                1470

Asp Thr Tyr Lys Asn Asn Ile Glu Ile Ile Ser Lys Gln Ile Asn Pro
    1475                1480                1485

Glu Asn Tyr Val Glu Thr Leu Asn Lys Ser Asn Met Tyr Ser Tyr Val
    1490                1495                1500

Glu Lys Ala Asn Asp Leu Phe Tyr Lys Gln Ile Asn Asn Ile Ile Ile
1505                1510                1515                1520

Asn Ser Asn Gln Leu Lys Asn Glu Ala Phe Thr Ile Asp Glu Leu Gln
        1525                1530                1535

Asn Ile Gln Lys Asn Arg Lys Asn Leu Leu Thr Lys Lys Gln Gln Ile
        1540                1545                1550

Ile Gln Tyr Thr Asn Glu Ile Glu Asn Ile Phe Asn Glu Ile Lys Asn
    1555                1560                1565

Ile Asn Asn Ile Leu Val Leu Thr Asn Tyr Lys Ser Ile Leu Gln Asp
    1570                1575                1580

Ile Ser Gln Asn Ile Asn His Val Ser Ile Tyr Thr Glu Gln Leu His
1585                1590                1595                1600

Asn Leu Tyr Ile Lys Leu Glu Glu Glu Lys Glu Gln Met Lys Thr Leu
        1605                1610                1615

Tyr His Lys Ser Asn Val Leu His Asn Gln Ile Asn Phe Asn Glu Asp

```
                1620                1625                1630
Ala Phe Ile Asn Asn Leu Leu Ile Asn Thr Glu Lys Ile Lys Asn Asp
            1635                1640                1645
Ile Thr His Ile Lys Glu Lys Thr Asn Ile Tyr Met Ile Asp Val Asn
            1650                1655                1660
Lys Ser Lys Asn Asn Ala Gln Leu Tyr Phe His Asn Thr Leu Arg Gly
1665                1670                1675                1680
Asn Glu Lys Ile Glu Tyr Leu Lys Asn Leu Lys Asn Ser Thr Asn Gln
                1685                1690                1695
Gln Ile Thr Leu Gln Glu Leu Lys Gln Val Gln Glu Asn Val Glu Lys
            1700                1705                1710
Val Lys Asp Ile Tyr Asn Gln Thr Ile Lys Tyr Glu Glu Ile Lys
            1715                1720                1725
Lys Asn Tyr His Ile Ile Thr Asp Tyr Glu Asn Lys Ile Asn Asp Ile
            1730                1735                1740
Leu His Asn Ser Phe Ile Lys Gln Ile Asn Met Glu Ser Ser Asn Asn
1745                1750                1755                1760
Lys Lys Gln Thr Lys Gln Ile Ile Asp Ile Ile Asn Asp Lys Thr Phe
                1765                1770                1775
Glu Glu His Ile Lys Thr Ser Lys Thr Lys Ile Asn Met Leu Lys Glu
            1780                1785                1790
Gln Ser Gln Met Lys His Ile Asp Lys Thr Leu Leu Asn Glu Gln Ala
            1795                1800                1805
Leu Lys Leu Phe Val Asp Ile Asn Ser Thr Asn Asn Asn Leu Asp Asn
            1810                1815                1820
Met Leu Ser Glu Ile Asn Ser Ile Gln Asn Asn Ile His Thr Tyr Ile
1825                1830                1835                1840
Gln Glu Ala Asn Lys Ser Phe Asp Lys Phe Lys Ile Ile Cys Asp Gln
                1845                1850                1855
Asn Val Asn Asp Leu Leu Asn Lys Leu Ser Leu Gly Asp Leu Asn Tyr
            1860                1865                1870
Met Asn His Leu Lys Asn Leu Gln Asn Glu Ile Arg Asn Met Asn Leu
            1875                1880                1885
Glu Lys Asn Phe Met Leu Asp Lys Ser Lys Lys Ile Asp Glu Glu Glu
            1890                1895                1900
Lys Lys Leu Asp Ile Leu Lys Val Asn Ile Ser Asn Ile Asn Asn Ser
1905                1910                1915                1920
Leu Asp Lys Leu Lys Lys Tyr Tyr Glu Glu Ala Leu Phe Gln Lys Val
                1925                1930                1935
Lys Glu Lys Ala Glu Ile Gln Lys Glu Asn Ile Glu Lys Ile Lys Gln
            1940                1945                1950
Glu Ile Asn Thr Leu Ser Asp Val Phe Lys Lys Pro Phe Phe Phe Ile
            1955                1960                1965
Gln Leu Asn Thr Asp Ser Ser Gln His Glu Lys Asp Ile Asn Asn Asn
            1970                1975                1980
Val Glu Thr Tyr Lys Asn Asn Ile Asp Glu Ile Tyr Asn Val Phe Ile
1985                1990                1995                2000
Gln Ser Tyr Asn Leu Ile Gln Lys Tyr Ser Ser Glu Ile Phe Ser Ser
                2005                2010                2015
Thr Leu Asn Tyr Ile Gln Thr Lys Glu Ile Lys Glu Lys Ser Ile Lys
            2020                2025                2030
Glu Gln Asn Gln Leu Asn Gln Asn Glu Lys Glu Ala Ser Val Leu Leu
            2035                2040                2045
```

-continued

Lys Asn Ile Lys Ile Asn Glu Thr Ile Lys Leu Phe Lys Gln Ile Lys
2050                2055                2060

Asn Glu Arg Gln Asn Asp Val His Asn Ile Lys Glu Asp Tyr Asn Leu
2065                2070                2075                2080

Leu Gln Gln Tyr Leu Asn Tyr Met Lys Asn Glu Met Glu Gln Leu Lys
                2085                2090                2095

Lys Tyr Lys Asn Asp Val His Met Asp Lys Asn Tyr Val Glu Asn Asn
                2100                2105                2110

Asn Gly Glu Lys Glu Lys Leu Leu Lys Glu Thr Ile Ser Ser Tyr Tyr
                2115                2120                2125

Asp Lys Ile Asn Asn Ile Asn Asn Lys Leu Tyr Ile Tyr Lys Asn Lys
                2130                2135                2140

Glu Asp Thr Tyr Phe Asn Asn Met Ile Lys Val Ser Glu Ile Leu Asn
2145                2150                2155                2160

Ile Ile Ile Lys Lys Lys Gln Gln Asn Glu Gln Arg Ile Val Ile Asn
                2165                2170                2175

Ala Glu Tyr Asp Ser Ser Leu Ile Asn Lys Asp Glu Ile Lys Lys
                2180                2185                2190

Glu Ile Asn Asn Gln Ile Ile Glu Leu Asn Lys His Asn Glu Asn Ile
                2195                2200                2205

Ser Asn Ile Phe Lys Asp Ile Gln Asn Ile Lys Lys Gln Ser Gln Asp
                2210                2215                2220

Ile Ile Thr Asn Met Asn Asp Met Tyr Lys Ser Thr Ile Leu Leu Val
2225                2230                2235                2240

Asp Ile Ile Gln Lys Lys Glu Glu Ala Leu Asn Lys Gln Lys Asn Ile
                2245                2250                2255

Leu Arg Asn Ile Asp Asn Ile Leu Asn Lys Arg Glu Asn Ile Ile Asp
                2260                2265                2270

Lys Val Ile Lys Cys Asn Cys Asp Asp Tyr Lys Asp Ile Leu Ile Gln
                2275                2280                2285

Asn Glu Thr Glu Tyr Gln Lys Leu Gln Asn Ile Asn His Thr Tyr Glu
                2290                2295                2300

Glu Lys Lys Lys Ser Ile Asp Ile Leu Lys Ile Lys Asn Ile Lys Gln
2305                2310                2315                2320

Lys Asn Ile Gln Glu Tyr Lys Asn Lys Leu Glu Gln Met Asn Thr Ile
                2325                2330                2335

Ile Asn Gln Ser Ile Glu Gln His Val Phe Ile Asn Ala Asp Ile Leu
                2340                2345                2350

Gln Asn Glu Lys Ile Lys Leu Glu Glu Ile Ile Lys Asn Leu Asp Ile
                2355                2360                2365

Leu Asp Glu Gln Ile Met Thr Tyr His Asn Ser Ile Asp Glu Leu Tyr
                2370                2375                2380

Lys Leu Gly Ile Gln Cys Asp Asn His Leu Ile Thr Thr Ile Ser Val
2385                2390                2395                2400

Val Val Asn Lys Asn Thr Thr Lys Ile Met Ile His Ile Lys Lys Gln
                2405                2410                2415

Lys Glu Asp Ile Gln Lys Ile Asn Asn Tyr Ile Gln Thr Asn Tyr Met
                2420                2425                2430

Ile Ile Asn Glu Glu Ala Leu Gln Phe His Arg Leu Tyr Gly His Asn
                2435                2440                2445

Leu Ile Ser Glu Asp Asp Lys Asn Asn Leu Val His Ile Ile Lys Glu
                2450                2455                2460

```
Gln Lys Asn Ile Tyr Thr Gln Lys Glu Ile Asp Ile Ser Lys Ile Ile
            2465                2470                2475                2480

Lys His Val Lys Lys Gly Leu Tyr Ser Leu Asn Glu His Asp Met Asn
            2485                2490                2495

His Asp Thr His Met Asn Ile Ile Asn Glu His Ile Asn Asn Asn Ile
            2500                2505                2510

Leu Gln Pro Tyr Thr Gln Leu Ile Asn Met Ile Lys Asp Ile Asp Asn
            2515                2520                2525

Val Phe Ile Lys Ile Gln Asn Asn Lys Phe Glu Gln Ile Gln Lys Tyr
            2530                2535                2540

Ile Glu Ile Ile Lys Ser Leu Glu Gln Leu Asn Lys Asn Ile Asn Thr
2545                2550                2555                2560

Asp Asn Leu Asn Lys Leu Lys Asp Thr Gln Asn Lys Leu Ile Asn Ile
            2565                2570                2575

Glu Thr Glu Met Lys His Lys Gln Lys Gln Leu Ile Asn Lys Met Asn
            2580                2585                2590

Asp Ile Glu Lys Asp Asn Ile Thr Asp Gln Tyr Met His Asp Val Gln
            2595                2600                2605

Gln Asn Ile Phe Glu Pro Ile Thr Leu Lys Met Asn Glu Tyr Asn Thr
            2610                2615                2620

Leu Leu Asn Asp Asn His Asn Asn Ile Asn Asn Glu His Gln Phe
2625                2630                2635                2640

Asn His Leu Asn Ser Leu His Thr Lys Ile Phe Ser His Asn Tyr Asn
            2645                2650                2655

Lys Glu Gln Gln Gln Glu Tyr Ile Thr Asn Ile Met Asn Arg Ile Asp
            2660                2665                2670

Val Phe Ile Asn Asp Leu Asp Thr Tyr Gln Tyr Glu Tyr Tyr Phe Tyr
            2675                2680                2685

Glu Trp Asn Gln Glu Tyr Lys Gln Ile Asp Lys Asn Lys Ile Asn Gln
            2690                2695                2700

His Ile Asn Asn Ile Lys Asn Asn Leu Ile His Val Lys Lys Gln Phe
            2705                2710                2715                2720

Glu His Thr Leu Glu Asn Ile Lys Asn Asn Glu Met Ile Phe Asp Asn
            2725                2730                2735

Ile Gln Leu Lys Lys Lys Asp Ile Asp Leu Ile Ile Asn Ile Asn
            2740                2745                2750

Asn Thr Lys Glu Thr Tyr Leu Lys Glu Leu Asn Lys Lys Lys Asn Val
            2755                2760                2765

Thr Lys Lys Lys Lys Val Asp Glu Lys Ser Glu Ile Asn Asn His His
            2770                2775                2780

Thr Leu Gln His Asp Asn Gln Asn Val Glu Gln Lys Asn Lys Ile Lys
2785                2790                2795                2800

Asp His Asn Leu Ile Thr Lys Pro Asn Asn Asn Ser Ser Glu Glu Ser
            2805                2810                2815

His Gln Asn Glu Gln Met Lys Glu Gln Asn Lys Asn Ile Leu Glu Lys
            2820                2825                2830

Gln Thr Arg Asn Ile Lys Pro His His Val His Asn His Asn His Asn
            2835                2840                2845

His Asn Gln Asn Gln Lys Asp Ser Thr Lys Leu Gln Glu Gln Asp Ile
            2850                2855                2860

Ser Thr His Lys Leu His Asn Thr Ile His Glu Gln Gln Ser Lys Asp
2865                2870                2875                2880

Asn His Gln Gly Asn Arg Glu Lys Lys Gln Lys Asn Gly Asn His Glu
```

```
                     2885              2890              2895
Arg Met Tyr Phe Ala Ser Gly Ile Val Val Ser Ile Leu Phe Leu Phe
                2900              2905              2910

Ser Phe Gly Phe Val Ile Asn Ser Lys Asn Asn Lys Gln Glu Tyr Asp
                2915              2920              2925

Lys Glu Gln Glu Lys Gln Gln Asn Asp Phe Val Cys Asp Met Asn
                2930              2935              2940

Lys Met Asp Asp Lys Ser Thr Gln Lys Tyr Gly Arg Asn Gln Glu Glu
2945              2950              2955              2960

Val Met Glu Ile Phe Phe Asp Asn Asp Tyr Ile
                2965              2970

<210> SEQ ID NO 11
<211> LENGTH: 3130
<212> TYPE: PRT
<213> ORGANISM: Plasmodium falciparum

<400> SEQUENCE: 11

Met Lys Thr Thr Leu Phe Cys Ser Ile Ser Phe Cys Asn Ile Ile Phe
1               5                   10                  15

Phe Phe Leu Glu Leu Ser His Glu His Phe Val Gly Gln Ser Ser Asn
                20                  25                  30

Thr His Gly Ala Ser Ser Val Thr Asp Phe Asn Phe Ser Glu Glu Lys
            35                  40                  45

Asn Leu Lys Ser Phe Glu Gly Lys Asn Asn Asn Asp Asn Tyr Ala
        50                  55                  60

Ser Ile Asn Arg Leu Tyr Arg Lys Lys Pro Tyr Met Lys Arg Ser Leu
65                  70                  75                  80

Ile Asn Leu Glu Asn Asp Leu Phe Arg Leu Glu Pro Ile Ser Tyr Ile
                85                  90                  95

Gln Arg Tyr Tyr Lys Lys Asn Ile Asn Arg Ser Asp Ile Phe His Asn
            100                 105                 110

Lys Lys Glu Arg Gly Ser Lys Val Tyr Ser Asn Val Ser Ser Phe His
        115                 120                 125

Ser Phe Ile Gln Glu Gly Lys Glu Glu Val Phe Ser Ile Trp
    130                 135                 140

Gly Ser Asn Ser Val Leu Asp His Ile Asp Val Leu Arg Asp Asn Gly
145                 150                 155                 160

Thr Val Val Phe Ser Val Gln Pro Tyr Tyr Leu Asp Ile Tyr Thr Cys
                165                 170                 175

Lys Glu Ala Ile Leu Phe Thr Thr Ser Phe Tyr Lys Asp Leu Asp Lys
            180                 185                 190

Ser Ser Ile Thr Lys Ile Asn Glu Asp Ile Glu Lys Phe Asn Glu Glu
        195                 200                 205

Ile Ile Lys Asn Glu Glu Gln Cys Leu Val Gly Gly Lys Thr Asp Phe
    210                 215                 220

Asp Asn Leu Leu Ile Val Leu Glu Asn Ala Glu Lys Ala Asn Val Arg
225                 230                 235                 240

Lys Thr Leu Phe Asp Asn Thr Phe Asn Asp Tyr Lys Asn Lys Lys Ser
                245                 250                 255

Ser Phe Tyr Asn Cys Leu Lys Asn Lys Lys Asn Asp Tyr Asp Lys Lys
            260                 265                 270

Ile Lys Asn Ile Lys Asn Glu Ile Thr Lys Leu Leu Lys Asn Ile Glu
        275                 280                 285
```

```
Ser Thr Gly Asn Met Cys Lys Thr Glu Ser Tyr Val Met Asn Asn
    290                 295                 300

Leu Tyr Leu Leu Arg Val Asn Glu Val Lys Ser Thr Pro Ile Asp Leu
305                 310                 315                 320

Tyr Leu Asn Arg Ala Lys Glu Leu Leu Glu Ser Ser Ser Lys Leu Val
                325                 330                 335

Asn Pro Ile Lys Met Lys Leu Gly Asp Asn Lys Asn Met Tyr Ser Ile
                340                 345                 350

Gly Tyr Ile His Asp Glu Ile Lys Asp Ile Ile Lys Arg Tyr Asn Phe
                355                 360                 365

His Leu Lys His Ile Glu Lys Gly Lys Glu Tyr Ile Lys Arg Ile Thr
370                 375                 380

Gln Ala Asn Asn Ile Ala Asp Lys Met Lys Lys Asp Glu Leu Ile Lys
385                 390                 395                 400

Lys Ile Phe Glu Ser Ser Lys His Phe Ala Ser Phe Lys Tyr Ser Asn
                405                 410                 415

Glu Met Ile Ser Lys Leu Asp Ser Leu Phe Ile Lys Asn Glu Glu Ile
                420                 425                 430

Leu Asn Asn Leu Phe Asn Asn Ile Phe Asn Ile Phe Lys Lys Lys Tyr
                435                 440                 445

Glu Thr Tyr Val Asp Met Lys Thr Ile Glu Ser Lys Tyr Thr Thr Val
450                 455                 460

Met Thr Leu Ser Glu His Leu Leu Glu Tyr Ala Met Asp Val Leu Lys
465                 470                 475                 480

Ala Asn Pro Gln Lys Pro Ile Asp Pro Lys Ala Asn Leu Asp Ser Glu
                485                 490                 495

Val Val Lys Leu Gln Ile Lys Ile Asn Glu Lys Ser Asn Glu Leu Asp
                500                 505                 510

Asn Ala Ile Ser Gln Val Lys Thr Leu Ile Ile Ile Met Lys Ser Phe
                515                 520                 525

Tyr Asp Ile Ile Ile Ser Glu Lys Ala Ser Met Asp Glu Met Glu Lys
                530                 535                 540

Lys Glu Leu Ser Leu Asn Asn Tyr Ile Glu Lys Thr Asp Tyr Ile Leu
545                 550                 555                 560

Gln Thr Tyr Asn Ile Phe Lys Ser Lys Ser Asn Ile Ile Asn Asn Asn
                565                 570                 575

Ser Lys Asn Ile Ser Ser Lys Tyr Ile Thr Ile Glu Gly Leu Lys Asn
                580                 585                 590

Asp Ile Asp Glu Leu Asn Ser Leu Ile Ser Tyr Phe Lys Asp Ser Gln
                595                 600                 605

Glu Thr Leu Ile Lys Asp Asp Glu Leu Lys Lys Asn Met Lys Thr Asp
610                 615                 620

Tyr Leu Asn Asn Val Lys Tyr Ile Glu Glu Asn Val Thr His Ile Asn
625                 630                 635                 640

Glu Ile Ile Leu Leu Lys Asp Ser Ile Thr Gln Arg Ile Ala Asp Ile
                645                 650                 655

Asp Glu Leu Asn Ser Leu Asn Leu Ile Asn Ile Asn Asp Phe Ile Asn
                660                 665                 670

Glu Lys Asn Ile Ser Gln Glu Lys Val Ser Tyr Asn Leu Asn Lys Leu
                675                 680                 685

Tyr Lys Gly Ser Phe Glu Glu Leu Glu Ser Glu Leu Ser His Phe Leu
                690                 695                 700

Asp Thr Lys Tyr Leu Phe His Glu Lys Lys Ser Val Asn Glu Leu Gln
```

```
                705                 710                 715                 720
        Thr Ile Leu Asn Thr Ser Asn Asn Glu Cys Ala Lys Leu Asn Phe Met
                    725                 730                 735
        Lys Ser Asp Asn Asn Asn Asn Asn Asn Ser Asn Ile Ile Asn Leu
                    740                 745                 750
        Leu Lys Thr Glu Leu Ser His Leu Leu Ser Leu Lys Glu Asn Ile Ile
                    755                 760                 765
        Lys Lys Leu Leu Asn His Ile Glu Gln Asn Ile Gln Asn Ser Ser Asn
        770                 775                 780
        Lys Tyr Thr Ile Thr Tyr Thr Asp Ile Asn Asn Arg Met Glu Asp Tyr
        785                 790                 795                 800
        Lys Glu Glu Ile Glu Ser Leu Glu Val Tyr Lys His Thr Ile Gly Asn
                    805                 810                 815
        Ile Gln Lys Glu Tyr Ile Leu His Leu Tyr Glu Asn Asp Lys Asn Ala
                    820                 825                 830
        Leu Ala Val His Asn Thr Ser Met Gln Ile Leu Gln Tyr Lys Asp Ala
                    835                 840                 845
        Ile Gln Asn Ile Lys Asn Lys Ile Ser Asp Asp Ile Lys Ile Leu Lys
        850                 855                 860
        Lys Tyr Lys Glu Met Asn Gln Asp Leu Leu Asn Tyr Tyr Glu Ile Leu
        865                 870                 875                 880
        Asp Lys Lys Leu Lys Asp Asn Thr Tyr Ile Lys Glu Met His Thr Ala
                    885                 890                 895
        Ser Leu Val Gln Ile Thr Gln Tyr Ile Pro Tyr Glu Asp Lys Thr Ile
                    900                 905                 910
        Ser Glu Leu Glu Gln Glu Phe Asn Asn Asn Gln Lys Leu Asp Asn
                    915                 920                 925
        Ile Leu Gln Asp Ile Asn Ala Met Asn Leu Asn Ile Asn Ile Leu Gln
                    930                 935                 940
        Thr Leu Asn Ile Gly Ile Asn Ala Cys Asn Thr Asn Asn Lys Asn Val
        945                 950                 955                 960
        Glu His Leu Leu Asn Lys Lys Ile Glu Leu Lys Asn Ile Leu Asn Asp
                    965                 970                 975
        Gln Met Lys Ile Ile Lys Asn Asp Asp Ile Ile Gln Asp Asn Glu Lys
                    980                 985                 990
        Glu Asn Phe Ser Asn Val Leu Lys Lys Glu Glu Lys Leu Glu Lys
                    995                 1000                1005
        Glu Leu Asp Asp Ile Lys Phe Asn Asn Leu Lys Met Asp Ile His Lys
                    1010                1015                1020
        Leu Leu Asn Ser Tyr Asp His Thr Lys Gln Asn Ile Glu Ser Asn Leu
        1025                1030                1035                1040
        Lys Ile Asn Leu Asp Ser Phe Glu Lys Glu Lys Asp Ser Trp Val His
                    1045                1050                1055
        Phe Lys Ser Thr Ile Asp Ser Leu Tyr Val Glu Tyr Asn Ile Cys Asn
                    1060                1065                1070
        Gln Lys Thr His Asn Thr Ile Lys Gln Gln Lys Asn Asp Ile Ile Glu
                    1075                1080                1085
        Leu Ile Tyr Lys Arg Ile Lys Asp Ile Asn Gln Glu Ile Ile Glu Lys
                    1090                1095                1100
        Val Asp Asn Tyr Tyr Ser Leu Ser Asp Lys Ala Leu Thr Lys Leu Lys
        1105                1110                1115                1120
        Ser Ile His Phe Asn Ile Asp Lys Glu Lys Tyr Lys Asn Pro Lys Ser
                    1125                1130                1135
```

```
Gln Glu Asn Ile Lys Leu Leu Glu Asp Arg Val Met Ile Leu Glu Lys
                1140                1145                1150

Lys Ile Lys Glu Asp Lys Asp Ala Leu Ile Gln Ile Lys Asn Leu Ser
                1155                1160                1165

His Asp His Phe Val Asn Ala Asp Asn Glu Lys Lys Lys Gln Lys Glu
                1170                1175                1180

Lys Glu Glu Asp Asp Glu Gln Thr His Tyr Ser Lys Lys Arg Lys Val
1185                1190                1195                1200

Met Gly Asp Ile Tyr Lys Asp Ile Lys Lys Asn Leu Asp Glu Leu Asn
                1205                1210                1215

Asn Lys Asn Leu Ile Asp Ile Thr Leu Asn Glu Ala Asn Lys Ile Glu
                1220                1225                1230

Ser Glu Tyr Glu Lys Ile Leu Ile Asp Asp Ile Cys Glu Gln Ile Thr
                1235                1240                1245

Asn Glu Ala Lys Lys Ser Asp Thr Ile Lys Gly Lys Ile Glu Ser Tyr
                1250                1255                1260

Lys Lys Asp Ile Asp Tyr Val Asp Val Asp Val Ser Lys Thr Arg Asn
1265                1270                1275                1280

Asp His His Leu Asn Gly Asp Lys Ile His Asp Ser Phe Phe Tyr Glu
                1285                1290                1295

Asp Thr Leu Asn Tyr Lys Ala Tyr Phe Asp Lys Leu Lys Asp Leu Tyr
                1300                1305                1310

Glu Asn Ile Asn Lys Leu Thr Asn Glu Ser Asn Gly Leu Lys Ser Asp
                1315                1320                1325

Ala His Asn Asn Asn Thr Gln Val Asp Lys Leu Lys Glu Ile Asn Leu
                1330                1335                1340

Gln Val Phe Ser Asn Leu Gly Asn Ile Ile Lys Tyr Val Glu Lys Leu
1345                1350                1355                1360

Glu Asn Thr Leu His Glu Leu Lys Asp Met Tyr Glu Phe Leu Glu Thr
                1365                1370                1375

Ile Asp Ile Asn Lys Ile Leu Lys Ser Ile His Asn Ser Met Lys Lys
                1380                1385                1390

Ser Glu Glu Tyr Ser Asn Glu Thr Lys Lys Ile Phe Glu Gln Ser Val
                1395                1400                1405

Asn Ile Thr Asn Gln Phe Ile Glu Asp Val Glu Ile Leu Lys Thr Ser
                1410                1415                1420

Ile Asn Pro Asn Tyr Glu Ser Leu Asn Asp Asp Gln Ile Asp Asp Asn
1425                1430                1435                1440

Ile Lys Ser Leu Val Leu Lys Lys Glu Glu Ile Ser Glu Lys Arg Lys
                1445                1450                1455

Gln Val Asn Lys Tyr Ile Thr Asp Ile Glu Ser Asn Lys Glu Gln Ser
                1460                1465                1470

Asp Leu His Leu Arg Tyr Ala Ser Arg Ser Ile Tyr Val Ile Asp Leu
                1475                1480                1485

Phe Ile Lys His Glu Ile Ile Asn Pro Ser Asp Gly Lys Asn Phe Asp
                1490                1495                1500

Ile Ile Lys Val Lys Glu Met Ile Asn Lys Thr Lys Gln Val Ser Asn
1505                1510                1515                1520

Glu Ala Met Glu Tyr Ala Asn Lys Met Asp Glu Lys Asn Lys Asp Ile
                1525                1530                1535

Ile Lys Ile Glu Asn Glu Leu Tyr Asn Leu Ile Asn Asn Asn Ile Arg
                1540                1545                1550
```

-continued

Ser Leu Lys Gly Val Lys Tyr Glu Lys Val Arg Lys Gln Ala Arg Asn
         1555                1560                1565

Ala Ile Asp Asp Ile Asn Asn Ile His Ser Asn Ile Lys Thr Ile Leu
         1570                1575                1580

Thr Lys Ser Lys Glu Arg Leu Asp Glu Ile Lys Lys Gln Pro Asn Ile
1585                1590                1595                1600

Lys Arg Glu Gly Asp Val Leu Asn Asn Asp Lys Thr Lys Ile Ala Tyr
         1605                1610                1615

Ile Thr Ile Gln Ile Asn Asn Gly Arg Ile Glu Ser Asn Leu Leu Asn
         1620                1625                1630

Ile Leu Asn Met Lys His Asn Ile Asp Thr Ile Leu Asn Lys Ala Met
         1635                1640                1645

Asp Tyr Met Asn Asp Val Ser Lys Ser Asp Gln Ile Val Ile Asn Ile
         1650                1655                1660

Asp Ser Leu Asn Met Asn Asp Ile Tyr Asn Lys Asp Lys Asp Leu Leu
1665                1670                1675                1680

Ile Asn Ile Leu Lys Glu Lys Gln Asn Met Glu Ala Glu Tyr Lys Lys
         1685                1690                1695

Met Asn Glu Met Tyr Asn Tyr Val Asn Glu Thr Glu Lys Glu Ile Ile
         1700                1705                1710

Lys His Lys Lys Asn Tyr Glu Ile Arg Ile Met Glu His Ile Lys Lys
         1715                1720                1725

Glu Thr Asn Glu Lys Lys Lys Lys Phe Met Glu Ser Asn Asn Lys Ser
         1730                1735                1740

Leu Thr Thr Leu Met Asp Ser Phe Arg Ser Met Phe Tyr Asn Glu Tyr
1745                1750                1755                1760

Ile Asn Asp Tyr Asn Ile Asn Glu Asn Phe Glu Lys His Gln Asn Ile
         1765                1770                1775

Leu Asn Glu Ile Tyr Asn Gly Phe Asn Glu Ser Tyr Asn Ile Ile Asn
         1780                1785                1790

Thr Lys Met Thr Glu Ile Ile Asn Asp Asn Leu Asp Tyr Asn Glu Ile
         1795                1800                1805

Lys Glu Ile Lys Glu Val Ala Gln Thr Glu Tyr Asp Lys Leu Asn Lys
         1810                1815                1820

Lys Val Asp Glu Leu Lys Asn Tyr Leu Asn Asn Ile Lys Glu Gln Glu
1825                1830                1835                1840

Gly His Arg Leu Ile Asp Tyr Ile Lys Glu Lys Ile Phe Asn Leu Tyr
         1845                1850                1855

Ile Lys Cys Ser Glu Gln Gln Asn Ile Ile Asp Asp Ser Tyr Asn Tyr
         1860                1865                1870

Ile Thr Val Lys Lys Gln Tyr Ile Lys Thr Ile Glu Asp Val Lys Phe
         1875                1880                1885

Leu Leu Asp Ser Leu Asn Thr Ile Glu Glu Lys Asn Lys Ser Val Ala
         1890                1895                1900

Asn Leu Glu Ile Cys Thr Asn Lys Glu Asp Ile Lys Asn Leu Leu Lys
1905                1910                1915                1920

His Val Ile Lys Leu Ala Asn Phe Ser Gly Ile Ile Val Met Ser Asp
         1925                1930                1935

Thr Asn Thr Glu Ile Thr Pro Glu Asn Pro Leu Glu Asp Asn Asp Leu
         1940                1945                1950

Leu Asn Leu Gln Leu Tyr Phe Glu Arg Lys His Glu Ile Thr Ser Thr
         1955                1960                1965

Leu Glu Asn Asp Ser Asp Leu Glu Leu Asp His Leu Gly Ser Asn Ser

-continued

```
            1970                1975                1980

Asp Glu Ser Ile Asp Asn Leu Lys Val Tyr Asn Asp Ile Ile Glu Leu
1985                1990                1995                2000

His Thr Tyr Ser Thr Gln Ile Leu Lys Tyr Leu Asp Asn Ile Gln Lys
            2005                2010                2015

Leu Lys Gly Asp Cys Asn Asp Leu Val Lys Asp Cys Lys Glu Leu Arg
            2020                2025                2030

Glu Leu Ser Thr Ala Leu Tyr Asp Leu Lys Ile Gln Ile Thr Ser Val
            2035                2040                2045

Ile Asn Arg Glu Asn Asp Ile Ser Asn Asn Ile Asp Ile Val Ser Asn
            2050                2055                2060

Lys Leu Asn Glu Ile Asp Ala Ile Gln Tyr Asn Phe Glu Lys Tyr Lys
2065                2070                2075                2080

Glu Ile Phe Asp Asn Val Glu Glu Tyr Lys Thr Leu Asp Asp Thr Lys
            2085                2090                2095

Asn Ala Tyr Ile Val Lys Lys Ala Glu Ile Leu Lys Asn Val Asp Ile
            2100                2105                2110

Asn Lys Thr Lys Glu Asp Leu Asp Ile Tyr Phe Asn Asp Leu Asp Glu
            2115                2120                2125

Leu Glu Lys Ser Leu Thr Leu Ser Ser Asn Glu Met Glu Ile Lys Thr
            2130                2135                2140

Ile Val Gln Asn Ser Tyr Asn Ser Phe Ser Asp Ile Asn Lys Asn Ile
2145                2150                2155                2160

Asn Asp Ile Asp Lys Glu Met Lys Thr Leu Ile Pro Met Leu Asp Glu
            2165                2170                2175

Leu Leu Asn Glu Gly His Asn Ile Asp Ile Ser Leu Tyr Asn Phe Ile
            2180                2185                2190

Ile Arg Asn Ile Gln Ile Lys Ile Gly Asn Asp Ile Lys Asn Ile Arg
            2195                2200                2205

Glu Gln Glu Asn Asp Thr Asn Ile Cys Phe Glu Tyr Ile Gln Asn Asn
            2210                2215                2220

Tyr Asn Phe Ile Lys Ser Asp Ile Ser Ile Phe Asn Lys Tyr Asp Asp
2225                2230                2235                2240

His Ile Lys Val Asp Asn Tyr Ile Ser Asn Asn Ile Asp Val Val Asn
            2245                2250                2255

Lys His Asn Ser Leu Leu Ser Glu His Val Ile Asn Ala Thr Asn Ile
            2260                2265                2270

Ile Glu Asn Ile Met Thr Ser Ile Val Glu Ile Asn Glu Asp Thr Glu
            2275                2280                2285

Met Asn Ser Leu Glu Glu Thr Gln Asp Lys Leu Leu Glu Leu Tyr Glu
            2290                2295                2300

Asn Phe Lys Lys Glu Lys Asn Ile Ile Asn Asn Tyr Lys Ile Val
2305                2310                2315                2320

His Phe Asn Lys Leu Lys Glu Ile Glu Asn Ser Leu Glu Thr Tyr Asn
            2325                2330                2335

Ser Ile Ser Thr Asn Phe Asn Lys Ile Asn Glu Thr Gln Asn Ile Asp
            2340                2345                2350

Ile Leu Lys Asn Glu Phe Asn Asn Ile Lys Thr Lys Ile Asn Asp Lys
            2355                2360                2365

Val Lys Glu Leu Val His Val Asp Ser Thr Leu Thr Leu Glu Ser Ile
            2370                2375                2380

Gln Thr Phe Asn Asn Leu Tyr Gly Asp Leu Met Ser Asn Ile Gln Asp
2385                2390                2395                2400
```

-continued

```
Val Tyr Lys Tyr Glu Asp Ile Asn Asn Val Glu Leu Lys Lys Val Lys
            2405                2410                2415
Leu Tyr Ile Glu Asn Ile Thr Asn Leu Leu Gly Arg Ile Asn Thr Phe
            2420                2425                2430
Ile Lys Glu Leu Asp Lys Tyr Gln Asp Glu Asn Asn Gly Ile Asp Lys
            2435                2440                2445
Tyr Ile Glu Ile Asn Lys Glu Asn Asn Ser Tyr Ile Ile Lys Leu Lys
            2450                2455                2460
Glu Lys Ala Asn Asn Leu Lys Glu Asn Phe Ser Lys Leu Leu Gln Asn
2465                2470                2475                2480
Ile Lys Arg Asn Glu Thr Glu Leu Tyr Asn Ile Asn Asn Ile Lys Asp
            2485                2490                2495
Asp Ile Met Asn Thr Gly Lys Ser Val Asn Asn Ile Lys Gln Lys Phe
            2500                2505                2510
Ser Ser Asn Leu Pro Leu Lys Glu Lys Leu Phe Gln Met Glu Glu Met
            2515                2520                2525
Leu Leu Asn Ile Asn Asn Ile Met Asn Glu Thr Lys Arg Ile Ser Asn
            2530                2535                2540
Thr Ala Ala Tyr Thr Asn Ile Thr Leu Gln Asp Ile Glu Asn Asn Lys
2545                2550                2555                2560
Asn Lys Glu Asn Asn Asn Met Asn Ile Glu Thr Ile Asp Lys Leu Ile
            2565                2570                2575
Asp His Ile Lys Ile His Asn Glu Lys Ile Gln Ala Glu Ile Leu Ile
            2580                2585                2590
Ile Asp Asp Ala Lys Arg Lys Val Lys Glu Ile Thr Asp Asn Ile Asn
            2595                2600                2605
Lys Ala Phe Asn Glu Ile Thr Glu Asn Tyr Asn Asn Glu Asn Asn Gly
            2610                2615                2620
Val Ile Lys Ser Ala Lys Asn Ile Val Asp Glu Ala Thr Tyr Leu Asn
2625                2630                2635                2640
Asn Glu Leu Asp Lys Phe Leu Leu Lys Leu Asn Glu Leu Leu Ser His
            2645                2650                2655
Asn Asn Asn Asp Ile Lys Asp Leu Gly Asp Glu Lys Leu Ile Leu Lys
            2660                2665                2670
Glu Glu Glu Glu Arg Lys Glu Arg Glu Arg Leu Glu Lys Ala Lys Gln
            2675                2680                2685
Glu Glu Glu Arg Lys Glu Arg Glu Arg Ile Glu Lys Glu Lys Gln Glu
            2690                2695                2700
Lys Glu Arg Leu Glu Arg Glu Lys Gln Glu Gln Leu Lys Glu Glu
2705                2710                2715                2720
Glu Leu Arg Lys Lys Glu Gln Glu Arg Gln Glu Gln Gln Lys Glu
            2725                2730                2735
Glu Ala Leu Lys Arg Gln Glu Gln Glu Arg Leu Gln Lys Glu Glu Glu
            2740                2745                2750
Leu Lys Arg Gln Glu Gln Glu Arg Leu Glu Arg Glu Lys Glu Gln
            2755                2760                2765
Leu Gln Lys Glu Glu Glu Leu Lys Arg Gln Glu Gln Glu Arg Leu Gln
            2770                2775                2780
Lys Glu Glu Ala Leu Lys Arg Gln Glu Gln Glu Arg Leu Gln Lys Glu
2785                2790                2795                2800
Glu Glu Leu Lys Arg Gln Glu Gln Glu Arg Leu Glu Arg Glu Lys Gln
            2805                2810                2815
```

Glu Gln Leu Gln Lys Glu Glu Leu Lys Arg Gln Glu Gln Arg
            2820                2825                2830

Leu Gln Lys Glu Glu Ala Leu Lys Arg Gln Glu Gln Glu Arg Leu Gln
    2835                2840                2845

Lys Glu Glu Leu Lys Arg Gln Glu Gln Glu Arg Leu Glu Arg Lys
            2850                2855                2860

Lys Ile Glu Leu Ala Glu Arg Glu Gln His Ile Lys Ser Lys Leu Glu
2865                2870                2875                2880

Ser Asp Met Val Lys Ile Ile Lys Asp Glu Leu Thr Lys Glu Lys Asp
                2885                2890                2895

Glu Ile Ile Lys Asn Lys Asp Ile Lys Leu Arg His Ser Leu Glu Gln
                2900                2905                2910

Lys Trp Leu Lys His Leu Gln Asn Ile Leu Ser Leu Lys Ile Asp Ser
        2915                2920                2925

Leu Leu Asn Lys Asn Asp Glu Val Ile Lys Asp Asn Glu Thr Gln Leu
        2930                2935                2940

Lys Thr Asn Ile Leu Asn Ser Leu Lys Asn Gln Leu Tyr Leu Asn Leu
2945                2950                2955                2960

Lys Arg Glu Leu Asn Glu Ile Ile Lys Glu Tyr Glu Glu Asn Gln Lys
                2965                2970                2975

Lys Ile Leu His Ser Asn Gln Leu Val Asn Asp Ser Leu Glu Gln Lys
                2980                2985                2990

Thr Asn Arg Leu Val Asp Ile Lys Pro Thr Lys His Gly Asp Ile Tyr
            2995                3000                3005

Thr Asn Lys Leu Ser Asp Asn Glu Thr Glu Met Leu Ile Thr Ser Lys
        3010                3015                3020

Glu Lys Lys Asp Glu Thr Glu Ser Thr Lys Arg Ser Gly Thr Asp His
3025                3030                3035                3040

Thr Asn Ser Ser Glu Ser Thr Thr Asp Asp Asn Thr Asn Asp Arg Asn
                3045                3050                3055

Phe Ser Arg Ser Lys Asn Leu Ser Val Ala Ile Tyr Thr Ala Gly Ser
            3060                3065                3070

Val Ala Leu Cys Val Leu Ile Phe Ser Ser Ile Gly Leu Leu Leu Ile
        3075                3080                3085

Lys Thr Asn Ser Gly Asp Asn Asn Ser Asn Glu Ile Asn Glu Ala Phe
        3090                3095                3100

Glu Pro Asn Asp Asp Val Leu Phe Lys Glu Lys Asp Glu Ile Ile Glu
3105                3110                3115                3120

Ile Thr Phe Asn Asp Asn Asp Ser Thr Ile
                3125                3130

<210> SEQ ID NO 12
<211> LENGTH: 112
<212> TYPE: PRT
<213> ORGANISM: Artificial Sequence
<220> FEATURE:
<223> OTHER INFORMATION: plasmodium falciparum pfRh2a/b antigenic
      fragment

<400> SEQUENCE: 12

Lys Lys Tyr Glu Thr Tyr Val Asp Met Lys Thr Ile Glu Ser Lys Tyr
1               5                   10                  15

Thr Thr Val Met Thr Leu Ser Glu His Leu Leu Glu Tyr Ala Met Asp
            20                  25                  30

Val Leu Lys Ala Asn Pro Gln Lys Pro Ile Asp Pro Lys Ala Asn Leu
        35                  40                  45

Asp Ser Glu Val Val Lys Leu Gln Ile Lys Ile Asn Glu Lys Ser Asn
            50                  55                  60

Glu Leu Asp Asn Ala Ile Ser Gln Val Lys Thr Leu Ile Ile Ile Met
 65                  70                  75                  80

Lys Ser Phe Tyr Asp Ile Ile Ile Ser Glu Lys Ala Ser Met Asp Glu
                85                  90                  95

Met Glu Lys Lys Glu Leu Ser Leu Asn Asn Tyr Ile Glu Lys Thr Asp
               100                 105                 110

<210> SEQ ID NO 13
<211> LENGTH: 499
<212> TYPE: PRT
<213> ORGANISM: Artificial Sequence
<220> FEATURE:
<223> OTHER INFORMATION: plasmodium falciparum pfRh2a/b antigenic
      fragment

<400> SEQUENCE: 13

Glu Leu Arg Glu Leu Ser Thr Ala Leu Tyr Asp Leu Lys Ile Gln Ile
 1               5                  10                  15

Thr Ser Val Ile Asn Arg Glu Asn Asp Ile Ser Asn Asn Ile Asp Ile
            20                  25                  30

Val Ser Asn Lys Leu Asn Glu Ile Asp Ala Ile Gln Tyr Asn Phe Glu
        35                  40                  45

Lys Tyr Lys Glu Ile Phe Asp Asn Val Glu Glu Tyr Lys Thr Leu Asp
 50                  55                  60

Asp Thr Lys Asn Ala Tyr Ile Val Lys Lys Ala Glu Ile Leu Lys Asn
 65                  70                  75                  80

Val Asp Ile Asn Lys Thr Lys Glu Asp Leu Asp Ile Tyr Phe Asn Asp
                85                  90                  95

Leu Asp Glu Leu Glu Lys Ser Leu Thr Leu Ser Ser Asn Glu Met Glu
               100                 105                 110

Ile Lys Thr Ile Val Gln Asn Ser Tyr Asn Ser Phe Ser Asp Ile Asn
           115                 120                 125

Lys Asn Ile Asn Asp Ile Asp Lys Glu Met Lys Thr Leu Ile Pro Met
130                 135                 140

Leu Asp Glu Leu Leu Asn Glu Gly His Asn Ile Asp Ile Ser Leu Tyr
145                 150                 155                 160

Asn Phe Ile Ile Arg Asn Ile Gln Ile Lys Ile Gly Asn Asp Ile Lys
                165                 170                 175

Asn Ile Arg Glu Gln Glu Asn Asp Thr Asn Ile Cys Phe Glu Tyr Ile
            180                 185                 190

Gln Asn Asn Tyr Asn Phe Ile Lys Ser Asp Ile Ser Ile Phe Asn Lys
        195                 200                 205

Tyr Asp Asp His Ile Lys Val Asp Asn Tyr Ile Ser Asn Asn Ile Asp
210                 215                 220

Val Val Asn Lys His Asn Ser Leu Leu Ser Glu His Val Ile Asn Ala
225                 230                 235                 240

Thr Asn Ile Ile Glu Asn Ile Met Thr Ser Ile Val Glu Ile Asn Glu
                245                 250                 255

Asp Thr Glu Met Asn Ser Leu Glu Glu Thr Gln Asp Lys Leu Leu Glu
            260                 265                 270

Leu Tyr Glu Asn Phe Lys Lys Glu Lys Asn Ile Ile Asn Asn Asn Tyr
        275                 280                 285

Lys Ile Val His Phe Asn Lys Leu Lys Glu Ile Glu Asn Ser Leu Glu

```
                290             295             300
Thr Tyr Asn Ser Ile Ser Thr Asn Phe Asn Lys Ile Asn Glu Thr Gln
305                 310                 315                 320

Asn Ile Asp Ile Leu Lys Asn Glu Phe Asn Asn Ile Lys Thr Lys Ile
                325                 330                 335

Asn Asp Lys Val Lys Glu Leu Val His Val Asp Ser Thr Leu Thr Leu
            340                 345                 350

Glu Ser Ile Gln Thr Phe Asn Asn Leu Tyr Gly Asp Leu Met Ser Asn
        355                 360                 365

Ile Gln Asp Val Tyr Lys Tyr Glu Asp Ile Asn Asn Val Glu Leu Lys
    370                 375                 380

Lys Val Lys Leu Tyr Ile Glu Asn Ile Thr Asn Leu Leu Gly Arg Ile
385                 390                 395                 400

Asn Thr Phe Ile Lys Glu Leu Asp Lys Tyr Gln Asp Glu Asn Asn Gly
                405                 410                 415

Ile Asp Lys Tyr Ile Glu Ile Asn Lys Glu Asn Asn Ser Tyr Ile Ile
            420                 425                 430

Lys Leu Lys Glu Lys Ala Asn Asn Leu Lys Glu Asn Phe Ser Lys Leu
        435                 440                 445

Leu Gln Asn Ile Lys Arg Asn Glu Thr Glu Leu Tyr Asn Ile Asn Asn
    450                 455                 460

Ile Lys Asp Asp Ile Met Asn Thr Gly Lys Ser Val Asn Asn Ile Lys
465                 470                 475                 480

Gln Lys Phe Ser Asn Leu Pro Leu Lys Glu Lys Leu Phe Gln Met
                485                 490                 495

Glu Glu Met

<210> SEQ ID NO 14
<211> LENGTH: 3254
<212> TYPE: PRT
<213> ORGANISM: Plasmodium falciparum

<400> SEQUENCE: 14

Met Lys Thr Thr Leu Phe Cys Ser Ile Ser Phe Cys Asn Ile Ile Phe
1               5                   10                  15

Phe Phe Leu Glu Leu Ser His Glu His Phe Val Gly Gln Ser Ser Asn
                20                  25                  30

Thr His Gly Ala Ser Ser Val Thr Asp Phe Asn Phe Ser Glu Glu Lys
            35                  40                  45

Asn Leu Lys Ser Phe Glu Gly Lys Asn Asn Asn Asp Asn Tyr Ala
        50                  55                  60

Ser Ile Asn Arg Leu Tyr Arg Lys Lys Pro Tyr Met Lys Arg Ser Leu
65                  70                  75                  80

Ile Asn Leu Glu Asn Asp Leu Phe Arg Leu Glu Pro Ile Ser Tyr Ile
                85                  90                  95

Gln Arg Tyr Tyr Lys Lys Asn Ile Asn Arg Ser Asp Ile Phe His Asn
            100                 105                 110

Lys Lys Glu Arg Gly Ser Lys Val Tyr Ser Asn Val Ser Ser Phe His
        115                 120                 125

Ser Phe Ile Gln Glu Gly Lys Glu Glu Val Glu Phe Ser Ile Trp
    130                 135                 140

Gly Ser Asn Ser Val Leu Asp His Ile Asp Val Leu Arg Asp Asn Gly
145                 150                 155                 160

Thr Val Val Phe Ser Val Gln Pro Tyr Tyr Leu Asp Ile Tyr Thr Cys
```

```
                165                 170                 175
Lys Glu Ala Ile Leu Phe Thr Thr Ser Phe Tyr Lys Asp Leu Asp Lys
                180                 185                 190

Ser Ser Ile Thr Lys Ile Asn Glu Asp Ile Glu Lys Phe Asn Glu Glu
                195                 200                 205

Ile Ile Lys Asn Glu Glu Gln Cys Leu Val Gly Gly Lys Thr Asp Phe
        210                 215                 220

Asp Asn Leu Leu Ile Val Leu Glu Asn Ala Glu Lys Ala Asn Val Arg
225                 230                 235                 240

Lys Thr Leu Phe Asp Asn Thr Phe Asn Asp Tyr Lys Asn Lys Lys Ser
                245                 250                 255

Ser Phe Tyr Asn Cys Leu Lys Asn Lys Lys Asn Asp Tyr Asp Lys Lys
                260                 265                 270

Ile Lys Asn Ile Lys Asn Glu Ile Thr Lys Leu Leu Lys Asn Ile Glu
        275                 280                 285

Ser Thr Gly Asn Met Cys Lys Thr Glu Ser Tyr Val Met Asn Asn Asn
        290                 295                 300

Leu Tyr Leu Leu Arg Val Asn Glu Val Lys Ser Thr Pro Ile Asp Leu
305                 310                 315                 320

Tyr Leu Asn Arg Ala Lys Glu Leu Leu Glu Ser Ser Lys Leu Val
                325                 330                 335

Asn Pro Ile Lys Met Lys Leu Gly Asp Asn Lys Asn Met Tyr Ser Ile
                340                 345                 350

Gly Tyr Ile His Asp Glu Ile Lys Asp Ile Ile Lys Arg Tyr Asn Phe
        355                 360                 365

His Leu Lys His Ile Glu Lys Gly Lys Glu Tyr Ile Lys Arg Ile Thr
        370                 375                 380

Gln Ala Asn Asn Ile Ala Asp Lys Met Lys Lys Asp Glu Leu Ile Lys
385                 390                 395                 400

Lys Ile Phe Glu Ser Ser Lys His Phe Ala Ser Phe Lys Tyr Ser Asn
                405                 410                 415

Glu Met Ile Ser Lys Leu Asp Ser Leu Phe Ile Lys Asn Glu Glu Ile
                420                 425                 430

Leu Asn Asn Leu Phe Asn Asn Ile Phe Asn Ile Phe Lys Lys Lys Tyr
        435                 440                 445

Glu Thr Tyr Val Asp Met Lys Thr Ile Glu Ser Lys Tyr Thr Thr Val
        450                 455                 460

Met Thr Leu Ser Glu His Leu Leu Glu Tyr Ala Met Asp Val Leu Lys
465                 470                 475                 480

Ala Asn Pro Gln Lys Pro Ile Asp Pro Lys Ala Asn Leu Asp Ser Glu
                485                 490                 495

Val Val Lys Leu Gln Ile Lys Ile Asn Glu Lys Ser Asn Glu Leu Asp
                500                 505                 510

Asn Ala Ile Ser Gln Val Lys Thr Leu Ile Ile Met Lys Ser Phe
        515                 520                 525

Tyr Asp Ile Ile Ile Ser Glu Lys Ala Ser Met Asp Glu Met Glu Lys
        530                 535                 540

Lys Glu Leu Ser Leu Asn Asn Tyr Ile Glu Lys Thr Asp Tyr Ile Leu
545                 550                 555                 560

Gln Thr Tyr Asn Ile Phe Lys Ser Lys Ser Asn Ile Ile Asn Asn Asn
                565                 570                 575

Ser Lys Asn Ile Ser Ser Lys Tyr Ile Thr Ile Glu Gly Leu Lys Asn
                580                 585                 590
```

```
Asp Ile Asp Glu Leu Asn Ser Leu Ile Ser Tyr Phe Lys Asp Ser Gln
            595                 600                 605

Glu Thr Leu Ile Lys Asp Asp Glu Leu Lys Lys Asn Met Lys Thr Asp
610                 615                 620

Tyr Leu Asn Asn Val Lys Tyr Ile Glu Asn Val Thr His Ile Asn
625                 630                 635                 640

Glu Ile Ile Leu Leu Lys Asp Ser Ile Thr Gln Arg Ile Ala Asp Ile
                645                 650                 655

Asp Glu Leu Asn Ser Leu Asn Leu Ile Asn Ile Asn Asp Phe Ile Asn
                660                 665                 670

Glu Lys Asn Ile Ser Gln Glu Lys Val Ser Tyr Asn Leu Asn Lys Leu
                675                 680                 685

Tyr Lys Gly Ser Phe Glu Glu Leu Glu Ser Glu Leu Ser His Phe Leu
                690                 695                 700

Asp Thr Lys Tyr Leu Phe His Glu Lys Lys Ser Val Asn Glu Leu Gln
705                 710                 715                 720

Thr Ile Leu Asn Thr Ser Asn Asn Glu Cys Ala Lys Leu Asn Phe Met
                725                 730                 735

Lys Ser Asp Asn Asn Asn Asn Asn Asn Ser Asn Ile Ile Asn Leu
                740                 745                 750

Leu Lys Thr Glu Leu Ser His Leu Leu Ser Leu Lys Glu Asn Ile Ile
                755                 760                 765

Lys Lys Leu Leu Asn His Ile Glu Gln Asn Ile Gln Asn Ser Ser Asn
770                 775                 780

Lys Tyr Thr Ile Thr Tyr Thr Asp Ile Asn Asn Arg Met Glu Asp Tyr
785                 790                 795                 800

Lys Glu Glu Ile Glu Ser Leu Glu Val Tyr Lys His Thr Ile Gly Asn
                805                 810                 815

Ile Gln Lys Glu Tyr Ile Leu His Leu Tyr Glu Asn Asp Lys Asn Ala
                820                 825                 830

Leu Ala Val His Asn Thr Ser Met Gln Ile Leu Gln Tyr Lys Asp Ala
                835                 840                 845

Ile Gln Asn Ile Lys Asn Lys Ile Ser Asp Asp Ile Lys Ile Leu Lys
                850                 855                 860

Lys Tyr Lys Glu Met Asn Gln Asp Leu Leu Asn Tyr Tyr Glu Ile Leu
865                 870                 875                 880

Asp Lys Lys Leu Lys Asp Asn Thr Tyr Ile Lys Glu Met His Thr Ala
                885                 890                 895

Ser Leu Val Gln Ile Thr Gln Tyr Ile Pro Tyr Glu Asp Lys Thr Ile
                900                 905                 910

Ser Glu Leu Glu Gln Glu Phe Asn Asn Asn Gln Lys Leu Asp Asn
                915                 920                 925

Ile Leu Gln Asp Ile Asn Ala Met Asn Leu Asn Ile Asn Ile Leu Gln
930                 935                 940

Thr Leu Asn Ile Gly Ile Asn Ala Cys Asn Thr Asn Lys Asn Val
945                 950                 955                 960

Glu His Leu Leu Asn Lys Lys Ile Glu Leu Lys Asn Ile Leu Asn Asp
                965                 970                 975

Gln Met Lys Ile Ile Lys Asn Asp Asp Ile Ile Gln Asp Asn Glu Lys
                980                 985                 990

Glu Asn Phe Ser Asn Val Leu Lys Lys Glu Glu Lys Leu Glu Lys
                995                 1000                1005
```

-continued

```
Glu Leu Asp Asp Ile Lys Phe Asn Asn Leu Lys Met Asp Ile His Lys
    1010                1015                1020

Leu Leu Asn Ser Tyr Asp His Thr Lys Gln Asn Ile Glu Ser Asn Leu
1025                1030                1035                1040

Lys Ile Asn Leu Asp Ser Phe Glu Lys Glu Lys Asp Ser Trp Val His
            1045                1050                1055

Phe Lys Ser Thr Ile Asp Ser Leu Tyr Val Glu Tyr Asn Ile Cys Asn
        1060                1065                1070

Gln Lys Thr His Asn Thr Ile Lys Gln Gln Lys Asn Asp Ile Ile Glu
    1075                1080                1085

Leu Ile Tyr Lys Arg Ile Lys Asp Ile Asn Gln Glu Ile Ile Glu Lys
1090                1095                1100

Val Asp Asn Tyr Tyr Ser Leu Ser Asp Lys Ala Leu Thr Lys Leu Lys
1105                1110                1115                1120

Ser Ile His Phe Asn Ile Asp Lys Glu Lys Tyr Lys Asn Pro Lys Ser
            1125                1130                1135

Gln Glu Asn Ile Lys Leu Leu Glu Asp Arg Val Met Ile Leu Glu Lys
        1140                1145                1150

Lys Ile Lys Glu Asp Lys Asp Ala Leu Ile Gln Ile Lys Asn Leu Ser
    1155                1160                1165

His Asp His Phe Val Asn Ala Asp Asn Glu Lys Lys Gln Lys Glu
1170                1175                1180

Lys Glu Glu Asp Asp Glu Gln Thr His Tyr Ser Lys Lys Arg Lys Val
1185                1190                1195                1200

Met Gly Asp Ile Tyr Lys Asp Ile Lys Lys Asn Leu Asp Glu Leu Asn
            1205                1210                1215

Asn Lys Asn Leu Ile Asp Ile Thr Leu Asn Glu Ala Asn Lys Ile Glu
        1220                1225                1230

Ser Glu Tyr Glu Lys Ile Leu Ile Asp Asp Ile Cys Glu Gln Ile Thr
    1235                1240                1245

Asn Glu Ala Lys Lys Ser Asp Thr Ile Lys Glu Lys Ile Glu Ser Tyr
    1250                1255                1260

Lys Lys Asp Ile Asp Tyr Val Asp Val Asp Val Ser Lys Thr Arg Asn
1265                1270                1275                1280

Asp His His Leu Asn Gly Asp Lys Ile His Asp Ser Phe Phe Tyr Glu
            1285                1290                1295

Asp Thr Leu Asn Tyr Lys Ala Tyr Phe Asp Lys Leu Lys Asp Leu Tyr
        1300                1305                1310

Glu Asn Ile Asn Lys Leu Thr Asn Glu Ser Asn Gly Leu Lys Ser Asp
    1315                1320                1325

Ala His Asn Asn Thr Gln Val Asp Lys Leu Lys Glu Ile Asn Leu
1330                1335                1340

Gln Val Phe Ser Asn Leu Gly Asn Ile Ile Lys Tyr Val Glu Lys Leu
1345                1350                1355                1360

Glu Asn Thr Leu His Glu Leu Lys Asp Met Tyr Glu Phe Leu Glu Thr
            1365                1370                1375

Ile Asp Ile Asn Lys Ile Leu Lys Ser Ile His Asn Ser Met Lys Lys
        1380                1385                1390

Ser Glu Glu Tyr Ser Asn Glu Thr Lys Lys Ile Phe Glu Gln Ser Val
    1395                1400                1405

Asn Ile Thr Asn Gln Phe Ile Glu Asp Val Glu Ile Leu Lys Thr Ser
    1410                1415                1420

Ile Asn Pro Asn Tyr Glu Ser Leu Asn Asp Asp Gln Ile Asp Asp Asn
```

```
1425                1430                1435                1440

Ile Lys Ser Leu Val Leu Lys Lys Glu Glu Ile Ser Glu Lys Arg Lys
                1445                1450                1455

Gln Val Asn Lys Tyr Ile Thr Asp Ile Glu Ser Asn Lys Glu Gln Ser
            1460                1465                1470

Asp Leu His Leu Arg Tyr Ala Ser Arg Ser Ile Tyr Val Ile Asp Leu
        1475                1480                1485

Phe Ile Lys His Glu Ile Ile Asn Pro Ser Asp Gly Lys Asn Phe Asp
    1490                1495                1500

Ile Ile Lys Val Lys Glu Met Ile Asn Lys Thr Lys Gln Val Ser Asn
1505                1510                1515                1520

Glu Ala Met Glu Tyr Ala Asn Lys Met Asp Glu Lys Asn Lys Asp Ile
                1525                1530                1535

Ile Lys Ile Glu Asn Glu Leu Tyr Asn Leu Ile Asn Asn Asn Ile Arg
            1540                1545                1550

Ser Leu Lys Gly Val Lys Tyr Glu Lys Val Arg Lys Gln Ala Arg Asn
        1555                1560                1565

Ala Ile Asp Asp Ile Asn Asn Ile His Ser Asn Ile Lys Thr Ile Leu
    1570                1575                1580

Thr Lys Ser Lys Glu Arg Leu Asp Glu Ile Lys Lys Gln Pro Asn Ile
1585                1590                1595                1600

Lys Arg Glu Gly Asp Val Leu Asn Asn Asp Lys Thr Lys Ile Ala Tyr
                1605                1610                1615

Ile Thr Ile Gln Ile Asn Asn Gly Arg Ile Glu Ser Asn Leu Leu Asn
            1620                1625                1630

Ile Leu Asn Met Lys His Asn Ile Asp Thr Ile Leu Asn Lys Ala Met
        1635                1640                1645

Asp Tyr Met Asn Asp Val Ser Lys Ser Asp Gln Ile Val Ile Asn Ile
    1650                1655                1660

Asp Ser Leu Asn Met Asn Asp Ile Tyr Asn Lys Asp Lys Asp Leu Leu
1665                1670                1675                1680

Ile Asn Ile Leu Lys Glu Lys Gln Asn Met Glu Ala Glu Tyr Lys Lys
                1685                1690                1695

Met Asn Glu Met Tyr Asn Tyr Val Asn Glu Thr Lys Glu Ile Ile
            1700                1705                1710

Lys His Lys Lys Asn Tyr Glu Ile Arg Ile Met Glu His Ile Lys Lys
        1715                1720                1725

Glu Thr Asn Glu Lys Lys Lys Phe Met Glu Ser Asn Asn Lys Ser
    1730                1735                1740

Leu Thr Thr Leu Met Asp Ser Phe Arg Ser Met Phe Tyr Asn Glu Tyr
1745                1750                1755                1760

Ile Asn Asp Tyr Asn Ile Asn Glu Asn Phe Glu Lys His Gln Asn Ile
                1765                1770                1775

Leu Asn Glu Ile Tyr Asn Gly Phe Asn Glu Ser Tyr Asn Ile Ile Asn
            1780                1785                1790

Thr Lys Met Thr Glu Ile Ile Asn Asp Asn Leu Asp Tyr Asn Glu Ile
        1795                1800                1805

Lys Glu Ile Lys Glu Val Ala Gln Thr Glu Tyr Asp Lys Leu Asn Lys
    1810                1815                1820

Lys Val Asp Glu Leu Lys Asn Tyr Leu Asn Asn Ile Lys Glu Gln Glu
1825                1830                1835                1840

Gly His Arg Leu Ile Asp Tyr Ile Lys Glu Lys Ile Phe Asn Leu Tyr
                1845                1850                1855
```

-continued

```
Ile Lys Cys Ser Glu Gln Gln Asn Ile Ile Asp Asp Ser Tyr Asn Tyr
            1860                1865                1870
Ile Thr Val Lys Lys Gln Tyr Ile Lys Thr Ile Glu Asp Val Lys Phe
            1875                1880            1885
Leu Leu Asp Ser Leu Asn Thr Ile Glu Glu Lys Asn Lys Ser Val Ala
        1890                1895                1900
Asn Leu Glu Ile Cys Thr Asn Lys Asp Ile Lys Asn Leu Leu Lys
1905                1910                1915                1920
His Val Ile Lys Leu Ala Asn Phe Ser Gly Ile Ile Val Met Ser Asp
                1925                1930                1935
Thr Asn Thr Glu Ile Thr Pro Glu Asn Pro Leu Glu Asn Asp Leu
            1940                1945                1950
Leu Asn Leu Gln Leu Tyr Phe Glu Arg Lys His Glu Ile Thr Ser Thr
            1955                1960                1965
Leu Glu Asn Asp Ser Asp Leu Glu Leu Asp His Leu Gly Ser Asn Ser
        1970                1975                1980
Asp Glu Ser Ile Asp Asn Leu Lys Val Tyr Asn Asp Ile Ile Glu Leu
1985                1990                1995                2000
His Thr Tyr Ser Thr Gln Ile Leu Lys Tyr Leu Asp Asn Ile Gln Lys
                2005                2010                2015
Leu Lys Gly Asp Cys Asn Asp Leu Val Lys Asp Cys Lys Glu Leu Arg
            2020                2025                2030
Glu Leu Ser Thr Ala Leu Tyr Asp Leu Lys Ile Gln Ile Thr Ser Val
            2035                2040            2045
Ile Asn Arg Glu Asn Asp Ile Ser Asn Asn Ile Asp Ile Val Ser Asn
            2050                2055                2060
Lys Leu Asn Glu Ile Asp Ala Ile Gln Tyr Asn Phe Glu Lys Tyr Lys
2065                2070                2075                2080
Glu Ile Phe Asp Asn Val Glu Glu Tyr Lys Thr Leu Asp Asp Thr Lys
            2085                2090                2095
Asn Ala Tyr Ile Val Lys Lys Ala Glu Ile Leu Lys Asn Val Asp Ile
            2100                2105                2110
Asn Lys Thr Lys Glu Asp Leu Asp Ile Tyr Phe Asn Asp Leu Asp Glu
        2115                2120                2125
Leu Glu Lys Ser Leu Thr Leu Ser Ser Asn Glu Met Glu Ile Lys Thr
            2130                2135                2140
Ile Val Gln Asn Ser Tyr Asn Ser Phe Ser Asp Ile Asn Lys Asn Ile
2145                2150                2155                2160
Asn Asp Ile Asp Lys Glu Met Lys Thr Leu Ile Pro Met Leu Asp Glu
                2165                2170                2175
Leu Leu Asn Glu Gly His Asn Ile Asp Ile Ser Leu Tyr Asn Phe Ile
            2180                2185                2190
Ile Arg Asn Ile Gln Ile Lys Ile Gly Asn Asp Ile Lys Asn Ile Arg
            2195                2200                2205
Glu Gln Glu Asn Asp Thr Asn Ile Cys Phe Glu Tyr Ile Gln Asn Asn
            2210                2215                2220
Tyr Asn Phe Ile Lys Ser Asp Ile Ser Ile Phe Asn Lys Tyr Asp Asp
2225                2230                2235                2240
His Ile Lys Val Asp Asn Tyr Ile Ser Asn Asn Ile Asp Val Val Asn
                2245                2250                2255
Lys His Asn Ser Leu Leu Ser Glu His Val Ile Asn Ala Thr Asn Ile
            2260                2265                2270
```

-continued

```
Ile Glu Asn Ile Met Thr Ser Ile Val Glu Ile Asn Glu Asp Thr Glu
            2275                2280                2285

Met Asn Ser Leu Glu Glu Thr Gln Asp Lys Leu Leu Glu Leu Tyr Glu
            2290                2295                2300

Asn Phe Lys Lys Glu Lys Asn Ile Ile Asn Asn Tyr Lys Ile Val
2305                2310                2315                2320

His Phe Asn Lys Leu Lys Glu Ile Glu Asn Ser Leu Glu Thr Tyr Asn
            2325                2330                2335

Ser Ile Ser Thr Asn Phe Asn Lys Ile Asn Glu Thr Gln Asn Ile Asp
            2340                2345                2350

Ile Leu Lys Asn Glu Phe Asn Asn Ile Lys Thr Lys Ile Asn Asp Lys
            2355                2360                2365

Val Lys Glu Leu Val His Val Asp Ser Thr Leu Thr Leu Glu Ser Ile
            2370                2375                2380

Gln Thr Phe Asn Asn Leu Tyr Gly Asp Leu Met Ser Asn Ile Gln Asp
2385                2390                2395                2400

Val Tyr Lys Tyr Glu Asp Ile Asn Asn Val Glu Leu Lys Lys Val Lys
            2405                2410                2415

Leu Tyr Ile Glu Asn Ile Thr Asn Leu Leu Gly Arg Ile Asn Thr Phe
            2420                2425                2430

Ile Lys Glu Leu Asp Lys Tyr Gln Asp Glu Asn Asn Gly Ile Asp Lys
            2435                2440                2445

Tyr Ile Glu Ile Asn Lys Glu Asn Ser Tyr Ile Ile Lys Leu Lys
            2450                2455                2460

Glu Lys Ala Asn Asn Leu Lys Glu Asn Phe Ser Lys Leu Leu Gln Asn
2465                2470                2475                2480

Ile Lys Arg Asn Glu Thr Glu Leu Tyr Asn Ile Asn Asn Ile Lys Asp
            2485                2490                2495

Asp Ile Met Asn Thr Gly Lys Ser Val Asn Asn Ile Lys Gln Lys Phe
            2500                2505                2510

Ser Ser Asn Leu Pro Leu Lys Glu Lys Leu Phe Gln Met Glu Glu Met
            2515                2520                2525

Leu Leu Asn Ile Asn Asn Ile Met Asn Glu Thr Lys Arg Ile Ser Asn
            2530                2535                2540

Thr Asp Ala Tyr Thr Asn Ile Thr Leu Gln Asp Ile Glu Asn Asn Lys
2545                2550                2555                2560

Asn Lys Glu Asn Asn Asn Met Asn Ile Glu Thr Ile Asp Lys Leu Ile
            2565                2570                2575

Asp His Ile Lys Ile His Asn Glu Lys Ile Gln Ala Gly Ile Leu Ile
            2580                2585                2590

Ile Asp Asp Ala Lys Arg Lys Val Lys Glu Ile Thr Asp Asn Ile Asn
            2595                2600                2605

Lys Ala Phe Asn Glu Ile Thr Glu Asn Tyr Asn Asn Glu Asn Asn Gly
            2610                2615                2620

Val Ile Lys Ser Ala Lys Asn Ile Val Asp Lys Ala Thr Tyr Leu Asn
2625                2630                2635                2640

Asn Glu Leu Asp Lys Phe Leu Leu Lys Leu Asn Glu Leu Leu Ser His
            2645                2650                2655

Asn Asn Asn Asp Ile Lys Asp Leu Gly Asp Glu Lys Leu Ile Leu Lys
            2660                2665                2670

Glu Glu Glu Glu Arg Lys Glu Arg Glu Arg Leu Glu Lys Ala Lys Gln
            2675                2680                2685

Glu Glu Glu Arg Lys Glu Arg Glu Arg Ile Glu Lys Glu Lys Gln Glu
```

```
                2690            2695            2700
Lys Glu Arg Leu Glu Arg Glu Lys Gln Glu Gln Leu Lys Lys Glu Ala
2705            2710            2715            2720
Leu Lys Lys Gln Glu Gln Arg Gln Glu Gln Gln Lys Glu Glu
        2725            2730            2735
Ala Leu Lys Arg Gln Glu Glu Arg Leu Gln Lys Glu Glu Leu
        2740            2745            2750
Lys Arg Gln Glu Gln Glu Arg Leu Glu Arg Lys Gln Glu Gln Leu
    2755            2760            2765
Gln Lys Glu Glu Glu Leu Arg Lys Lys Glu Gln Glu Lys Gln Gln Gln
2770            2775            2780
Arg Asn Ile Gln Glu Leu Glu Glu Gln Lys Lys Pro Glu Ile Ile Asn
2785            2790            2795            2800
Glu Ala Leu Val Lys Gly Asp Lys Ile Leu Glu Gly Ser Asp Gln Arg
        2805            2810            2815
Asn Met Glu Leu Ser Lys Pro Asn Val Ser Met Asp Asn Thr Asn Asn
        2820            2825            2830
Ser Pro Ile Ser Asn Ser Glu Ile Thr Glu Ser Asp Ile Asp Asn
    2835            2840            2845
Ser Glu Asn Ile His Thr Ser His Met Ser Asp Ile Glu Ser Thr Gln
    2850            2855            2860
Thr Ser His Arg Ser Asn Thr His Gly Gln Gln Ile Ser Asp Ile Val
2865            2870            2875            2880
Glu Asp Gln Ile Thr His Pro Ser Asn Ile Gly Gly Glu Lys Ile Thr
        2885            2890            2895
His Asn Asp Glu Ile Ser Ile Thr Gly Glu Arg Asn Asn Ile Ser Asp
        2900            2905            2910
Val Asn Asp Tyr Ser Glu Ser Ser Asn Ile Phe Glu Asn Gly Asp Ser
    2915            2920            2925
Thr Ile Asn Thr Ser Thr Arg Asn Thr Ser Ser Thr His Asp Glu Ser
    2930            2935            2940
His Ile Ser Pro Ile Ser Asn Ala Tyr Asp His Val Val Ser Asp Asn
2945            2950            2955            2960
Lys Lys Ser Met Asp Glu Asn Ile Lys Asp Lys Leu Lys Ile Asp Glu
        2965            2970            2975
Ser Ile Thr Thr Asp Glu Gln Ile Arg Leu Asp Asp Asn Ser Asn Ile
        2980            2985            2990
Val Arg Ile Asp Ser Thr Asp Gln Arg Asp Ala Ser Ser His Gly Ser
    2995            3000            3005
Ser Asn Arg Asp Asp Asp Glu Ile Ser His Val Gly Ser Asp Ile His
    3010            3015            3020
Met Asp Ser Val Asp Ile His Asp Ser Ile Asp Thr Asp Glu Asn Ala
3025            3030            3035            3040
Asp His Arg His Asn Val Asn Ser Val Asp Ser Leu Ser Ser Ser Asp
        3045            3050            3055
Tyr Thr Asp Thr Gln Lys Asp Phe Ser Ser Ile Ile Lys Asp Gly Gly
        3060            3065            3070
Asn Lys Glu Gly His Ala Glu Asn Glu Ser Lys Glu Tyr Glu Ser Gln
    3075            3080            3085
Thr Glu Gln Thr His Glu Glu Gly Ile Met Asn Pro Asn Lys Tyr Ser
    3090            3095            3100
Ile Ser Glu Val Asp Gly Ile Lys Leu Asn Glu Glu Ala Lys His Lys
3105            3110            3115            3120
```

-continued

```
Ile Thr Glu Lys Leu Val Asp Ile Tyr Pro Ser Thr Tyr Arg Thr Leu
            3125                3130                3135

Asp Glu Pro Met Glu Thr His Gly Pro Asn Glu Lys Phe His Met Phe
            3140                3145                3150

Gly Ser Pro Tyr Val Thr Glu Glu Asp Tyr Thr Glu Lys His Asp Tyr
            3155                3160                3165

Asp Lys His Glu Asp Phe Asn Asn Glu Arg Tyr Ser Asn His Asn Lys
            3170                3175                3180

Met Asp Asp Phe Val Tyr Asn Ala Gly Gly Val Val Cys Cys Val Leu
3185                3190                3195                3200

Phe Phe Ala Ser Ile Thr Phe Ser Met Asp Arg Ser Asn Lys Asp
            3205                3210                3215

Glu Cys Asp Phe Asp Met Cys Glu Val Asn Asn Asn Asp His Leu
            3220                3225                3230

Ser Asn Tyr Ala Asp Lys Glu Glu Ile Ile Glu Ile Val Phe Asp Glu
            3235                3240                3245

Asn Glu Glu Lys Tyr Phe
    3250

<210> SEQ ID NO 15
<211> LENGTH: 1716
<212> TYPE: PRT
<213> ORGANISM: Plasmodium falciparum

<400> SEQUENCE: 15

Met Asn Lys Asn Ile Leu Trp Ile Thr Phe Phe Tyr Phe Leu Phe Phe
1               5                   10                  15

Leu Leu Asp Met Tyr Gln Gly Asn Asp Ala Ile Pro Ser Lys Glu Lys
            20                  25                  30

Lys Asn Asp Pro Glu Ala Asp Ser Lys Asn Ser Gln Asn Gln His Asp
        35                  40                  45

Ile Asn Lys Thr His His Thr Asn Asn Tyr Asp Leu Asn Ile Lys
    50                  55                  60

Asp Lys Asp Glu Lys Lys Arg Lys Asn Asp Asn Leu Ile Asn Asn Tyr
65                  70                  75                  80

Leu Tyr Ser Leu Leu Lys Leu Ser Tyr Asn Lys Asn Gln Asp Ile Tyr
                85                  90                  95

Lys Asn Ile Gln Asn Gly Gln Lys Leu Lys Thr Asp Ile Ile Leu Asn
            100                 105                 110

Ser Phe Val Gln Ile Asn Ser Ser Asn Ile Leu Met Asp Glu Ile Glu
        115                 120                 125

Asn Tyr Val Lys Lys Tyr Thr Glu Ser Asn Arg Ile Met Tyr Leu Gln
    130                 135                 140

Phe Lys Tyr Ile Tyr Leu Gln Ser Leu Asn Ile Thr Val Ser Phe Val
145                 150                 155                 160

Pro Pro Asn Ser Pro Phe Arg Ser Tyr Tyr Asp Lys Asn Leu Asn Lys
                165                 170                 175

Asp Ile Asn Glu Thr Cys His Ser Ile Gln Thr Leu Leu Asn Asn Leu
            180                 185                 190

Ile Ser Ser Lys Ile Ile Phe Lys Met Leu Glu Thr Thr Lys Glu Gln
        195                 200                 205

Ile Leu Leu Leu Trp Asn Asn Lys Lys Ile Ser Gln Gln Asn Tyr Asn
    210                 215                 220

Gln Glu Asn Gln Glu Lys Ser Lys Met Ile Asp Ser Glu Asn Glu Lys
```

```
            225                 230                 235                 240

Leu Glu Lys Tyr Thr Asn Lys Phe Glu His Asn Ile Lys Pro His Ile
                245                 250                 255

Glu Asp Ile Glu Lys Val Asn Glu Tyr Ile Asn Asn Ser Asp Cys
            260                 265                 270

His Leu Thr Cys Ser Lys Tyr Lys Thr Ile Ile Asn Asn Tyr Ile Asp
                275                 280                 285

Glu Ile Ile Thr Thr Asn Thr Asn Ile Tyr Glu Asn Lys Tyr Asn Leu
            290                 295                 300

Pro Gln Glu Arg Ile Ile Lys Asn Tyr Asn His Asn Gly Ile Asn Asn
305                 310                 315                 320

Asp Asp Asn Phe Ile Glu Tyr Asn Ile Leu Asn Ala Asp Pro Asp Leu
                325                 330                 335

Arg Ser His Phe Thr Thr Leu Leu Val Ser Arg Lys Gln Leu Ile Tyr
                340                 345                 350

Ile Glu Tyr Ile Tyr Phe Ile Asn Lys His Ile Val Asn Lys Ile Gln
            355                 360                 365

Glu Asn Phe Lys Leu Asn Gln Asn Lys Tyr Ile His Phe Ile Asn Ser
            370                 375                 380

Asn Asn Ala Val Asn Ala Lys Glu Tyr Glu Tyr Ile Ile Lys Tyr
385                 390                 395                 400

Tyr Thr Thr Phe Lys Tyr Leu Gln Thr Leu Asn Lys Ser Leu Tyr Asp
                405                 410                 415

Ser Ile Tyr Lys His Lys Ile Asn Asn Tyr Ser His Asn Ile Glu Asp
            420                 425                 430

Leu Ile Asn Gln Leu Gln His Lys Ile Asn Asn Leu Met Ile Ile Ser
            435                 440                 445

Phe Asp Lys Asn Lys Ser Ser Asp Leu Met Leu Gln Cys Thr Asn Ile
450                 455                 460

Lys Lys Tyr Thr Asp Asp Ile Cys Leu Ser Ile Lys Pro Lys Ala Leu
465                 470                 475                 480

Glu Val Glu Tyr Leu Arg Asn Ile Asn Lys His Ile Asn Lys Asn Glu
                485                 490                 495

Phe Leu Asn Lys Phe Met Gln Asn Glu Thr Phe Lys Lys Asn Ile Asp
                500                 505                 510

Asp Lys Ile Lys Glu Met Asn Asn Ile Tyr Asp Asn Ile Tyr Ile Ile
            515                 520                 525

Leu Lys Gln Lys Phe Leu Asn Lys Leu Asn Glu Ile Ile Gln Asn His
            530                 535                 540

Lys Asn Lys Gln Glu Thr Lys Leu Asn Thr Thr Thr Ile Gln Glu Leu
545                 550                 555                 560

Leu Gln Leu Leu Lys Asp Ile Lys Glu Ile Gln Thr Lys Gln Ile Asp
                565                 570                 575

Thr Lys Ile Asn Thr Phe Asn Met Tyr Tyr Asn Asp Ile Gln Gln Ile
                580                 585                 590

Lys Ile Lys Ile Asn Gln Asn Glu Lys Glu Ile Lys Lys Val Leu Pro
            595                 600                 605

Gln Leu Tyr Ile Pro Lys Asn Glu Gln Glu Tyr Ile Gln Ile Tyr Lys
            610                 615                 620

Asn Glu Leu Lys Asp Arg Ile Lys Glu Thr Gln Thr Lys Ile Asn Leu
625                 630                 635                 640

Glu Lys Gln Ile Leu Glu Leu Lys Glu Lys Glu His Tyr Ile Thr Asn
                645                 650                 655
```

```
Lys His Thr Tyr Leu Asn Phe Thr His Lys Thr Ile Gln Gln Ile Leu
                660                 665                 670

Gln Gln Gln Tyr Lys Asn Asn Thr Gln Glu Lys Asn Thr Leu Ala Gln
            675                 680                 685

Phe Leu Tyr Asn Ala Asp Ile Lys Lys Tyr Ile Asp Glu Leu Ile Pro
    690                 695                 700

Ile Thr Gln Gln Ile Gln Thr Lys Met Tyr Thr Thr Asn Asn Ile Glu
705                 710                 715                 720

His Ile Lys Gln Ile Leu Ile Asn Tyr Ile Gln Glu Cys Lys Pro Ile
                725                 730                 735

Gln Asn Ile Ser Glu His Thr Thr Tyr Thr Leu Tyr Gln Glu Ile Lys
            740                 745                 750

Thr Asn Leu Glu Asn Ile Glu Gln Lys Ile Met Gln Asn Ile Gln Gln
        755                 760                 765

Thr Thr Asn Arg Leu Lys Ile Asn Ile Lys Lys Ile Phe Asp Gln Ile
    770                 775                 780

Asn Gln Lys Tyr Asp Asp Leu Thr Lys Asn Ile Asn Gln Met Asn Asp
785                 790                 795                 800

Glu Lys Ile Gly Leu Arg Gln Met Glu Asn Arg Leu Lys Gly Lys Tyr
                805                 810                 815

Glu Glu Ile Lys Lys Ala Asn Leu Gln Asp Arg Asp Ile Lys Tyr Ile
            820                 825                 830

Val Gln Asn Asn Asp Ala Asn Asn Asn Asn Asn Ile Ile Ile Ile
        835                 840                 845

Asn Gly Asn Asn Gln Thr Gly Asp Tyr Asn His Ile Leu Phe Asp Tyr
    850                 855                 860

Thr His Leu Trp Asp Asn Ala Gln Phe Thr Arg Thr Lys Glu Asn Ile
865                 870                 875                 880

Asn Asn Leu Lys Asp Asn Ile Gln Ile Asn Ile Asn Ile Lys Ser
                885                 890                 895

Ile Ile Arg Asn Leu Gln Asn Glu Leu Asn Asn Tyr Asn Thr Leu Lys
            900                 905                 910

Ser Asn Ser Ile His Ile Tyr Asp Lys Ile His Thr Leu Glu Glu Leu
        915                 920                 925

Lys Ile Leu Thr Gln Glu Ile Asn Asp Lys Asn Val Ile Arg Lys Ile
    930                 935                 940

Tyr Asp Ile Glu Thr Ile Tyr Gln Asn Asp Leu His Asn Ile Glu Glu
945                 950                 955                 960

Ile Ile Lys Asn Ile Thr Ser Ile Tyr Tyr Lys Ile Asn Ile Leu Asn
                965                 970                 975

Ile Leu Ile Ile Cys Ile Lys Gln Thr Tyr Asn Asn Lys Ser Ile
            980                 985                 990

Glu Ser Leu Lys Leu Lys Ile Asn Asn Leu Thr Asn Ser Thr Gln Glu
        995                 1000                1005

Tyr Ile Asn Gln Ile Lys Ala Ile Pro Thr Asn Leu Leu Pro Glu His
    1010                1015                1020

Ile Lys Gln Lys Ser Val Ser Glu Leu Asn Ile Tyr Met Lys Gln Ile
1025                1030                1035                1040

Tyr Asp Lys Leu Asn Glu His Val Ile Asn Asn Leu Tyr Thr Lys Ser
                1045                1050                1055

Lys Asp Ser Leu Gln Phe Tyr Ile Asn Glu Lys Asn Tyr Asn Asn Asn
            1060                1065                1070
```

His Asp Asp His Asn Asp Asp His Asn Asp Val Tyr Asn Asp Ile Lys
         1075                1080                1085

Glu Asn Glu Ile Tyr Lys Asn Asn Lys Leu Tyr Glu Cys Ile Gln Ile
    1090                1095                1100

Lys Lys Asp Val Asp Glu Leu Tyr Asn Ile Tyr Asp Gln Leu Phe Lys
1105            1110                1115                1120

Asn Ile Ser Gln Asn Tyr Asn Asn His Ser Leu Ser Phe Val His Ser
        1125                1130                1135

Ile Asn Asn His Met Leu Ser Ile Phe Gln Asp Thr Lys Tyr Gly Lys
            1140                1145                1150

His Lys Asn Gln Gln Ile Leu Ser Asp Ile Glu Asn Ile Ile Lys Gln
        1155                1160                1165

Asn Glu His Thr Glu Ser Tyr Lys Asn Leu Asp Thr Ser Asn Ile Gln
    1170                1175                1180

Leu Ile Lys Glu Gln Ile Lys Tyr Phe Leu Gln Ile Phe His Ile Leu
1185            1190                1195                1200

Gln Glu Asn Ile Thr Thr Phe Glu Asn Gln Tyr Lys Asp Leu Ile Ile
            1205                1210                1215

Lys Met Asn His Lys Ile Asn Asn Leu Lys Asp Ile Thr His Ile
        1220                1225                1230

Val Ile Asn Asp Asn Asn Thr Leu Gln Glu Gln Asn Arg Ile Tyr Asn
    1235                1240                1245

Glu Leu Gln Asn Lys Ile Lys Gln Ile Lys Asn Val Ser Asp Val Phe
    1250                1255                1260

Thr His Asn Ile Asn Tyr Ser Gln Gln Ile Leu Asn Tyr Ser Gln Ala
1265            1270                1275                1280

Gln Asn Ser Phe Phe Asn Ile Phe Met Lys Phe Gln Asn Ile Asn Asn
            1285                1290                1295

Asp Ile Asn Ser Lys Arg Tyr Asn Val Gln Lys Lys Ile Thr Glu Ile
        1300                1305                1310

Ile Asn Ser Tyr Asp Ile Ile Asn Tyr Asn Lys Asn Ile Lys Asp
        1315                1320                1325

Ile Tyr Gln Gln Phe Lys Asn Ile Gln Gln Gln Leu Asn Thr Thr Glu
    1330                1335                1340

Thr Gln Leu Asn His Ile Lys Gln Asn Ile Asn His Phe Lys Tyr Phe
1345            1350                1355                1360

Tyr Glu Ser His Gln Thr Ile Ser Ile Val Lys Asn Met Gln Asn Glu
            1365                1370                1375

Lys Leu Lys Ile Gln Glu Phe Asn Lys Lys Ile Gln His Phe Lys Glu
        1380                1385                1390

Glu Thr Gln Ile Met Ile Asn Lys Leu Ile Gln Pro Ser His Ile His
        1395                1400                1405

Leu His Lys Met Lys Leu Pro Ile Thr Gln Gln Gln Leu Asn Thr Ile
    1410                1415                1420

Leu His Arg Asn Glu Gln Thr Lys Asn Ala Thr Arg Ser Tyr Asn Met
1425            1430                1435                1440

Asn Glu Glu Glu Asn Glu Met Gly Tyr Gly Ile Thr Asn Lys Arg Lys
            1445                1450                1455

Asn Ser Glu Thr Asn Asp Met Ile Asn Thr Thr Ile Gly Asp Lys Thr
        1460                1465                1470

Asn Val Leu Lys Asn Asp Asp Gln Glu Lys Gly Lys Arg Gly Thr Ser
    1475                1480                1485

Arg Asn Asn Asn Ile His Thr Asn Glu Asn Asn Ile Asn Asn Glu His

```
    1490                1495                1500

Thr Asn Glu Asn Asn Ile Asn Asn Glu His Thr Asn Glu Lys Asn Ile
1505                1510                1515                1520

Asn Asn Glu His Ala Asn Glu Lys Asn Ile Tyr Asn Glu His Thr Asn
                1525                1530                1535

Glu Asn Asn Ile Asn Tyr Glu His Pro Asn Asn Tyr Gln Gln Lys Asn
            1540                1545                1550

Asp Glu Lys Ile Ser Leu Gln His Lys Thr Ile Asn Thr Ser Gln Arg
        1555                1560                1565

Thr Ile Asp Asp Ser Asn Met Asp Arg Asn Asn Arg Tyr Asn Thr Ser
    1570                1575                1580

Ser Gln Gln Lys Asn Asn Leu His Thr Asn Asn Asn Ser Asn Ser Arg
1585                1590                1595                1600

Tyr Asn Asn Asn His Asp Lys Gln Asn Glu His Lys Tyr Asn Gln Gly
                1605                1610                1615

Lys Ser Ser Gly Lys Asp Asn Ala Tyr Tyr Arg Ile Phe Tyr Ala Gly
            1620                1625                1630

Gly Ile Thr Ala Val Leu Leu Leu Cys Ser Ser Thr Ala Phe Phe Phe
        1635                1640                1645

Ile Lys Asn Ser Asn Glu Pro His His Ile Phe Asn Ile Phe Gln Lys
    1650                1655                1660

Glu Phe Ser Glu Ala Asp Asn Ala His Ser Glu Glu Lys Glu Glu Tyr
1665                1670                1675                1680

Leu Pro Val Tyr Phe Asp Glu Val Glu Asp Glu Val Glu Asp Glu Val
                1685                1690                1695

Glu Asp Glu Asp Glu Asn Glu Asn Glu Val Glu Asn Glu Asn Glu Asp
            1700                1705                1710

Phe Asn Asp Ile
        1715

<210> SEQ ID NO 16
<211> LENGTH: 739
<212> TYPE: PRT
<213> ORGANISM: Artificial Sequence
<220> FEATURE:
<223> OTHER INFORMATION: plasmodium falciparum pfRh4 antigenic fragment

<400> SEQUENCE: 16

Pro Ser Lys Glu Lys Lys Asn Asp Pro Glu Ala Asp Ser Lys Asn Ser
1               5                   10                  15

Gln Asn Gln His Asp Ile Asn Lys Thr His His Thr Asn Asn Asn Tyr
            20                  25                  30

Asp Leu Asn Ile Lys Asp Lys Asp Glu Lys Lys Arg Lys Asn Asp Asn
        35                  40                  45

Leu Ile Asn Asn Tyr Leu Tyr Ser Leu Leu Lys Leu Ser Tyr Asn Lys
    50                  55                  60

Asn Gln Asp Ile Tyr Lys Asn Ile Gln Asn Gly Gln Lys Leu Lys Thr
65                  70                  75                  80

Asp Ile Ile Leu Asn Ser Phe Val Gln Ile Asn Ser Ser Asn Ile Leu
                85                  90                  95

Met Asp Glu Ile Glu Asn Tyr Val Lys Lys Tyr Thr Glu Ser Asn Arg
            100                 105                 110

Ile Met Tyr Leu Gln Phe Lys Tyr Ile Tyr Leu Gln Ser Leu Asn Ile
        115                 120                 125

Thr Val Ser Phe Val Pro Pro Asn Ser Pro Phe Arg Ser Tyr Tyr Asp
```

```
            130                 135                 140
Lys Asn Leu Asn Lys Asp Ile Asn Glu Thr Cys His Ser Ile Gln Thr
145                 150                 155                 160

Leu Leu Asn Asn Leu Ile Ser Ser Lys Ile Ile Phe Lys Met Leu Glu
                165                 170                 175

Thr Thr Lys Glu Gln Ile Leu Leu Trp Asn Asn Lys Lys Ile Ser
            180                 185                 190

Gln Gln Asn Tyr Asn Gln Glu Asn Gln Glu Lys Ser Lys Met Ile Asp
                195                 200                 205

Ser Glu Asn Glu Lys Leu Glu Lys Tyr Thr Asn Lys Phe Glu His Asn
210                 215                 220

Ile Lys Pro His Ile Glu Asp Ile Glu Lys Lys Val Asn Glu Tyr Ile
225                 230                 235                 240

Asn Asn Ser Asp Cys His Leu Thr Cys Ser Lys Tyr Lys Thr Ile Ile
                245                 250                 255

Asn Asn Tyr Ile Asp Glu Ile Ile Thr Thr Asn Thr Asn Ile Tyr Glu
                260                 265                 270

Asn Lys Tyr Asn Leu Pro Gln Glu Arg Ile Ile Lys Asn Tyr Asn His
            275                 280                 285

Asn Gly Ile Asn Asn Asp Asp Asn Phe Ile Glu Tyr Asn Ile Leu Asn
            290                 295                 300

Ala Asp Pro Asp Leu Arg Ser His Phe Thr Thr Leu Leu Val Ser Arg
305                 310                 315                 320

Lys Gln Leu Ile Tyr Ile Glu Tyr Ile Tyr Phe Ile Asn Lys His Ile
                325                 330                 335

Val Asn Lys Ile Gln Glu Asn Phe Lys Leu Asn Gln Asn Lys Tyr Ile
                340                 345                 350

His Phe Ile Asn Ser Asn Asn Ala Val Asn Ala Ala Lys Glu Tyr Glu
            355                 360                 365

Tyr Ile Ile Lys Tyr Tyr Thr Thr Phe Lys Tyr Leu Gln Thr Leu Asn
            370                 375                 380

Lys Ser Leu Tyr Asp Ser Ile Tyr Lys His Lys Ile Asn Asn Tyr Ser
385                 390                 395                 400

His Asn Ile Glu Asp Leu Ile Asn Gln Leu Gln His Lys Ile Asn Asn
                405                 410                 415

Leu Met Ile Ile Ser Phe Asp Lys Asn Lys Ser Ser Asp Leu Met Leu
                420                 425                 430

Gln Cys Thr Asn Ile Lys Lys Tyr Thr Asp Asp Ile Cys Leu Ser Ile
            435                 440                 445

Lys Pro Lys Ala Leu Glu Val Glu Tyr Leu Arg Asn Ile Asn Lys His
450                 455                 460

Ile Asn Lys Asn Glu Phe Leu Asn Lys Phe Met Gln Asn Glu Thr Phe
465                 470                 475                 480

Lys Lys Asn Ile Asp Asp Lys Ile Lys Glu Met Asn Asn Ile Tyr Asp
                485                 490                 495

Asn Ile Tyr Ile Ile Leu Lys Gln Lys Phe Leu Asn Lys Leu Asn Glu
                500                 505                 510

Ile Ile Gln Asn His Lys Asn Lys Gln Glu Thr Lys Leu Asn Thr Thr
            515                 520                 525

Thr Ile Gln Glu Leu Leu Gln Leu Leu Lys Asp Ile Lys Glu Ile Gln
            530                 535                 540

Thr Lys Gln Ile Asp Thr Lys Ile Asn Thr Phe Asn Met Tyr Tyr Asn
545                 550                 555                 560
```

```
Asp Ile Gln Gln Ile Lys Ile Lys Ile Asn Gln Asn Glu Lys Glu Ile
                565                 570                 575

Lys Lys Val Leu Pro Gln Leu Tyr Ile Pro Lys Asn Glu Gln Glu Tyr
            580                 585                 590

Ile Gln Ile Tyr Lys Asn Glu Leu Lys Asp Arg Ile Lys Glu Thr Gln
            595                 600                 605

Thr Lys Ile Asn Leu Glu Lys Gln Ile Leu Glu Leu Lys Glu Lys Glu
        610                 615                 620

His Tyr Ile Thr Asn Lys His Thr Tyr Leu Asn Phe Thr His Lys Thr
625                 630                 635                 640

Ile Gln Gln Ile Leu Gln Gln Tyr Lys Asn Thr Gln Glu Lys
                645                 650                 655

Asn Thr Leu Ala Gln Phe Leu Tyr Asn Ala Asp Ile Lys Lys Tyr Ile
            660                 665                 670

Asp Glu Leu Ile Pro Ile Thr Gln Gln Ile Gln Thr Lys Met Tyr Thr
        675                 680                 685

Thr Asn Asn Ile Glu His Ile Lys Gln Ile Leu Ile Asn Tyr Ile Gln
        690                 695                 700

Glu Cys Lys Pro Ile Gln Asn Ile Ser Glu His Thr Thr Tyr Thr Leu
705                 710                 715                 720

Tyr Gln Glu Ile Lys Thr Asn Leu Glu Asn Ile Glu Gln Lys Ile Met
                725                 730                 735

Gln Asn Ile

<210> SEQ ID NO 17
<211> LENGTH: 526
<212> TYPE: PRT
<213> ORGANISM: Plasmodium falciparum

<400> SEQUENCE: 17

Met Ile Arg Ile Lys Lys Lys Leu Ile Leu Thr Ile Ile Tyr Ile His
1               5                   10                  15

Leu Phe Ile Leu Asn Arg Leu Ser Phe Glu Asn Ala Ile Lys Lys Thr
            20                  25                  30

Lys Asn Gln Glu Asn Asn Leu Thr Leu Leu Pro Ile Lys Ser Thr Glu
        35                  40                  45

Glu Glu Lys Asp Asp Ile Lys Asn Gly Lys Asp Ile Lys Glu Ile
    50                  55                  60

Asp Asn Asp Lys Glu Asn Ile Lys Thr Asn Asn Ala Lys Asp His Ser
65                  70                  75                  80

Thr Tyr Ile Lys Ser Tyr Leu Asn Thr Asn Val Asn Asp Gly Leu Lys
                85                  90                  95

Tyr Leu Phe Ile Pro Ser His Asn Ser Phe Ile Lys Lys Tyr Ser Val
            100                 105                 110

Phe Asn Gln Ile Asn Asp Gly Met Leu Leu Asn Glu Lys Asn Asp Val
        115                 120                 125

Lys Asn Asn Glu Asp Tyr Lys Asn Val Asp Tyr Lys Asn Val Asn Phe
    130                 135                 140

Leu Gln Tyr His Phe Lys Glu Leu Ser Asn Tyr Asn Ile Ala Asn Ser
145                 150                 155                 160

Ile Asp Ile Leu Gln Glu Lys Glu Gly His Leu Asp Phe Val Ile Ile
                165                 170                 175

Pro His Tyr Thr Phe Leu Asp Tyr Tyr Lys His Leu Ser Tyr Asn Ser
            180                 185                 190
```

```
Ile Tyr His Lys Ser Ser Thr Tyr Gly Lys Cys Ile Ala Val Asp Ala
        195                 200                 205

Phe Ile Lys Lys Ile Asn Glu Thr Tyr Asp Lys Val Lys Ser Lys Cys
    210                 215                 220

Asn Asp Ile Lys Asn Asp Leu Ile Ala Thr Ile Lys Lys Leu Glu His
225                 230                 235                 240

Pro Tyr Asp Ile Asn Asn Lys Asn Asp Asp Ser Tyr Arg Tyr Asp Ile
                245                 250                 255

Ser Glu Glu Ile Asp Asp Lys Ser Glu Glu Thr Asp Asp Glu Thr Glu
            260                 265                 270

Glu Val Glu Asp Ser Ile Gln Asp Thr Asp Ser Asn His Thr Pro Ser
        275                 280                 285

Asn Lys Lys Lys Asn Asp Leu Met Asn Arg Thr Phe Lys Lys Met Met
    290                 295                 300

Asp Glu Tyr Asn Thr Lys Lys Lys Lys Leu Ile Lys Cys Ile Lys Asn
305                 310                 315                 320

His Glu Asn Asp Phe Asn Lys Ile Cys Met Asp Met Lys Asn Tyr Gly
                325                 330                 335

Thr Asn Leu Phe Glu Gln Leu Ser Cys Tyr Asn Asn Asn Phe Cys Asn
            340                 345                 350

Thr Asn Gly Ile Arg Tyr His Tyr Asp Glu Tyr Ile His Lys Leu Ile
        355                 360                 365

Leu Ser Val Lys Ser Lys Asn Leu Asn Lys Asp Leu Ser Asp Met Thr
    370                 375                 380

Asn Ile Leu Gln Gln Ser Glu Leu Leu Leu Thr Asn Leu Asn Lys Lys
385                 390                 395                 400

Met Gly Ser Tyr Ile Tyr Ile Asp Thr Ile Lys Phe Ile His Lys Glu
                405                 410                 415

Met Lys His Ile Phe Asn Arg Ile Glu Tyr His Thr Lys Ile Ile Asn
            420                 425                 430

Asp Lys Thr Lys Ile Ile Gln Asp Lys Ile Lys Leu Asn Ile Trp Arg
        435                 440                 445

Thr Phe Gln Lys Asp Glu Leu Leu Lys Arg Ile Leu Asp Met Ser Asn
    450                 455                 460

Glu Tyr Ser Leu Phe Ile Thr Ser Asp His Leu Arg Gln Met Leu Tyr
465                 470                 475                 480

Asn Thr Phe Tyr Ser Lys Glu Lys His Leu Asn Asn Ile Phe His His
                485                 490                 495

Leu Ile Tyr Val Leu Gln Met Lys Phe Asn Asp Val Pro Ile Lys Met
            500                 505                 510

Glu Tyr Phe Gln Thr Tyr Lys Lys Asn Lys Pro Leu Thr Gln
        515                 520                 525
```

```
<210> SEQ ID NO 18
<211> LENGTH: 503
<212> TYPE: PRT
<213> ORGANISM: Artificial Sequence
<220> FEATURE:
<223> OTHER INFORMATION: plasmodium falciparum Rh5 antigenic fragment

<400> SEQUENCE: 18

Ser Phe Glu Asn Ala Ile Lys Lys Thr Lys Asn Gln Glu Asn Asn Leu
1               5                   10                  15

Thr Leu Leu Pro Ile Lys Ser Thr Glu Glu Glu Lys Asp Asp Ile Lys
            20                  25                  30
```

-continued

```
Asn Gly Lys Asp Ile Lys Lys Glu Ile Asp Asn Asp Lys Glu Asn Ile
        35                  40                  45
Lys Thr Asn Asn Ala Lys Asp His Ser Thr Tyr Ile Lys Ser Tyr Leu
    50                  55                  60
Asn Thr Asn Val Asn Asp Gly Leu Lys Tyr Leu Phe Ile Pro Ser His
65                  70                  75                  80
Asn Ser Phe Ile Lys Lys Tyr Ser Val Phe Asn Gln Ile Asn Asp Gly
                85                  90                  95
Met Leu Leu Asn Glu Lys Asn Asp Val Lys Asn Asn Glu Asp Tyr Lys
                100                 105                 110
Asn Val Asp Tyr Lys Asn Val Asn Phe Leu Gln Tyr His Phe Lys Glu
            115                 120                 125
Leu Ser Asn Tyr Asn Ile Ala Asn Ser Ile Asp Ile Leu Gln Glu Lys
        130                 135                 140
Glu Gly His Leu Asp Phe Val Ile Ile Pro His Tyr Thr Phe Leu Asp
145                 150                 155                 160
Tyr Tyr Lys His Leu Ser Tyr Asn Ser Ile Tyr His Lys Ser Ser Thr
                165                 170                 175
Tyr Gly Lys Cys Ile Ala Val Asp Ala Phe Ile Lys Lys Ile Asn Glu
                180                 185                 190
Thr Tyr Asp Lys Val Lys Ser Lys Cys Asn Asp Ile Lys Asn Asp Leu
            195                 200                 205
Ile Ala Thr Ile Lys Lys Leu Glu His Pro Tyr Asp Ile Asn Asn Lys
        210                 215                 220
Asn Asp Asp Ser Tyr Arg Tyr Asp Ile Ser Glu Ile Asp Asp Lys
225                 230                 235                 240
Ser Glu Glu Thr Asp Asp Glu Thr Glu Val Glu Asp Ser Ile Gln
                245                 250                 255
Asp Thr Asp Ser Asn His Thr Pro Ser Asn Lys Lys Asn Asp Leu
            260                 265                 270
Met Asn Arg Thr Phe Lys Lys Met Met Asp Glu Tyr Asn Thr Lys Lys
        275                 280                 285
Lys Lys Leu Ile Lys Cys Ile Lys Asn His Glu Asn Asp Phe Asn Lys
        290                 295                 300
Ile Cys Met Asp Met Lys Asn Tyr Gly Thr Asn Leu Phe Glu Gln Leu
305                 310                 315                 320
Ser Cys Tyr Asn Asn Asn Phe Cys Asn Thr Asn Gly Ile Arg Tyr His
                325                 330                 335
Tyr Asp Glu Tyr Ile His Lys Leu Ile Leu Ser Val Lys Ser Lys Asn
            340                 345                 350
Leu Asn Lys Asp Leu Ser Asp Met Thr Asn Ile Leu Gln Gln Ser Glu
        355                 360                 365
Leu Leu Leu Thr Asn Leu Asn Lys Lys Met Gly Ser Tyr Ile Tyr Ile
    370                 375                 380
Asp Thr Ile Lys Phe Ile His Lys Glu Met Lys His Ile Phe Asn Arg
385                 390                 395                 400
Ile Glu Tyr His Thr Lys Ile Ile Asn Asp Lys Thr Lys Ile Ile Gln
                405                 410                 415
Asp Lys Ile Lys Leu Asn Ile Trp Arg Thr Phe Gln Lys Asp Glu Leu
            420                 425                 430
Leu Lys Arg Ile Leu Asp Met Ser Asn Glu Tyr Ser Leu Phe Ile Thr
        435                 440                 445
```

-continued

```
Ser Asp His Leu Arg Gln Met Leu Tyr Asn Thr Phe Tyr Ser Lys Glu
    450                 455                 460
Lys His Leu Asn Asn Ile Phe His His Leu Ile Tyr Val Leu Gln Met
465                 470                 475                 480
Lys Phe Asn Asp Val Pro Ile Lys Met Glu Tyr Phe Gln Thr Tyr Lys
                485                 490                 495
Lys Asn Lys Pro Leu Thr Gln
            500

<210> SEQ ID NO 19
<211> LENGTH: 379
<212> TYPE: PRT
<213> ORGANISM: Artificial Sequence
<220> FEATURE:
<223> OTHER INFORMATION: plasmodium falciparum Rh5 antigenic fragment

<400> SEQUENCE: 19

His Phe Lys Glu Leu Ser Asn Tyr Asn Ile Ala Asn Ser Ile Asp Ile
1               5                   10                  15

Leu Gln Glu Lys Glu Gly His Leu Asp Phe Val Ile Ile Pro His Tyr
            20                  25                  30

Thr Phe Leu Asp Tyr Tyr Lys His Leu Ser Tyr Asn Ser Ile Tyr His
        35                  40                  45

Lys Ser Ser Thr Tyr Gly Lys Cys Ile Ala Val Asp Ala Phe Ile Lys
    50                  55                  60

Lys Ile Asn Glu Thr Tyr Asp Lys Val Lys Ser Lys Cys Asn Asp Ile
65                  70                  75                  80

Lys Asn Asp Leu Ile Ala Thr Ile Lys Lys Leu Glu His Pro Tyr Asp
                85                  90                  95

Ile Asn Asn Lys Asn Asp Asp Ser Tyr Arg Tyr Asp Ile Ser Glu Glu
            100                 105                 110

Ile Asp Asp Lys Ser Glu Glu Thr Asp Asp Glu Thr Glu Glu Val Glu
        115                 120                 125

Asp Ser Ile Gln Asp Thr Asp Ser Asn His Thr Pro Ser Asn Lys Lys
    130                 135                 140

Lys Asn Asp Leu Met Asn Arg Thr Phe Lys Lys Met Met Asp Glu Tyr
145                 150                 155                 160

Asn Thr Lys Lys Lys Lys Leu Ile Lys Cys Ile Lys Asn His Glu Asn
                165                 170                 175

Asp Phe Asn Lys Ile Cys Met Asp Met Lys Asn Tyr Gly Thr Asn Leu
            180                 185                 190

Phe Glu Gln Leu Ser Cys Tyr Asn Asn Asn Phe Cys Asn Thr Asn Gly
        195                 200                 205

Ile Arg Tyr His Tyr Asp Glu Tyr Ile His Lys Leu Ile Leu Ser Val
    210                 215                 220

Lys Ser Lys Asn Leu Asn Lys Asp Leu Ser Asp Met Thr Asn Ile Leu
225                 230                 235                 240

Gln Gln Ser Glu Leu Leu Leu Thr Asn Leu Asn Lys Lys Met Gly Ser
                245                 250                 255

Tyr Ile Tyr Ile Asp Thr Ile Lys Phe Ile His Lys Glu Met Lys His
            260                 265                 270

Ile Phe Asn Arg Ile Glu Tyr His Thr Lys Ile Ile Asn Asp Lys Thr
        275                 280                 285

Lys Ile Ile Gln Asp Lys Ile Lys Leu Asn Ile Trp Arg Thr Phe Gln
    290                 295                 300
```

```
Lys Asp Glu Leu Leu Lys Arg Ile Leu Asp Met Ser Asn Glu Tyr Ser
305                 310                 315                 320

Leu Phe Ile Thr Ser Asp His Leu Arg Gln Met Leu Tyr Asn Thr Phe
                325                 330                 335

Tyr Ser Lys Glu Lys His Leu Asn Asn Ile Phe His His Leu Ile Tyr
            340                 345                 350

Val Leu Gln Met Lys Phe Asn Asp Val Pro Ile Lys Met Glu Tyr Phe
        355                 360                 365

Gln Thr Tyr Lys Lys Asn Lys Pro Leu Thr Gln
    370                 375

<210> SEQ ID NO 20
<211> LENGTH: 384
<212> TYPE: PRT
<213> ORGANISM: Artificial Sequence
<220> FEATURE:
<223> OTHER INFORMATION: plasmodium falciparum Rh5 antigenic fragment

<400> SEQUENCE: 20

Asn Phe Leu Gln Tyr His Phe Lys Glu Leu Ser Asn Tyr Asn Ile Ala
1               5                   10                  15

Asn Ser Ile Asp Ile Leu Gln Glu Lys Glu Gly His Leu Asp Phe Val
            20                  25                  30

Ile Ile Pro His Tyr Thr Phe Leu Asp Tyr Tyr Lys His Leu Ser Tyr
        35                  40                  45

Asn Ser Ile Tyr His Lys Ser Ser Thr Tyr Gly Lys Cys Ile Ala Val
    50                  55                  60

Asp Ala Phe Ile Lys Lys Ile Asn Glu Thr Tyr Asp Lys Val Lys Ser
65                  70                  75                  80

Lys Cys Asn Asp Ile Lys Asn Asp Leu Ile Ala Thr Ile Lys Lys Leu
                85                  90                  95

Glu His Pro Tyr Asp Ile Asn Asn Lys Asn Asp Asp Ser Tyr Arg Tyr
            100                 105                 110

Asp Ile Ser Glu Glu Ile Asp Asp Lys Ser Glu Glu Thr Asp Asp Glu
        115                 120                 125

Thr Glu Glu Val Glu Asp Ser Ile Gln Asp Thr Asp Ser Asn His Thr
    130                 135                 140

Pro Ser Asn Lys Lys Lys Asn Asp Leu Met Asn Arg Thr Phe Lys Lys
145                 150                 155                 160

Met Met Asp Glu Tyr Asn Thr Lys Lys Lys Leu Ile Lys Cys Ile
                165                 170                 175

Lys Asn His Glu Asn Asp Phe Asn Lys Ile Cys Met Asp Met Lys Asn
            180                 185                 190

Tyr Gly Thr Asn Leu Phe Glu Gln Leu Ser Cys Tyr Asn Asn Asn Phe
        195                 200                 205

Cys Asn Thr Asn Gly Ile Arg Tyr His Tyr Asp Glu Tyr Ile His Lys
    210                 215                 220

Leu Ile Leu Ser Val Lys Ser Lys Asn Leu Asn Lys Asp Leu Ser Asp
225                 230                 235                 240

Met Thr Asn Ile Leu Gln Gln Ser Glu Leu Leu Leu Thr Asn Leu Asn
                245                 250                 255

Lys Lys Met Gly Ser Tyr Ile Tyr Ile Asp Thr Ile Lys Phe Ile His
            260                 265                 270

Lys Glu Met Lys His Ile Phe Asn Arg Ile Glu Tyr His Thr Lys Ile
        275                 280                 285
```

```
Ile Asn Asp Lys Thr Lys Ile Ile Gln Asp Lys Ile Lys Leu Asn Ile
            290                 295                 300

Trp Arg Thr Phe Gln Lys Asp Glu Leu Leu Lys Arg Ile Leu Asp Met
305                 310                 315                 320

Ser Asn Glu Tyr Ser Leu Phe Ile Thr Ser Asp His Leu Arg Gln Met
                325                 330                 335

Leu Tyr Asn Thr Phe Tyr Ser Lys Glu Lys His Leu Asn Asn Ile Phe
            340                 345                 350

His His Leu Ile Tyr Val Leu Gln Met Lys Phe Asn Asp Val Pro Ile
        355                 360                 365

Lys Met Glu Tyr Phe Gln Thr Tyr Lys Lys Asn Lys Pro Leu Thr Gln
370                 375                 380
```

<210> SEQ ID NO 21
<211> LENGTH: 389
<212> TYPE: PRT
<213> ORGANISM: Artificial Sequence
<220> FEATURE:
<223> OTHER INFORMATION: plasmodium falciparum Rh5 antigenic fragment

<400> SEQUENCE: 21

```
Asp Tyr Lys Asn Val Asn Phe Leu Gln Tyr His Phe Lys Glu Leu Ser
1               5                   10                  15

Asn Tyr Asn Ile Ala Asn Ser Ile Asp Ile Leu Gln Glu Lys Glu Gly
            20                  25                  30

His Leu Asp Phe Val Ile Ile Pro His Tyr Thr Phe Leu Asp Tyr Tyr
        35                  40                  45

Lys His Leu Ser Tyr Asn Ser Ile Tyr His Lys Ser Ser Thr Tyr Gly
    50                  55                  60

Lys Cys Ile Ala Val Asp Ala Phe Ile Lys Lys Ile Asn Glu Thr Tyr
65                  70                  75                  80

Asp Lys Val Lys Ser Lys Cys Asn Asp Ile Leu Asn Asp Leu Ile Ala
                85                  90                  95

Thr Ile Lys Lys Leu Glu His Pro Tyr Asp Ile Asn Asn Lys Asn Asp
            100                 105                 110

Asp Ser Tyr Arg Tyr Asp Ile Ser Glu Glu Ile Asp Asp Lys Ser Glu
        115                 120                 125

Glu Thr Asp Asp Glu Thr Glu Glu Val Glu Asp Ser Ile Gln Asp Thr
    130                 135                 140

Asp Ser Asn His Thr Pro Ser Asn Lys Lys Lys Asn Asp Leu Met Asn
145                 150                 155                 160

Arg Thr Phe Lys Lys Met Met Asp Glu Tyr Asn Thr Lys Lys Lys Lys
                165                 170                 175

Leu Ile Lys Cys Ile Lys Asn His Glu Asn Asp Phe Asn Lys Ile Cys
            180                 185                 190

Met Asp Met Lys Asn Tyr Gly Thr Asn Leu Phe Glu Gln Leu Ser Cys
        195                 200                 205

Tyr Asn Asn Asn Phe Cys Asn Thr Asn Gly Ile Arg Tyr His Tyr Asp
    210                 215                 220

Glu Tyr Ile His Lys Leu Ile Leu Ser Val Lys Ser Lys Asn Leu Asn
225                 230                 235                 240

Lys Asp Leu Ser Asp Met Thr Asn Ile Leu Gln Gln Ser Glu Leu Leu
                245                 250                 255

Leu Thr Asn Leu Asn Lys Lys Met Gly Ser Tyr Ile Tyr Ile Asp Thr
            260                 265                 270
```

```
Ile Lys Phe Ile His Lys Glu Met Lys His Ile Phe Asn Arg Ile Glu
            275                 280                 285

Tyr His Thr Lys Ile Ile Asn Asp Lys Thr Lys Ile Ile Gln Asp Lys
        290                 295                 300

Ile Lys Leu Asn Ile Trp Arg Thr Phe Gln Lys Asp Glu Leu Leu Lys
305                 310                 315                 320

Arg Ile Leu Asp Met Ser Asn Glu Tyr Ser Leu Phe Ile Thr Ser Asp
                325                 330                 335

His Leu Arg Gln Met Leu Tyr Asn Thr Phe Tyr Ser Lys Glu Lys His
            340                 345                 350

Leu Asn Asn Ile Phe His His Leu Ile Tyr Val Leu Gln Met Lys Phe
        355                 360                 365

Asn Asp Val Pro Ile Lys Met Glu Tyr Phe Gln Thr Tyr Lys Lys Asn
    370                 375                 380

Lys Pro Leu Thr Gln
385

<210> SEQ ID NO 22
<211> LENGTH: 374
<212> TYPE: PRT
<213> ORGANISM: Artificial Sequence
<220> FEATURE:
<223> OTHER INFORMATION: plasmodium falciparum Rh5 antigenic fragment

<400> SEQUENCE: 22

Ser Asn Tyr Asn Ile Ala Asn Ser Ile Asp Ile Leu Gln Glu Lys Glu
1               5                   10                  15

Gly His Leu Asp Phe Val Ile Ile Pro His Tyr Thr Phe Leu Asp Tyr
            20                  25                  30

Tyr Lys His Leu Ser Tyr Asn Ser Ile Tyr His Lys Ser Ser Thr Tyr
        35                  40                  45

Gly Lys Cys Ile Ala Val Asp Ala Phe Ile Lys Ile Asn Glu Thr
    50                  55                  60

Tyr Asp Lys Val Lys Ser Lys Cys Asn Asp Ile Lys Asn Asp Leu Ile
65                  70                  75                  80

Ala Thr Ile Lys Lys Leu Glu His Pro Tyr Asp Ile Asn Asn Lys Asn
                85                  90                  95

Asp Asp Ser Tyr Arg Tyr Asp Ile Ser Glu Glu Ile Asp Asp Lys Ser
            100                 105                 110

Glu Glu Thr Asp Asp Glu Thr Glu Glu Val Glu Asp Ser Ile Gln Asp
        115                 120                 125

Thr Asp Ser Asn His Thr Pro Ser Asn Lys Lys Asn Asp Leu Met
130                 135                 140

Asn Arg Thr Phe Lys Lys Met Met Asp Glu Tyr Asn Thr Lys Lys
145                 150                 155                 160

Lys Leu Ile Lys Cys Ile Lys Asn His Glu Asn Asp Phe Asn Lys Ile
                165                 170                 175

Cys Met Asp Met Lys Asn Tyr Gly Thr Asn Leu Phe Glu Gln Leu Ser
            180                 185                 190

Cys Tyr Asn Asn Asn Phe Cys Asn Thr Asn Gly Ile Arg Tyr His Tyr
        195                 200                 205

Asp Glu Tyr Ile His Lys Leu Ile Leu Ser Val Lys Ser Lys Asn Leu
    210                 215                 220

Asn Lys Asp Leu Ser Asp Met Thr Asn Ile Leu Gln Gln Ser Glu Leu
225                 230                 235                 240
```

```
Leu Leu Thr Asn Leu Asn Lys Lys Met Gly Ser Tyr Ile Tyr Ile Asp
                245                 250                 255

Thr Ile Lys Phe Ile His Lys Glu Met Lys His Ile Phe Asn Arg Ile
            260                 265                 270

Glu Tyr His Thr Lys Ile Ile Asn Asp Lys Thr Lys Ile Ile Gln Asp
            275                 280                 285

Lys Ile Lys Leu Asn Ile Trp Arg Thr Phe Gln Lys Asp Glu Leu Leu
        290                 295                 300

Lys Arg Ile Leu Asp Met Ser Asn Glu Tyr Ser Leu Phe Ile Thr Ser
305                 310                 315                 320

Asp His Leu Arg Gln Met Leu Tyr Asn Thr Phe Tyr Ser Lys Glu Lys
                325                 330                 335

His Leu Asn Asn Ile Phe His His Leu Ile Tyr Val Leu Gln Met Lys
            340                 345                 350

Phe Asn Asp Val Pro Ile Lys Met Glu Tyr Phe Gln Thr Tyr Lys Lys
        355                 360                 365

Asn Lys Pro Leu Thr Gln
    370

<210> SEQ ID NO 23
<211> LENGTH: 369
<212> TYPE: PRT
<213> ORGANISM: Artificial Sequence
<220> FEATURE:
<223> OTHER INFORMATION: plasmodium falciparum Rh5 antigenic fragment

<400> SEQUENCE: 23

Ala Asn Ser

```
Asp Met Thr Asn Ile Leu Gln Gln Ser Glu Leu Leu Thr Asn Leu
225                 230                 235                 240

Asn Lys Lys Met Gly Ser Tyr Ile Tyr Ile Asp Thr Ile Lys Phe Ile
            245                 250                 255

His Lys Glu Met Lys His Ile Phe Asn Arg Ile Glu Tyr His Thr Lys
                260                 265                 270

Ile Ile Asn Asp Lys Thr Lys Ile Ile Gln Asp Lys Ile Lys Leu Asn
                275                 280                 285

Ile Trp Arg Thr Phe Gln Lys Asp Glu Leu Leu Lys Arg Ile Leu Asp
        290                 295                 300

Met Ser Asn Glu Tyr Ser Leu Phe Ile Thr Ser Asp His Leu Arg Gln
305                 310                 315                 320

Met Leu Tyr Asn Thr Phe Tyr Ser Lys Glu Lys His Leu Asn Asn Ile
                325                 330                 335

Phe His His Leu Ile Tyr Val Leu Gln Met Lys Phe Asn Asp Val Pro
                340                 345                 350

Ile Lys Met Glu Tyr Phe Gln Thr Tyr Lys Lys Asn Lys Pro Leu Thr
            355                 360                 365

Gln

<210> SEQ ID NO 24
<211> LENGTH: 170
<212> TYPE: PRT
<213> ORGANISM: Artificial Sequence
<220> FEATURE:
<223> OTHER INFORMATION: plasmodium falciparum Rh5 antigenic fragment

<400> SEQUENC

<400> SEQUENCE: 25

Ile Ala Val Asp Ala Phe Ile Lys Lys Ile Asn Glu Thr Tyr Asp Lys
1               5                   10                  15

Val Lys Ser Lys Cys Asn Asp Ile Lys Asn Asp Leu Ile Ala Thr Ile
            20                  25                  30

Lys Lys Leu Glu His Pro Tyr Asp Ile Asn Asn Lys Asn Asp Asp Ser
        35                  40                  45

Tyr Arg Tyr Asp Ile Ser Glu Glu Ile Asp Asp Lys Ser Glu Glu Thr
    50                  55                  60

Asp Asp Glu Thr Glu Glu Val Glu Asp Ser Ile Gln Asp Thr Asp Ser
65              70                  75                  80

Asn His Thr Pro Ser Asn Lys Lys Asn Asp Leu Met Asn Arg Thr
            85                  90                  95

Phe Lys Lys Met Met Asp Glu Tyr Asn Thr Lys Lys Lys Leu Ile
                100                 105                 110

Lys Cys Ile Lys Asn His Glu Asn Asp Phe Asn Lys Ile Cys Met Asp
            115                 120                 125

Met Lys Asn Tyr Gly Thr Asn Leu Phe Glu Gln Leu Ser Cys Tyr Asn
        130                 135                 140

Asn Asn Phe Cys Asn Thr Asn Gly Ile Arg Tyr His Tyr
145                 150                 155

<210> SEQ ID NO 26
<211> LENGTH: 147
<212> TYPE: PRT
<213> ORGANISM: Artificial Sequence
<220> FEATURE:
<223> OTHER INFORMATION: plasmodium falciparum Rh5 antigenic fragment

<400> SEQUENCE: 26

Ile Ala Val Asp Ala Phe Ile Lys Lys Ile Asn Glu Thr Tyr Asp Lys
1               5                   10                  15

Val Lys Ser Lys Cys Asn Asp Ile Lys Asn Asp Leu Ile Ala Thr Ile
            20                  25                  30

Lys Lys Leu Glu His Pro Tyr Asp Ile Asn Asn Lys Asn Asp Asp Ser
        35                  40                  45

Tyr Arg Tyr Asp Ile Ser Glu Glu Ile Asp Asp Lys Ser Glu Glu Thr
    50                  55                  60

Asp Asp Glu Thr Glu Glu Val Glu Asp Ser Ile Gln Asp Thr Asp Ser
65              70                  75                  80

Asn His Thr Pro Ser Asn Lys Lys Asn Asp Leu Met Asn Arg Thr
            85                  90                  95

Phe Lys Lys Met Met Asp Glu Tyr Asn Thr Lys Lys Lys Leu Ile
                100                 105                 110

Lys Cys Ile Lys Asn His Glu Asn Asp Phe Asn Lys Ile Cys Met Asp
            115                 120                 125

Met Lys Asn Tyr Gly Thr Asn Leu Phe Glu Gln Leu Ser Cys Tyr Asn
        130                 135                 140

Asn Asn Phe
145

<210> SEQ ID NO 27
<211> LENGTH: 141
<212> TYPE: PRT
<213> ORGANISM: Artificial Sequence
<220> FEATURE:

<223> OTHER INFORMATION: plasmodium falciparum Rh5 antigenic fragment

<400> SEQUENCE: 27

Ile Ala Val Asp Ala Phe Ile Lys Lys

```
<210> SEQ ID NO 30
<211> LENGTH: 12
<212> TYPE: PRT
<213> ORGANISM: Artificial Sequence
<220> FEATURE:
<223> OTHER INFORMATION: plasmodium falciparum Tryptic peptide

<400> SEQUENCE: 30

Lys Lys Ile Asn Glu Thr Tyr Asp Lys Val Lys Ser
1               5                   10

<210> SEQ ID NO 31
<211> LENGTH: 13
<212> TYPE: PRT
<213> ORGANISM: Artificial Sequence
<220> FEATURE:
<223> OTHER INFORMATION: plasmodium falciparum Tryptic peptide

<400> SEQUENCE: 31

Lys Lys Leu Glu His Pro Tyr Asp Ile Asn Asn Lys Asn
1               5                   10

<210> SEQ ID NO 32
<211> LENGTH: 10
<212> TYPE: PRT
<213> ORGANISM: Artificial Sequence
<220> FEATURE:
<223> OTHER INFORMATION: plasmodium falciparum Tryptic peptide

<400> SEQUENCE: 32

Lys Met Met Asp Glu Tyr Asn Thr Lys Lys
1               5                   10

<210> SEQ ID NO 33
<211> LENGTH: 11
<212> TYPE: PRT
<213> ORGANISM: Artificial Sequence
<220> FEATURE:
<223> OTHER INFORMATION: plasmodium falciparum Tryptic peptide

<400> SEQUENCE: 33

Arg Tyr His Tyr Asp Glu Tyr Ile His Lys Leu
1               5                   10

<210> SEQ ID NO 34
<211> LENGTH: 9
<212> TYPE: PRT
<213> ORGANISM: Artificial Sequence
<220> FEATURE:
<223> OTHER INFORMATION: plasmodium falciparum Tryptic peptide

<400> SEQUENCE: 34

Lys Ile Ile Gln Asp Lys Ile Lys Leu
1               5

<210> SEQ ID NO 35
<211> LENGTH: 1502
<212> TYPE: PRT
<213> ORGANISM: Plasmodium falciparum

<400> SEQUENCE: 35

Met Lys Cys Asn Ile Ser Ile Tyr Phe Phe Ala Ser Phe Phe Val Leu
1               5                   10                  15

Tyr Phe Ala Lys Ala Arg Asn Glu Tyr Asp Ile Lys Glu Asn Glu Lys
                20                  25                  30

Phe Leu Asp Val Tyr Lys Glu Lys Phe Asn Glu Leu Asp Lys Lys Lys
```

-continued

```
                35                  40                  45
Tyr Gly Asn Val Gln Lys Thr Asp Lys Lys Ile Phe Thr Phe Ile Glu
 50                  55                  60
Asn Lys Leu Asp Ile Leu Asn Asn Ser Lys Phe Asn Lys Arg Trp Lys
 65                  70                  75                  80
Ser Tyr Gly Thr Pro Asp Asn Ile Asp Lys Asn Met Ser Leu Ile Asn
                     85                  90                  95
Lys His Asn Asn Glu Glu Met Phe Asn Asn Tyr Gln Ser Phe Leu
                100                 105                 110
Ser Thr Ser Ser Leu Ile Lys Gln Asn Lys Tyr Val Pro Ile Asn Ala
            115                 120                 125
Val Arg Val Ser Arg Ile Leu Ser Phe Leu Asp Ser Arg Ile Asn Asn
        130                 135                 140
Gly Arg Asn Thr Ser Ser Asn Asn Glu Val Leu Ser Asn Cys Arg Glu
145                 150                 155                 160
Lys Arg Lys Gly Met Lys Trp Asp Cys Lys Lys Asn Asp Arg Ser
                    165                 170                 175
Asn Tyr Val Cys Ile Pro Asp Arg Arg Ile Gln Leu Cys Ile Val Asn
                180                 185                 190
Leu Ser Ile Ile Lys Thr Tyr Thr Lys Glu Thr Met Lys Asp His Phe
            195                 200                 205
Ile Glu Ala Ser Lys Lys Glu Ser Gln Leu Leu Leu Lys Lys Asn Asp
        210                 215                 220
Asn Lys Tyr Asn Ser Lys Phe Cys Asn Asp Leu Lys Asn Ser Phe Leu
225                 230                 235                 240
Asp Tyr Gly His Leu Ala Met Gly Asn Asp Met Asp Phe Gly Gly Tyr
                    245                 250                 255
Ser Thr Lys Ala Glu Asn Lys Ile Gln Glu Val Phe Lys Gly Ala His
                260                 265                 270
Gly Glu Ile Ser Glu His Lys Ile Lys Asn Phe Arg Lys Lys Trp Trp
            275                 280                 285
Asn Glu Phe Arg Glu Lys Leu Trp Glu Ala Met Leu Ser Glu His Lys
        290                 295                 300
Asn Asn Ile Asn Asn Cys Lys Asn Ile Pro Gln Glu Glu Leu Gln Ile
305                 310                 315                 320
Thr Gln Trp Ile Lys Glu Trp His Gly Glu Phe Leu Leu Glu Arg Asp
                    325                 330                 335
Asn Arg Ser Lys Leu Pro Lys Ser Lys Cys Lys Asn Asn Thr Leu Tyr
                340                 345                 350
Glu Ala Cys Glu Lys Glu Cys Ile Asp Pro Cys Met Lys Tyr Arg Asp
            355                 360                 365
Trp Ile Ile Arg Ser Lys Phe Glu Trp His Thr Leu Ser Lys Glu Tyr
        370                 375                 380
Glu Thr Gln Lys Val Pro Lys Glu Asn Ala Glu Asn Tyr Leu Ile Lys
385                 390                 395                 400
Ile Ser Glu Asn Lys Asn Asp Ala Lys Val Ser Leu Leu Leu Asn Asn
                    405                 410                 415
Cys Asp Ala Glu Tyr Ser Lys Tyr Cys Asp Cys Lys His Thr Thr Thr
                420                 425                 430
Leu Val Lys Ser Val Leu Asn Gly Asn Asp Asn Thr Ile Lys Glu Lys
            435                 440                 445
Arg Glu His Ile Asp Leu Asp Asp Phe Ser Lys Phe Gly Cys Asp Lys
        450                 455                 460
```

-continued

```
Asn Ser Val Asp Thr Asn Thr Lys Val Trp Glu Cys Lys Lys Pro Tyr
465                 470                 475                 480

Lys Leu Ser Thr Lys Asp Val Cys Val Pro Pro Arg Arg Gln Glu Leu
                485                 490                 495

Cys Leu Gly Asn Ile Asp Arg Ile Tyr Asp Lys Asn Leu Leu Met Ile
            500                 505                 510

Lys Glu His Ile Leu Ala Ile Ala Ile Tyr Glu Ser Arg Ile Leu Lys
        515                 520                 525

Arg Lys Tyr Lys Asn Lys Asp Asp Lys Glu Val Cys Lys Ile Ile Asn
    530                 535                 540

Lys Thr Phe Ala Asp Ile Arg Asp Ile Ile Gly Gly Thr Asp Tyr Trp
545                 550                 555                 560

Asn Asp Leu Ser Asn Arg Lys Leu Val Gly Lys Ile Asn Thr Asn Ser
                565                 570                 575

Asn Tyr Val His Arg Asn Lys Gln Asn Asp Lys Leu Phe Arg Asp Glu
            580                 585                 590

Trp Trp Lys Val Ile Lys Lys Asp Val Trp Asn Val Ile Ser Trp Val
        595                 600                 605

Phe Lys Asp Lys Thr Val Cys Lys Glu Asp Asp Ile Glu Asn Ile Pro
    610                 615                 620

Gln Phe Phe Arg Trp Phe Ser Glu Trp Gly Asp Asp Tyr Cys Gln Asp
625                 630                 635                 640

Lys Thr Lys Met Ile Glu Thr Leu Lys Val Glu Cys Lys Glu Lys Pro
                645                 650                 655

Cys Glu Asp Asp Asn Cys Lys Arg Lys Cys Asn Ser Tyr Lys Glu Trp
            660                 665                 670

Ile Ser Lys Lys Glu Glu Tyr Asn Lys Gln Ala Lys Gln Tyr Gln
        675                 680                 685

Glu Tyr Gln Lys Gly Asn Asn Tyr Lys Met Tyr Ser Glu Phe Lys Ser
    690                 695                 700

Ile Lys Pro Glu Val Tyr Leu Lys Lys Tyr Ser Glu Lys Cys Ser Asn
705                 710                 715                 720

Leu Asn Phe Glu Asp Glu Phe Lys Glu Glu Leu His Ser Asp Tyr Lys
                725                 730                 735

Asn Lys Cys Thr Met Cys Pro Glu Val Lys Asp Val Pro Ile Ser Ile
            740                 745                 750

Ile Arg Asn Asn Glu Gln Thr Ser Gln Glu Ala Val Pro Glu Glu Ser
        755                 760                 765

Thr Glu Ile Ala His Arg Thr Glu Thr Arg Thr Asp Glu Arg Lys Asn
    770                 775                 780

Gln Glu Pro Ala Asn Lys Asp Leu Lys Asn Pro Gln Gln Ser Val Gly
785                 790                 795                 800

Glu Asn Gly Thr Lys Asp Leu Leu Gln Glu Asp Leu Gly Gly Ser Arg
                805                 810                 815

Ser Glu Asp Glu Val Thr Gln Glu Phe Gly Val Asn His Gly Ile Pro
            820                 825                 830

Lys Gly Glu Asp Gln Thr Leu Gly Lys Ser Asp Ala Ile Pro Asn Ile
        835                 840                 845

Gly Glu Pro Glu Thr Gly Ile Ser Thr Glu Glu Ser Arg His Glu
    850                 855                 860

Glu Gly His Asn Lys Gln Ala Leu Ser Thr Ser Val Asp Glu Pro Glu
865                 870                 875                 880
```

```
Leu Ser Asp Thr Leu Gln Leu His Glu Asp Thr Lys Glu Asn Asp Lys
            885                 890                 895

Leu Pro Leu Glu Ser Ser Thr Ile Thr Ser Pro Thr Glu Ser Gly Ser
            900                 905                 910

Ser Asp Thr Glu Glu Thr Pro Ser Ile Ser Glu Gly Pro Lys Gly Asn
            915                 920                 925

Glu Gln Lys Lys Arg Asp Asp Ser Leu Ser Lys Ile Ser Val Ser
        930                 935                 940

Pro Glu Asn Ser Arg Pro Glu Thr Asp Ala Lys Asp Thr Ser Asn Leu
945                 950                 955                 960

Leu Lys Leu Lys Gly Asp Val Asp Ile Ser Met Pro Lys Ala Val Ile
            965                 970                 975

Gly Ser Ser Pro Asn Asp Asn Ile Asn Val Thr Glu Gln Gly Asp Asn
            980                 985                 990

Ile Ser Gly Val Asn Ser Lys Pro Leu Ser Asp Asp Val Arg Pro Asp
            995                 1000                1005

Lys Asn His Glu Glu Val Lys Glu His Thr Ser Asn Ser Asp Asn Val
        1010                1015                1020

Gln Gln Ser Gly Gly Ile Val Asn Met Asn Val Glu Lys Glu Leu Lys
1025                1030                1035                1040

Asp Thr Leu Glu Asn Pro Ser Ser Leu Asp Glu Gly Lys Ala His
            1045                1050                1055

Glu Glu Leu Ser Glu Pro Asn Leu Ser Ser Asp Gln Asp Met Ser Asn
            1060                1065                1070

Thr Pro Gly Pro Leu Asp Asn Thr Ser Glu Glu Thr Thr Glu Arg Ile
            1075                1080                1085

Ser Asn Asn Glu Tyr Lys Val Asn Glu Arg Glu Gly Glu Arg Thr Leu
            1090                1095                1100

Thr Lys Glu Tyr Glu Asp Ile Val Leu Lys Ser His Met Asn Arg Glu
1105                1110                1115                1120

Ser Asp Asp Gly Glu Leu Tyr Asp Glu Asn Ser Asp Leu Ser Thr Val
            1125                1130                1135

Asn Asp Glu Ser Glu Asp Ala Glu Ala Lys Met Lys Gly Asn Asp Thr
            1140                1145                1150

Ser Glu Met Ser His Asn Ser Ser Gln His Ile Glu Ser Asp Gln Gln
            1155                1160                1165

Lys Asn Asp Met Lys Thr Val Gly Asp Leu Gly Thr Thr His Val Gln
            1170                1175                1180

Asn Glu Ile Ser Val Pro Val Thr Gly Glu Ile Asp Glu Lys Leu Arg
1185                1190                1195                1200

Glu Ser Lys Glu Ser Lys Ile His Lys Ala Glu Glu Glu Arg Leu Ser
            1205                1210                1215

His Thr Asp Ile His Lys Ile Asn Pro Glu Asp Arg Asn Ser Asn Thr
            1220                1225                1230

Leu His Leu Lys Asp Ile Arg Asn Glu Glu Asn Glu Arg His Leu Thr
            1235                1240                1245

Asn Gln Asn Ile Asn Ile Ser Gln Glu Arg Asp Leu Gln Lys His Gly
            1250                1255                1260

Phe His Thr Met Asn Asn Leu His Gly Asp Gly Val Ser Glu Arg Ser
1265                1270                1275                1280

Gln Ile Asn His Ser His His Gly Asn Arg Gln Asp Arg Gly Gly Asn
            1285                1290                1295

Ser Gly Asn Val Leu Asn Met Arg Ser Asn Asn Asn Asn Phe Asn Asn
```

```
                     1300              1305              1310
Ile Pro Ser Arg Tyr Asn Leu Tyr Asp Lys Leu Asp Leu Asp Leu
            1315              1320              1325

Tyr Glu Asn Arg Asn Asp Ser Thr Thr Lys Glu Leu Ile Lys Lys Leu
            1330              1335              1340

Ala Glu Ile Asn Lys Cys Glu Asn Glu Ile Ser Val Lys Tyr Cys Asp
1345              1350              1355              1360

His Met Ile His Glu Glu Ile Pro Leu Lys Thr Cys Thr Lys Glu Lys
                1365              1370              1375

Thr Arg Asn Leu Cys Cys Ala Val Ser Asp Tyr Cys Met Ser Tyr Phe
            1380              1385              1390

Thr Tyr Asp Ser Glu Glu Tyr Tyr Asn Cys Thr Lys Arg Glu Phe Asp
            1395              1400              1405

Asp Pro Ser Tyr Thr Cys Phe Arg Lys Glu Ala Phe Ser Ser Met Pro
            1410              1415              1420

Tyr Tyr Ala Gly Ala Gly Val Leu Phe Ile Ile Leu Val Ile Leu Gly
1425              1430              1435              1440

Ala Ser Gln Ala Lys Tyr Gln Ser Ser Glu Gly Val Met Asn Glu Asn
                1445              1450              1455

Asn Glu Asn Asn Phe Leu Phe Glu Val Thr Asp Asn Leu Asp Lys Leu
            1460              1465              1470

Ser Asn Met Phe Asn Gln Gln Val Gln Glu Thr Asn Ile Asn Asp Phe
            1475              1480              1485

Ser Glu Tyr His Glu Asp Ile Asn Asp Ile Asn Phe Lys Lys
            1490              1495              1500

<210> SEQ ID NO 36
<211> LENGTH: 512
<212> TYPE: PRT
<213> ORGANISM: Artificial Sequence
<220> FEATURE:
<223> OTHER INFORMATION: plasmodium falciparum EBA175 antigenic fragment

<400> SEQUENCE: 36

Ser Gln Glu Ala Val Pro Glu Glu Ser Thr Glu Ile Ala His Arg Thr
1               5                   10                  15

Glu Thr Arg Thr Asp Glu Arg Lys Asn Gln Glu Pro Ala Asn Lys Asp
            20                  25                  30

Leu Lys Asn Pro Gln Gln Ser Val Gly Glu Asn Gly Thr Lys Asp Leu
        35                  40                  45

Leu Gln Glu Asp Leu Gly Gly Ser Arg Ser Glu Asp Glu Val Thr Gln
    50                  55                  60

Glu Phe Gly Val Asn His Gly Ile Pro Lys Gly Glu Asp Gln Thr Leu
65                  70                  75                  80

Gly Lys Ser Asp Ala Ile Pro Asn Ile Gly Glu Pro Glu Thr Gly Ile
                85                  90                  95

Ser Thr Thr Glu Glu Ser Arg His Glu Glu Gly His Asn Lys Gln Ala
            100                 105                 110

Leu Ser Thr Ser Val Asp Glu Pro Glu Leu Ser Asp Thr Leu Gln Leu
        115                 120                 125

His Glu Asp Thr Lys Glu Asn Asp Lys Leu Pro Leu Glu Ser Ser Thr
    130                 135                 140

Ile Thr Ser Pro Thr Glu Ser Gly Ser Ser Asp Thr Glu Glu Thr Pro
145                 150                 155                 160

Ser Ile Ser Glu Gly Pro Lys Gly Asn Glu Gln Lys Lys Arg Asp Asp
```

```
                165                 170                 175
Asp Ser Leu Ser Lys Ile Ser Val Ser Pro Glu Asn Ser Arg Pro Glu
            180                 185                 190

Thr Asp Ala Lys Asp Thr Ser Asn Leu Leu Lys Leu Lys Gly Asp Val
        195                 200                 205

Asp Ile Ser Met Pro Lys Ala Val Ile Gly Ser Ser Pro Asn Asp Asn
    210                 215                 220

Ile Asn Val Thr Glu Gln Gly Asp Asn Ile Ser Gly Val Asn Ser Lys
225                 230                 235                 240

Pro Leu Ser Asp Asp Val Arg Pro Asp Lys Asn His Glu Glu Val Lys
                245                 250                 255

Glu His Thr Ser Asn Ser Asp Asn Val Gln Gln Ser Gly Gly Ile Val
            260                 265                 270

Asn Met Asn Val Glu Lys Glu Leu Lys Asp Thr Leu Glu Asn Pro Ser
        275                 280                 285

Ser Ser Leu Asp Glu Gly Lys Ala His Glu Glu Leu Ser Glu Pro Asn
    290                 295                 300

Leu Ser Ser Asp Gln Asp Met Ser Asn Thr Pro Gly Pro Leu Asp Asn
305                 310                 315                 320

Thr Ser Glu Glu Thr Thr Glu Arg Ile Ser Asn Asn Glu Tyr Lys Val
                325                 330                 335

Asn Glu Arg Glu Gly Glu Arg Thr Leu Thr Lys Glu Tyr Glu Asp Ile
            340                 345                 350

Val Leu Lys Ser His Met Asn Arg Glu Ser Asp Asp Gly Glu Leu Tyr
        355                 360                 365

Asp Glu Asn Ser Asp Leu Ser Thr Val Asn Asp Glu Ser Glu Asp Ala
    370                 375                 380

Glu Ala Lys Met Lys Gly Asn Asp Thr Ser Glu Met Ser His Asn Ser
385                 390                 395                 400

Ser Gln His Ile Glu Ser Asp Gln Gln Lys Asn Asp Met Lys Thr Val
                405                 410                 415

Gly Asp Leu Gly Thr Thr His Val Gln Asn Glu Ile Ser Val Pro Val
            420                 425                 430

Thr Gly Glu Ile Asp Glu Lys Leu Arg Glu Ser Lys Glu Ser Lys Ile
        435                 440                 445

His Lys Ala Glu Glu Arg Leu Ser His Thr Asp Ile His Lys Ile
    450                 455                 460

Asn Pro Glu Asp Arg Asn Ser Asn Thr Leu His Leu Lys Asp Ile Arg
465                 470                 475                 480

Asn Glu Glu Asn Glu Arg His Leu Thr Asn Gln Asn Ile Asn Ile Ser
                485                 490                 495

Gln Glu Arg Asp Leu Gln Lys His Gly Phe His Thr Met Asn Asn Leu
            500                 505                 510

<210> SEQ ID NO 37
<211> LENGTH: 1567
<212> TYPE: PRT
<213> ORGANISM: Plasmodium falciparum

<400> SEQUENCE: 37

Met Lys Gly Lys Met Asn Met Cys Leu Phe Phe Phe Tyr Ser Ile Leu
1               5                   10                  15

Tyr Val Val Leu Cys Thr Tyr Val Leu Gly Ile Ser Glu Glu Tyr Leu
            20                  25                  30
```

```
Lys Glu Arg Pro Gln Gly Leu Asn Val Glu Thr Asn Asn Asn Asn
             35                  40                  45
Asn Asn Asn Asn Asn Asn Ser Asn Ser Asn Asp Ala Met Ser Phe Val
 50                  55                  60
Asn Glu Val Ile Arg Phe Ile Glu Asn Glu Lys Asp Asp Lys Glu Asp
 65                  70                  75                  80
Lys Lys Val Lys Ile Ile Ser Arg Pro Val Glu Asn Thr Leu His Arg
                 85                  90                  95
Tyr Pro Val Ser Ser Phe Leu Asn Ile Lys Lys Tyr Gly Arg Lys Gly
                100                 105                 110
Glu Tyr Leu Asn Arg Asn Ser Phe Val Gln Arg Ser Tyr Ile Arg Gly
            115                 120                 125
Cys Lys Gly Lys Arg Ser Thr His Thr Trp Ile Cys Glu Asn Lys Gly
    130                 135                 140
Asn Asn Asn Ile Cys Ile Pro Asp Arg Arg Val Gln Leu Cys Ile Thr
145                 150                 155                 160
Ala Leu Gln Asp Leu Lys Asn Ser Gly Ser Glu Thr Thr Asp Arg Lys
                165                 170                 175
Leu Leu Arg Asp Lys Val Phe Asp Ser Ala Met Tyr Glu Thr Asp Leu
            180                 185                 190
Leu Trp Asn Lys Tyr Gly Phe Arg Gly Phe Asp Asp Phe Cys Asp Asp
        195                 200                 205
Val Lys Asn Ser Tyr Leu Asp Tyr Lys Asp Val Ile Phe Gly Thr Asp
    210                 215                 220
Leu Asp Lys Asn Asn Ile Ser Lys Leu Val Glu Glu Ser Leu Lys Arg
225                 230                 235                 240
Phe Phe Lys Lys Asp Ser Ser Val Leu Asn Pro Thr Ala Trp Trp Arg
                245                 250                 255
Arg Tyr Gly Thr Arg Leu Trp Lys Thr Met Ile Gln Pro Tyr Ala His
            260                 265                 270
Leu Gly Cys Arg Lys Pro Asp Glu Asn Glu Pro Gln Ile Asn Arg Trp
        275                 280                 285
Ile Leu Glu Trp Gly Lys Tyr Asn Cys Arg Leu Met Lys Glu Lys Glu
    290                 295                 300
Lys Leu Leu Thr Gly Glu Cys Ser Val Asn Arg Lys Lys Ser Asp Cys
305                 310                 315                 320
Ser Thr Gly Cys Asn Asn Glu Cys Tyr Thr Tyr Arg Ser Leu Ile Asn
                325                 330                 335
Arg Gln Arg Tyr Glu Val Ser Ile Leu Gly Lys Lys Tyr Ile Lys Val
            340                 345                 350
Val Arg Tyr Thr Ile Phe Arg Arg Lys Ile Val Gln Pro Asp Asn Ala
        355                 360                 365
Leu Asp Phe Leu Lys Leu Asn Cys Ser Glu Cys Lys Asp Ile Asp Phe
    370                 375                 380
Lys Pro Phe Phe Glu Phe Glu Tyr Gly Lys Tyr Glu Glu Lys Cys Met
385                 390                 395                 400
Cys Gln Ser Tyr Ile Asp Leu Lys Ile Gln Phe Lys Asn Asn Asp Ile
                405                 410                 415
Cys Ser Phe Asn Ala Gln Thr Asp Thr Val Ser Ser Asp Lys Arg Phe
            420                 425                 430
Cys Leu Glu Lys Lys Glu Phe Lys Pro Trp Lys Cys Asp Lys Asn Ser
        435                 440                 445
Phe Glu Thr Val His His Lys Gly Val Cys Val Ser Pro Arg Arg Gln
```

-continued

```
            450                 455                 460
Gly Phe Cys Leu Gly Asn Leu Asn Tyr Leu Leu Asn Asp Asp Ile Tyr
465                 470                 475                 480

Asn Val His Asn Ser Gln Leu Leu Ile Glu Ile Met Ala Ser Lys
                485                 490                 495

Gln Glu Gly Lys Leu Leu Trp Lys Lys His Gly Thr Ile Leu Asp Asn
                500                 505                 510

Gln Asn Ala Cys Lys Tyr Ile Asn Asp Ser Tyr Val Asp Tyr Lys Asp
            515                 520                 525

Ile Val Ile Gly Asn Asp Leu Trp Asn Asp Asn Ser Ile Lys Val
        530                 535                 540

Gln Asn Asn Leu Asn Leu Ile Phe Glu Arg Asn Phe Gly Tyr Lys Val
545                 550                 555                 560

Gly Arg Asn Lys Leu Phe Lys Thr Ile Lys Glu Leu Lys Asn Val Trp
                565                 570                 575

Trp Ile Leu Asn Arg Asn Lys Val Trp Glu Ser Met Arg Cys Gly Ile
            580                 585                 590

Asp Glu Val Asp Gln Arg Arg Lys Thr Cys Glu Arg Ile Asp Glu Leu
        595                 600                 605

Glu Asn Met Pro Gln Phe Phe Arg Trp Phe Ser Gln Trp Ala His Phe
    610                 615                 620

Phe Cys Lys Glu Lys Glu Tyr Trp Glu Leu Lys Leu Asn Asp Lys Cys
625                 630                 635                 640

Thr Gly Asn Asn Gly Lys Ser Leu Cys Gln Asp Lys Thr Cys Gln Asn
                645                 650                 655

Val Cys Thr Asn Met Asn Tyr Trp Thr Tyr Thr Arg Lys Leu Ala Tyr
            660                 665                 670

Glu Ile Gln Ser Val Lys Tyr Asp Lys Asp Arg Lys Leu Phe Ser Leu
        675                 680                 685

Ala Lys Asp Lys Asn Val Thr Thr Phe Leu Lys Glu Asn Ala Lys Asn
    690                 695                 700

Cys Ser Asn Ile Asp Phe Thr Lys Ile Phe Asp Gln Leu Asp Lys Leu
705                 710                 715                 720

Phe Lys Glu Arg Cys Ser Cys Met Asp Thr Gln Val Leu Glu Val Lys
                725                 730                 735

Asn Lys Glu Met Leu Ser Ile Asp Ser Asn Ser Glu Asp Ala Thr Asp
            740                 745                 750

Ile Ser Glu Lys Asn Gly Glu Glu Leu Tyr Val Asn His Asn Ser
        755                 760                 765

Val Ser Val Ala Ser Gly Asn Lys Glu Ile Glu Lys Ser Lys Asp Glu
    770                 775                 780

Lys Gln Pro Glu Lys Glu Ala Lys Gln Thr Asn Gly Thr Leu Thr Val
785                 790                 795                 800

Arg Thr Asp Lys Asp Ser Asp Arg Asn Lys Gly Lys Asp Thr Ala Thr
                805                 810                 815

Asp Thr Lys Asn Ser Pro Glu Asn Leu Lys Val Gln Glu His Gly Thr
            820                 825                 830

Asn Gly Glu Thr Ile Lys Glu Glu Pro Pro Lys Leu Pro Glu Ser Ser
        835                 840                 845

Glu Thr Leu Gln Ser Gln Glu Gln Leu Glu Ala Glu Ala Gln Lys Gln
    850                 855                 860

Lys Gln Glu Glu Glu Pro Lys Lys Gln Glu Glu Pro Lys Lys
865                 870                 875                 880
```

-continued

```
Lys Gln Glu Glu Glu Gln Lys Arg Glu Gln Glu Gln Lys Gln Glu Gln
                885                 890                 895
Glu Glu Glu Glu Gln Lys Gln Glu Glu Gln Gln Ile Gln Asp Gln
            900                 905                 910
Ser Gln Ser Gly Leu Asp Gln Ser Ser Lys Val Gly Val Ala Ser Glu
                915                 920                 925
Gln Asn Glu Ile Ser Ser Gly Gln Gln Asn Val Lys Ser Ser Ser
    930                 935                 940
Pro Glu Val Val Pro Gln Glu Thr Thr Ser Glu Asn Gly Ser Ser Gln
945                 950                 955                 960
Asp Thr Lys Ile Ser Ser Thr Glu Pro Asn Glu Asn Ser Val Val Asp
                965                 970                 975
Arg Ala Thr Asp Ser Met Asn Leu Asp Pro Glu Lys Val His Asn Glu
            980                 985                 990
Asn Met Ser Asp Pro Asn Thr Asn Thr Glu Pro Asp Ala Ser Leu Lys
        995                 1000                1005
Asp Asp Lys Lys Glu Val Asp Ala Lys Lys Glu Leu Gln Ser Thr
    1010                1015                1020
Val Ser Arg Ile Glu Ser Asn Glu Gln Asp Val Gln Ser Thr Pro Pro
1025                1030                1035                1040
Glu Asp Thr Pro Thr Val Glu Gly Lys Val Gly Asp Lys Ala Glu Met
                1045                1050                1055
Leu Thr Ser Pro His Ala Thr Asp Asn Ser Glu Ser Glu Ser Gly Leu
            1060                1065                1070
Asn Pro Thr Asp Asp Ile Lys Thr Thr Asp Gly Val Val Lys Glu Gln
        1075                1080                1085
Glu Ile Leu Gly Gly Gly Glu Ser Ala Thr Glu Thr Ser Lys Ser Asn
    1090                1095                1100
Leu Glu Lys Pro Lys Asp Val Glu Pro Ser His Glu Ile Ser Glu Pro
1105                1110                1115                1120
Val Leu Ser Gly Thr Thr Gly Lys Glu Glu Ser Glu Leu Leu Lys Ser
                1125                1130                1135
Lys Ser Ile Glu Thr Lys Gly Glu Thr Asp Pro Arg Ser Asn Asp Gln
            1140                1145                1150
Glu Asp Ala Thr Asp Asp Val Val Glu Asn Ser Arg Asp Asp Asn
        1155                1160                1165
Ser Leu Ser Asn Ser Val Asp Asn Gln Ser Asn Val Leu Asn Arg Glu
    1170                1175                1180
Asp Pro Ile Ala Ser Glu Thr Glu Val Val Ser Glu Pro Glu Asp Ser
1185                1190                1195                1200
Ser Arg Ile Ile Thr Thr Glu Val Pro Ser Thr Thr Val Lys Pro Pro
                1205                1210                1215
Asp Glu Lys Arg Ser Glu Glu Val Gly Glu Lys Glu Ala Lys Glu Ile
            1220                1225                1230
Lys Val Glu Pro Val Val Pro Arg Ala Ile Gly Glu Pro Met Glu Asn
        1235                1240                1245
Ser Val Ser Val Gln Ser Pro Pro Asn Val Glu Asp Val Glu Lys Glu
    1250                1255                1260
Thr Leu Ile Ser Glu Asn Asn Gly Leu His Asn Asp Thr His Arg Gly
1265                1270                1275                1280
Asn Ile Ser Glu Lys Asp Leu Ile Asp Ile His Leu Leu Arg Asn Glu
                1285                1290                1295
```

```
Ala Gly Ser Thr Ile Leu Asp Asp Ser Arg Arg Asn Gly Glu Met Thr
            1300                1305                1310

Glu Gly Ser Glu Ser Asp Val Gly Glu Leu Gln Glu His Asn Phe Ser
        1315                1320                1325

Thr Gln Gln Lys Asp Glu Lys Asp Phe Asp Gln Ile Ala Ser Asp Arg
    1330                1335                1340

Glu Lys Glu Glu Ile Gln Lys Leu Leu Asn Ile Gly His Glu Glu Asp
1345                1350                1355                1360

Glu Asp Val Leu Lys Met Asp Arg Thr Glu Asp Ser Met Ser Asp Gly
            1365                1370                1375

Val Asn Ser His Leu Tyr Tyr Asn Asn Leu Ser Ser Glu Glu Lys Met
        1380                1385                1390

Glu Gln Tyr Asn Asn Arg Asp Ala Ser Lys Asp Arg Glu Glu Ile Leu
    1395                1400                1405

Asn Arg Ser Asn Thr Asn Thr Cys Ser Asn Glu His Ser Leu Lys Tyr
        1410                1415                1420

Cys Gln Tyr Met Glu Arg Asn Lys Asp Leu Leu Glu Thr Cys Ser Glu
1425                1430                1435                1440

Asp Lys Arg Leu His Leu Cys Cys Glu Ile Ser Asp Tyr Cys Leu Lys
            1445                1450                1455

Phe Phe Asn Pro Lys Ser Ile Glu Tyr Phe Asp Cys Thr Gln Lys Glu
        1460                1465                1470

Phe Asp Asp Pro Thr Tyr Asn Cys Phe Arg Lys Gln Arg Phe Thr Ser
    1475                1480                1485

Met His Tyr Ile Ala Gly Gly Gly Ile Ile Ala Leu Leu Leu Phe Ile
        1490                1495                1500

Leu Gly Ser Ala Ser Tyr Arg Lys Asn Leu Asp Asp Glu Lys Gly Phe
1505                1510                1515                1520

Tyr Asp Ser Asn Leu Asn Asp Ser Ala Phe Glu Tyr Asn Asn Asn Lys
            1525                1530                1535

Tyr Asn Lys Leu Pro Tyr Met Phe Asp Gln Gln Ile Asn Val Val Asn
        1540                1545                1550

Ser Asp Leu Tyr Ser Glu Gly Ile Tyr Asp Asp Thr Thr Thr Phe
    1555                1560                1565

<210> SEQ ID NO 38
<211> LENGTH: 1210
<212> TYPE: PRT
<213> ORGANISM: Plasmodium falciparum

<400> SEQUENCE: 38

Met Lys Gly Tyr Phe Asn Ile Tyr Phe Leu Ile Pro Leu Ile Phe Leu
1               5                   10                  15

Tyr Asn Val Ile Arg Ile Asn Glu Ser Ile Ile Gly Arg Thr Leu Tyr
            20                  25                  30

Asn Arg Gln Asp Glu Ser Ser Asp Ile Ser Arg Val Asn Ser Pro Glu
        35                  40                  45

Leu Asn Asn Asn His Lys Thr Asn Ile Tyr Asp Ser Asp Tyr Glu Asp
    50                  55                  60

Val Asn Asn Lys Leu Ile Asn Ser Phe Val Glu Asn Lys Ser Val Lys
65                  70                  75                  80

Lys Lys Arg Ser Leu Ser Phe Ile Asn Asn Lys Thr Lys Ser Tyr Asp
            85                  90                  95

Ile Ile Pro Pro Ser Tyr Ser Tyr Arg Asn Asp Lys Phe Asn Ser Leu
        100                 105                 110
```

```
Ser Glu Asn Glu Asp Asn Ser Gly Asn Thr Asn Ser Asn Asn Phe Ala
            115                 120                 125
Asn Thr Ser Glu Ile Ser Ile Gly Lys Asp Asn Lys Gln Tyr Thr Phe
        130                 135                 140
Ile Gln Lys Arg Thr His Leu Phe Ala Cys Gly Ile Lys Arg Lys Ser
145                 150                 155                 160
Ile Lys Trp Ile Cys Arg Glu Asn Ser Glu Lys Ile Thr Val Cys Val
                165                 170                 175
Pro Asp Arg Lys Ile Gln Leu Cys Ile Ala Asn Phe Leu Asn Ser Arg
            180                 185                 190
Leu Glu Thr Met Glu Lys Phe Lys Glu Ile Phe Leu Ile Ser Val Asn
        195                 200                 205
Thr Glu Ala Lys Leu Leu Tyr Asn Lys Asn Glu Gly Lys Asp Pro Ser
    210                 215                 220
Ile Phe Cys Asn Glu Leu Arg Asn Ser Phe Ser Asp Phe Arg Asn Ser
225                 230                 235                 240
Phe Ile Gly Asp Asp Met Asp Phe Gly Gly Asn Thr Asp Arg Val Lys
                245                 250                 255
Gly Tyr Ile Asn Lys Lys Phe Ser Asp Tyr Tyr Lys Glu Lys Asn Val
            260                 265                 270
Glu Lys Leu Asn Asn Ile Lys Lys Glu Trp Trp Glu Lys Asn Lys Ala
        275                 280                 285
Asn Leu Trp Asn His Met Ile Val Asn His Lys Gly Asn Ile Ser Lys
    290                 295                 300
Glu Cys Ala Ile Ile Pro Ala Glu Glu Pro Gln Ile Asn Leu Trp Ile
305                 310                 315                 320
Lys Glu Trp Asn Glu Asn Phe Leu Met Glu Lys Lys Arg Leu Phe Leu
                325                 330                 335
Asn Ile Lys Asp Lys Cys Val Glu Asn Lys Lys Tyr Glu Ala Cys Phe
            340                 345                 350
Gly Gly Cys Arg Leu Pro Cys Ser Ser Tyr Thr Ser Phe Met Lys Lys
        355                 360                 365
Ser Lys Thr Gln Met Glu Val Leu Thr Asn Leu Tyr Lys Lys Lys Asn
    370                 375                 380
Ser Gly Val Asp Lys Asn Asn Phe Leu Asn Asp Leu Phe Lys Lys Asn
385                 390                 395                 400
Asn Lys Asn Asp Leu Asp Asp Phe Phe Lys Asn Glu Lys Glu Tyr Asp
                405                 410                 415
Asp Leu Cys Asp Cys Arg Tyr Thr Ala Thr Ile Ile Lys Ser Phe Leu
            420                 425                 430
Asn Gly Pro Ala Lys Asn Asp Val Asp Ile Ala Ser Gln Ile Asn Val
        435                 440                 445
Asn Asp Leu Arg Gly Phe Gly Cys Asn Tyr Lys Ser Asn Asn Glu Lys
    450                 455                 460
Ser Trp Asn Cys Thr Gly Thr Phe Thr Asn Lys Phe Pro Gly Thr Cys
465                 470                 475                 480
Glu Pro Pro Arg Arg Gln Thr Leu Cys Leu Gly Arg Thr Tyr Leu Leu
                485                 490                 495
His Arg Gly His Glu Glu Asp Tyr Lys Glu His Leu Leu Gly Ala Ser
            500                 505                 510
Ile Tyr Glu Ala Gln Leu Leu Lys Tyr Lys Tyr Lys Glu Lys Asp Glu
        515                 520                 525
```

-continued

```
Asn Ala Leu Cys Ser Ile Ile Gln Asn Ser Tyr Ala Asp Leu Ala Asp
        530                 535                 540
Ile Ile Lys Gly Ser Asp Ile Ile Lys Asp Tyr Tyr Gly Lys Lys Met
545                 550                 555                 560
Glu Glu Asn Leu Asn Lys Val Asn Lys Asp Lys Lys Arg Asn Glu Glu
                565                 570                 575
Ser Leu Lys Ile Phe Arg Glu Lys Trp Trp Asp Glu Asn Lys Glu Asn
        580                 585                 590
Val Trp Lys Val Met Ser Ala Val Leu Lys Asn Lys Glu Thr Cys Lys
        595                 600                 605
Asp Tyr Asp Lys Phe Gln Lys Ile Pro Gln Phe Leu Arg Trp Phe Lys
610                 615                 620
Glu Trp Gly Asp Asp Phe Cys Glu Lys Arg Lys Glu Lys Ile Tyr Ser
625                 630                 635                 640
Phe Glu Ser Phe Lys Val Glu Cys Lys Lys Asp Cys Asp Glu Asn
                645                 650                 655
Thr Cys Lys Asn Lys Cys Ser Glu Tyr Lys Lys Trp Ile Asp Leu Lys
            660                 665                 670
Lys Ser Glu Tyr Glu Lys Gln Val Asp Lys Tyr Thr Lys Asp Lys Asn
        675                 680                 685
Lys Lys Met Tyr Asp Asn Ile Asp Glu Val Lys Asn Lys Glu Ala Asn
690                 695                 700
Val Tyr Leu Lys Glu Lys Ser Lys Cys Lys Asp Val Asn Phe Asp
705                 710                 715                 720
Asp Lys Ile Phe Asn Glu Ser Pro Asn Glu Tyr Glu Asp Met Cys Lys
            725                 730                 735
Lys Cys Asp Glu Ile Lys Tyr Leu Asn Glu Ile Lys Tyr Pro Lys Thr
        740                 745                 750
Lys His Asp Ile Tyr Asp Ile Asp Thr Phe Ser Asp Thr Phe Gly Asp
        755                 760                 765
Gly Thr Pro Ile Ser Ile Asn Ala Asn Ile Asn Glu Gln Gln Ser Gly
    770                 775                 780
Lys Asp Thr Ser Asn Thr Gly Asn Ser Glu Thr Ser Asp Ser Pro Val
785                 790                 795                 800
Ser His Glu Pro Glu Ser Asp Ala Ala Ile Asn Val Glu Lys Leu Ser
                805                 810                 815
Gly Asp Glu Ser Ser Glu Thr Arg Gly Ile Leu Asp Ile Asn Asp
            820                 825                 830
Pro Ser Val Thr Asn Asn Val Asn Glu Val His Asp Ala Ser Asn Thr
        835                 840                 845
Gln Gly Ser Val Ser Asn Thr Ser Asp Ile Thr Asn Gly His Ser Glu
    850                 855                 860
Ser Ser Leu Asn Arg Thr Thr Asn Ala Gln Asp Ile Lys Ile Gly Arg
865                 870                 875                 880
Ser Gly Asn Glu Gln Ser Asp Asn Gln Glu Asn Ser Ser His Ser Ser
                885                 890                 895
Asp Asn Ser Gly Ser Leu Thr Ile Gly Gln Val Pro Ser Glu Asp Asn
            900                 905                 910
Thr Gln Asn Thr Tyr Asp Ser Gln Asn Pro His Arg Asp Thr Pro Asn
        915                 920                 925
Ala Leu Ala Ser Leu Pro Ser Asp Asp Lys Ile Asn Glu Ile Glu Gly
    930                 935                 940
Phe Asp Ser Ser Arg Asp Ser Glu Asn Gly Arg Gly Asp Thr Thr Ser
```

```
                945              950              955              960
Asn Thr His Asp Val Arg Arg Thr Asn Ile Val Ser Glu Arg Val
                    965              970              975
Asn Ser His Asp Phe Ile Arg Asn Gly Met Ala Asn Asn Ala His
                980              985              990
His Gln Tyr Ile Thr Gln Ile Glu Asn Asn Gly Ile Arg Gly Gln
                995             1000             1005
Glu Glu Ser Ala Gly Asn Ser Val Asn Tyr Lys Asp Asn Pro Lys Arg
           1010             1015             1020
Ser Asn Phe Ser Ser Glu Asn Asp His Lys Lys Asn Ile Gln Glu Tyr
1025             1030             1035             1040
Asn Ser Arg Asp Thr Lys Arg Val Arg Glu Glu Ile Ile Lys Leu Ser
                1045             1050             1055
Lys Gln Asn Lys Cys Asn Asn Glu Tyr Ser Met Glu Tyr Cys Thr Tyr
                1060             1065             1070
Ser Asp Glu Arg Asn Ser Ser Pro Gly Pro Cys Ser Arg Glu Glu Arg
            1075             1080             1085
Lys Lys Leu Cys Cys Gln Ile Ser Asp Tyr Cys Leu Lys Tyr Phe Asn
            1090             1095             1100
Phe Tyr Ser Ile Glu Tyr Tyr Asn Cys Ile Lys Ser Glu Ile Lys Ser
1105             1110             1115             1120
Pro Glu Tyr Lys Cys Phe Lys Ser Glu Gly Gln Ser Ser Ile Pro Tyr
                1125             1130             1135
Phe Ala Ala Gly Gly Ile Leu Val Val Ile Val Leu Leu Leu Ser Ser
            1140             1145             1150
Ala Ser Arg Met Gly Lys Ser Asn Glu Glu Tyr Asp Ile Gly Glu Ser
            1155             1160             1165
Asn Ile Glu Ala Thr Phe Glu Glu Asn Asn Tyr Leu Asn Lys Leu Ser
            1170             1175             1180
Arg Ile Phe Asn Gln Glu Val Gln Glu Thr Asn Ile Ser Asp Tyr Ser
1185             1190             1195             1200
Glu Tyr Asn Tyr Asn Glu Lys Asn Met Tyr
                1205             1210

<210> SEQ ID NO 39
<211> LENGTH: 1482
<212> TYPE: DNA
<213> ORGANISM: Artificial Sequence
<220> FEATURE:
<223> OTHER INFORMATION: plasmodium falciparum Codon optimised sequence

<400> SEQUENCE: 39
ggtacccata tgaaaagcta ttgcaatgat ctgagcgaat gcgatattgg cctgatttat      60
catttcgata cctattgcat caatgatcag tacctgtttg tgagctatag ctgtagcaat     120
ctgtgcaata aatgccataa taatagcacc tgttatggca atcgctttaa ttatgattgc     180
ttttgcgata atccgtatat tagcaaatat ggcaataaac tgtgcgaacg tccgaatgat     240
tgtgaaagcg ttctgtgtag ccagaatcag gtttgtcaga ttctgccgaa tgataaactg     300
atttgtcagt gcgaagaagg ctataaaaac gttaaggta aatgcgtgcc ggataataaa      360
tgtgatctga gctgtccgag caataaagtt tgcgttattg aaaatggcaa acagacctgt     420
aaatgcagcg aacgttttgt tctggaaaat ggtgtttgca tttgcgccaa tgattataaa     480
atggaagatg catcaattg cattgccaaa aataaatgca aacgcaaaga gtatgaaaat     540
atttgcacca atccgaatga atgtgcgcc tataatgaag aaaccgatat tgtgaaatgc     600
```

-continued

```
gaatgcaaag aacattatta tcgtagcagc cgtggtgaat gcattctgaa tgattattgc      660
aaagacatca attgcaaaga aaatgaagaa tgcagcattg tgaattttaa accggaatgc      720
gtgtgcaaag aaaatctgaa aaaaaataac aaaggcgagt gcatttatga aaattcatgc      780
ctgattaatg aaggcaattg cccgaaagat agcaaatgca tttatcgcga atataaaccg      840
catgaatgcg tttgcaataa acagggtcat gttgccgtta atggtaaatg tgtgctggaa      900
gataaatgcg tgcataataa aaaatgtagc gaaaattcca tttgcgtgaa tgtgatgaat      960
aaagaaccga tttgcgtgtg cacctataat tattataaaa agatggcgt gtgcctgatt      1020 cagaatccgt gtctgaaaga taatggtggt tgtagccgta atagcgaatg cacctttaaa     1080
tattccaaaa ttaattgtac ctgtaaagag aactacaaaa acaaagatga tagctgcgtg     1140
ccgaatacca atgaatatga tgaaagcttt acctttcagt ataatgatga tgccagcatt     1200
attctgggtg catgtggtat gattgaattt agctatatct acaaccagat tatctggaaa     1260
attaataata gcaaagagag ctacgttttc tattatgatt atccgaccgc aggcaatatt     1320
gaagtgcaga ttaaaaacga aattttccac accattatct acctgaaaaa aaaaattggc     1380
aatagcgtga tttatgatga ttttcaggtg gatcatcaga cctgtattta tgaaaatgtg     1440
ttctattaca gcaatcagaa ttaaggatcc ctcgaggagc tc                        1482
```

<210> SEQ ID NO 40
<211> LENGTH: 39
<212> TYPE: DNA
<213> ORGANISM: Artificial Sequence
<220> FEATURE:
<223> OTHER INFORMATION: Oligonucleotide primer

<400> SEQUENCE: 40

```
cgctagccat atgaatgaag aaacagatat tgtaaaatg                             39
```

<210> SEQ ID NO 41
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 41

```
cgaggatccc taatcttcta aaacacattt tcc                                   33
```

<210> SEQ ID NO 42
<211> LENGTH: 336
<212> TYPE: DNA
<213> ORGANISM: Artificial Sequence
<220> FEATURE:
<223> OTHER INFORMATION: plasmodium falciparum coding sequence of
      rRh2-15 fragment

<400> SEQUENCE: 42

```
aaaaaatatg aaacatatgt agatatgaaa acaattgaat ctaaatatac aacagtaatg      60
actctatcag aacatttatt agaatatgca atggatgttt aaaagctaa ccctcaaaaa      120 cctattgatc caaaagcaaa tctgattca gaagtagtaa aattacaaat aaaaatat      180 gagaaatcaa atgaattaga taatgctata agtcaagtaa aaacactaat aataataatg      240
aaatcatttt atgatattat tatatctgaa aaagcctcta tggatgaaat ggaaaaaag      300 gaattatcct taaataatta tattgaaaaa acagat                               336
```

<210> SEQ ID NO 43
<211> LENGTH: 1627
<212> TYPE: PRT
<213> ORGANISM: Plasmodium falciparum

<400> SEQUENCE: 43

```
Met Lys Ile Ile Phe Phe Leu Cys Ser Phe Leu Phe Ile Ile Asn
 1               5                  10                  15

Thr Gln Cys Val Thr His Glu Ser Tyr Gln Glu Leu Val Lys Lys Leu
                20                  25                  30

Glu Ala Leu Glu Asp Ala Val Leu Thr Gly Tyr Ser Leu Phe Gln Lys
             35                  40                  45

Glu Lys Met Val Leu Asn Glu Gly Thr Ser Gly Thr Ala Val Thr Thr
 50                  55                  60

Ser Thr Pro Gly Ser Lys Gly Ser Val Ala Ser Gly Gly Ser Gly Gly
 65                  70                  75                  80

Ser Val Ala Ser Gly Gly Ser Val Ala Ser Gly Gly Ser Gly Asn Ser
                 85                  90                  95

Arg Arg Thr Asn Pro Ser Asp Asn Ser Ser Asp Ser Asp Ala Lys Ser
            100                 105                 110

Tyr Ala Asp Leu Lys His Arg Val Arg Asn Tyr Leu Leu Thr Ile Lys
            115                 120                 125

Glu Leu Lys Tyr Pro Gln Leu Phe Asp Leu Thr Asn His Met Leu Thr
130                 135                 140

Leu Cys Asp Asn Ile His Gly Phe Lys Tyr Leu Ile Asp Gly Tyr Glu
145                 150                 155                 160

Glu Ile Asn Glu Leu Leu Tyr Lys Leu Asn Phe Tyr Phe Asp Leu Leu
                165                 170                 175

Arg Ala Lys Leu Asn Asp Val Cys Ala Asn Asp Tyr Cys Gln Ile Pro
            180                 185                 190

Phe Asn Leu Lys Ile Arg Ala Asn Glu Leu Asp Val Leu Lys Lys Leu
        195                 200                 205

Val Phe Gly Tyr Arg Lys Pro Leu Asp Asn Ile Lys Asp Asn Val Gly
    210                 215                 220

Lys Met Glu Asp Tyr Ile Lys Lys Asn Lys Lys Thr Ile Glu Asn Ile
225                 230                 235                 240

Asn Glu Leu Ile Glu Gly Ser Lys Lys Thr Ile Asp Lys Asn Lys Asn
                245                 250                 255

Ala Thr Lys Glu Glu Lys Lys Lys Leu Tyr Gln Ala Gln Tyr Asp
            260                 265                 270

Leu Ser Ile Tyr Asn Lys Gln Leu Glu Glu Ala His Asn Leu Ile Ser
        275                 280                 285

Val Leu Glu Lys Arg Ile Asp Thr Leu Lys Lys Asn Glu Asn Ile Lys
    290                 295                 300

Lys Leu Leu Asp Lys Ile Asn Glu Ile Lys Asn Pro Pro Ala Asn
305                 310                 315                 320

Ser Gly Asn Thr Pro Asn Thr Leu Leu Asp Lys Asn Lys Lys Ile Glu
                325                 330                 335

Glu His Glu Lys Glu Ile Lys Glu Ile Ala Lys Thr Ile Lys Phe Asn
            340                 345                 350

Ile Asp Ser Leu Phe Thr Asp Pro Leu Glu Leu Glu Tyr Tyr Leu Arg
        355                 360                 365

Glu Lys Asn Lys Asn Ile Asp Ile Ser Ala Lys Val Glu Thr Lys Glu
    370                 375                 380
```

```
Ser Thr Glu Pro Asn Glu Tyr Pro Asn Gly Val Thr Tyr Pro Leu Ser
385                 390                 395                 400

Tyr Asn Asp Ile Asn Asn Ala Leu Asn Glu Leu Asn Ser Phe Gly Asp
            405                 410                 415

Leu Ile Asn Pro Phe Asp Tyr Thr Lys Glu Pro Ser Lys Asn Ile Tyr
        420                 425                 430

Thr Asp Asn Glu Arg Lys Lys Phe Ile Asn Glu Ile Lys Glu Lys Ile
    435                 440                 445

Lys Ile Glu Lys Lys Ile Glu Ser Asp Lys Lys Ser Tyr Glu Asp
450                 455                 460

Arg Ser Lys Ser Leu Asn Asp Ile Thr Lys Glu Tyr Glu Lys Leu Leu
465                 470                 475                 480

Asn Glu Ile Tyr Asp Ser Lys Phe Asn Asn Ile Asp Leu Thr Asn
            485                 490                 495

Phe Glu Lys Met Met Gly Lys Arg Tyr Ser Tyr Lys Val Glu Lys Leu
                500                 505                 510

Thr His His Asn Thr Phe Ala Ser Tyr Glu Asn Ser Lys His Asn Leu
        515                 520                 525

Glu Lys Leu Thr Lys Ala Leu Lys Tyr Met Glu Asp Tyr Ser Leu Arg
530                 535                 540

Asn Ile Val Val Glu Lys Glu Leu Lys Tyr Tyr Lys Asn Leu Ile Ser
545                 550                 555                 560

Lys Ile Lys Asn Glu Ile Glu Thr Leu Val Glu Asn Ile Lys Lys Asp
                565                 570                 575

Glu Glu Gln Leu Phe Glu Lys Lys Ile Thr Lys Asp Glu Asn Lys Pro
            580                 585                 590

Asp Glu Lys Ile Leu Glu Val Ser Asp Ile Val Lys Val Gln Val Gln
            595                 600                 605

Lys Val Leu Leu Met Asn Lys Ile Asp Glu Leu Lys Lys Thr Gln Leu
        610                 615                 620

Ile Leu Lys Asn Val Glu Leu Lys His Asn Ile His Val Pro Asn Ser
625                 630                 635                 640

Tyr Lys Gln Glu Asn Lys Gln Glu Pro Tyr Tyr Leu Ile Val Leu Lys
            645                 650                 655

Lys Glu Ile Asp Lys Leu Lys Val Phe Met Pro Lys Val Glu Ser Leu
            660                 665                 670

Ile Asn Glu Glu Lys Lys Asn Ile Lys Thr Glu Gly Gln Ser Asp Asn
            675                 680                 685

Ser Glu Pro Ser Thr Glu Gly Glu Ile Thr Gly Gln Ala Thr Lys
    690                 695                 700

Pro Gly Gln Gln Ala Gly Ser Ala Leu Glu Gly Asp Ser Val Gln Ala
705                 710                 715                 720

Gln Ala Gln Glu Gln Lys Gln Ala Gln Pro Val Pro Val Pro Val
            725                 730                 735

Pro Glu Ala Lys Ala Gln Val Pro Thr Pro Ala Pro Val Asn Asn
        740                 745                 750

Lys Thr Glu Asn Val Ser Lys Leu Asp Tyr Leu Glu Lys Leu Tyr Glu
            755                 760                 765

Phe Leu Asn Thr Ser Tyr Ile Cys His Lys Tyr Ile Leu Val Ser His
        770                 775                 780

Ser Thr Met Asn Glu Lys Ile Leu Lys Gln Tyr Lys Ile Thr Lys Glu
785                 790                 795                 800

Glu Glu Ser Lys Leu Ser Ser Cys Asp Pro Leu Asp Leu Leu Phe Asn
```

-continued

```
                805                 810                 815
Ile Gln Asn Asn Ile Pro Val Met Tyr Ser Met Phe Asp Ser Leu Asn
                820                 825                 830

Asn Ser Leu Ser Gln Leu Phe Met Glu Ile Tyr Glu Lys Glu Met Val
                835                 840                 845

Cys Asn Leu Tyr Lys Leu Lys Asp Asn Asp Lys Ile Lys Asn Leu Leu
                850                 855                 860

Glu Glu Ala Lys Lys Val Ser Thr Ser Val Lys Thr Leu Ser Ser Ser
865                 870                 875                 880

Ser Met Gln Pro Leu Ser Leu Thr Pro Gln Asp Lys Pro Glu Val Ser
                885                 890                 895

Ala Asn Asp Asp Thr Ser His Ser Thr Asn Leu Asn Asn Ser Leu Lys
                900                 905                 910

Leu Phe Glu Asn Ile Leu Ser Leu Gly Lys Asn Lys Asn Ile Tyr Gln
                915                 920                 925

Glu Leu Ile Gly Gln Lys Ser Ser Glu Asn Phe Tyr Glu Lys Ile Leu
                930                 935                 940

Lys Asp Ser Asp Thr Phe Tyr Asn Glu Ser Phe Thr Asn Phe Val Lys
945                 950                 955                 960

Ser Lys Ala Asp Asp Ile Asn Ser Leu Asn Asp Glu Ser Lys Arg Lys
                965                 970                 975

Lys Leu Glu Glu Asp Ile Asn Lys Leu Lys Thr Leu Gln Leu Ser
                980                 985                 990

Phe Asp Leu Tyr Asn Lys Tyr Lys Leu Lys Leu Glu Arg Leu Phe Asp
                995                 1000                1005

Lys Lys Lys Thr Val Gly Lys Tyr Lys Met Gln Ile Lys Lys Leu Thr
                1010                1015                1020

Leu Leu Lys Glu Gln Leu Glu Ser Lys Leu Asn Ser Leu Asn Asn Pro
1025                1030                1035                1040

Lys His Val Leu Gln Asn Phe Ser Val Phe Phe Tyr Lys Lys Lys Glu
                1045                1050                1055

Ala Glu Ile Ala Glu Thr Glu Asn Thr Leu Glu Asn Thr Lys Ile Leu
                1060                1065                1070

Leu Lys His Tyr Lys Gly Leu Val Lys Tyr Tyr Asn Gly Glu Ser Ser
                1075                1080                1085

Pro Leu Lys Thr Leu Ser Glu Glu Ser Ile Gln Thr Glu Asp Asn Tyr
                1090                1095                1100

Ala Ser Leu Glu Asn Phe Lys Val Leu Ser Lys Leu Glu Gly Lys Leu
1105                1110                1115                1120

Lys Asp Asn Leu Asn Leu Glu Lys Lys Leu Ser Tyr Leu Ser Ser
                1125                1130                1135

Gly Leu His His Leu Ile Ala Glu Leu Lys Lys Val Ile Lys Asn Lys
                1140                1145                1150

Asn Tyr Thr Gly Asn Ser Pro Ser Glu Asn Thr Asp Val Asn Asn
                1155                1160                1165

Ala Leu Glu Ser Tyr Lys Lys Phe Leu Pro Glu Gly Thr Asp Val Ala
                1170                1175                1180

Thr Val Val Ser Glu Ser Gly Ser Asp Thr Leu Glu Gln Ser Gln Pro
1185                1190                1195                1200

Lys Lys Pro Ala Ser Thr His Val Gly Ala Glu Ser Asn Thr Ile Thr
                1205                1210                1215

Thr Ser Gln Asn Val Asp Asp Glu Val Asp Asp Val Ile Ile Val Pro
                1220                1225                1230
```

-continued

```
Ile Phe Gly Glu Ser Glu Asp Tyr Asp Asp Leu Gly Gln Val Val
        1235                1240                1245

Thr Gly Glu Ala Val Thr Pro Ser Val Ile Asp Asn Ile Leu Ser Lys
1250                1255                1260

Ile Glu Asn Glu Tyr Glu Val Leu Tyr Leu Lys Pro Leu Ala Gly Val
1265                1270                1275                1280

Tyr Arg Ser Leu Lys Lys Gln Leu Glu Asn Asn Val Met Thr Phe Asn
        1285                1290                1295

Val Asn Val Lys Asp Ile Leu Asn Ser Arg Phe Asn Lys Arg Glu Asn
        1300                1305                1310

Phe Lys Asn Val Leu Glu Ser Asp Leu Ile Pro Tyr Lys Asp Leu Thr
        1315                1320                1325

Ser Ser Asn Tyr Val Val Lys Asp Pro Tyr Lys Phe Leu Asn Lys Glu
        1330                1335                1340

Lys Arg Asp Lys Phe Leu Ser Ser Tyr Asn Tyr Ile Lys Asp Ser Ile
1345                1350                1355                1360

Asp Thr Asp Ile Asn Phe Ala Asn Asp Val Leu Gly Tyr Tyr Lys Ile
        1365                1370                1375

Leu Ser Glu Lys Tyr Lys Ser Asp Leu Asp Ser Ile Lys Lys Tyr Ile
        1380                1385                1390

Asn Asp Lys Gln Gly Glu Asn Glu Lys Tyr Leu Pro Phe Leu Asn Asn
        1395                1400                1405

Ile Glu Thr Leu Tyr Lys Thr Val Asn Asp Lys Ile Asp Leu Phe Val
        1410                1415                1420

Ile His Leu Glu Ala Lys Val Leu Asn Tyr Thr Tyr Glu Lys Ser Asn
1425                1430                1435                1440

Val Glu Val Lys Ile Lys Glu Leu Asn Tyr Leu Lys Thr Ile Gln Asp
        1445                1450                1455

Lys Leu Ala Asp Phe Lys Lys Asn Asn Asn Phe Val Gly Ile Ala Asp
        1460                1465                1470

Leu Ser Thr Asp Tyr Asn His Asn Asn Leu Leu Thr Lys Phe Leu Ser
        1475                1480                1485

Thr Gly Met Val Phe Glu Asn Leu Ala Lys Thr Val Leu Ser Asn Leu
        1490                1495                1500

Leu Asp Gly Asn Leu Gln Gly Met Leu Asn Ile Ser Gln His Gln Cys
1505                1510                1515                1520

Val Lys Lys Gln Cys Pro Gln Asn Ser Gly Cys Phe Arg His Leu Asp
        1525                1530                1535

Glu Arg Glu Glu Cys Lys Cys Leu Leu Asn Tyr Lys Gln Glu Gly Asp
        1540                1545                1550

Lys Cys Val Glu Asn Pro Asn Pro Thr Cys Asn Glu Asn Asn Gly Gly
        1555                1560                1565

Cys Asp Ala Asp Ala Lys Cys Thr Glu Glu Asp Ser Gly Ser Asn Gly
        1570                1575                1580

Lys Lys Ile Thr Cys Glu Cys Thr Lys Pro Asp Ser Tyr Pro Leu Phe
1585                1590                1595                1600

Asp Gly Ile Phe Cys Ser Ser Ser Asn Phe Leu Gly Ile Ser Phe Leu
        1605                1610                1615

Leu Ile Leu Met Leu Ile Leu Tyr Ser Phe Ile
        1620                1625

<210> SEQ ID NO 44
<211> LENGTH: 358
```

<212> TYPE: PRT
<213> ORGANISM: Artificial Sequence
<220> FEATURE:
<223> OTHER INFORMATION: plasmodium falciparum Polypeptide fragment

<400> SEQUENCE: 44

```
Ala Val Thr Pro Ser Val Ile Asp Asn Ile Leu Ser Lys Ile Glu Asn
1               5                   10                  15

Glu Tyr Glu Val Leu Tyr Leu Lys Pro Leu Ala Gly Val Tyr Arg Ser
            20                  25                  30

Leu Lys Lys Gln Leu Glu Asn Asn Val Met Thr Phe Asn Val Asn Val
        35                  40                  45

Lys Asp Ile Leu Asn Ser Arg Phe Asn Lys Arg Glu Asn Phe Lys Asn
    50                  55                  60

Val Leu Glu Ser Asp Leu Ile Pro Tyr Lys Asp Leu Thr Ser Ser Asn
65                  70                  75                  80

Tyr Val Val Lys Asp Pro Tyr Lys Phe Leu Asn Lys Glu Lys Arg Asp
                85                  90                  95

Lys Phe Leu Ser Ser Tyr Asn Tyr Ile Lys Asp Ser Ile Asp Thr Asp
            100                 105                 110

Ile Asn Phe Ala Asn Asp Val Leu Gly Tyr Tyr Lys Ile Leu Ser Glu
        115                 120                 125

Lys Tyr Lys Ser Asp Leu Asp Ser Ile Lys Lys Tyr Ile Asn Asp Lys
    130                 135                 140

Gln Gly Glu Asn Glu Lys Tyr Leu Pro Phe Leu Asn Asn Ile Glu Thr
145                 150                 155                 160

Leu Tyr Lys Thr Val Asn Asp Lys Ile Asp Leu Phe Val Ile His Leu
                165                 170                 175

Glu Ala Lys Val Leu Asn Tyr Thr Tyr Glu Lys Ser Asn Val Glu Val
            180                 185                 190

Lys Ile Lys Glu Leu Asn Tyr Leu Lys Thr Ile Gln Asp Lys Leu Ala
        195                 200                 205

Asp Phe Lys Lys Asn Asn Asn Phe Val Gly Ile Ala Asp Leu Ser Thr
    210                 215                 220

Asp Tyr Asn His Asn Asn Leu Leu Thr Lys Phe Leu Ser Thr Gly Met
225                 230                 235                 240

Val Phe Glu Asn Leu Ala Lys Thr Val Leu Ser Asn Leu Leu Asp Gly
                245                 250                 255

Asn Leu Gln Gly Met Leu Asn Ile Ser Gln His Gln Cys Val Lys Lys
            260                 265                 270

Gln Cys Pro Gln Asn Ser Gly Cys Phe Arg His Leu Asp Glu Arg Glu
        275                 280                 285

Glu Cys Lys Cys Leu Leu Asn Tyr Lys Gln Glu Gly Asp Lys Cys Val
    290                 295                 300

Glu Asn Pro Asn Pro Thr Cys Asn Glu Asn Asn Gly Gly Cys Asp Ala
305                 310                 315                 320

Asp Ala Lys Cys Thr Glu Glu Asp Ser Gly Ser Asn Gly Lys Lys Ile
                325                 330                 335

Thr Cys Glu Cys Thr Lys Pro Asp Ser Tyr Pro Leu Phe Asp Gly Ile
            340                 345                 350

Phe Cys Ser Ser Ser Asn
            355
```

<210> SEQ ID NO 45
<211> LENGTH: 116

```
<212> TYPE: PRT
<213> ORGANISM: Artificial Sequence
<220> FEATURE:
<223> OTHER INFORMATION: plasmodium falciparum Polypeptide fragment

<400> SEQUENCE: 45

Met Leu Asn Ile Ser Gln His Gln Cys Val Lys Gln Cys Pro Glu
1               5                   10                  15

Asn Ser Gly Cys Phe Arg His Leu Asp Glu Arg Glu Glu Cys Lys Cys
            20                  25                  30

Leu Leu Asn Tyr Lys Gln Glu Gly Asp Lys Cys Val Glu Asn Pro Asn
        35                  40                  45

Pro Thr Cys Asn Glu Asn Asn Gly Gly Cys Asp Ala Asp Ala Thr Cys
    50                  55                  60

Thr Glu Glu Asp Ser Gly Ser Ser Arg Lys Lys Ile Thr Cys Glu Cys
65                  70                  75                  80

Thr Lys Pro Asp Ser Tyr Pro Leu Phe Asp Gly Ile Phe Cys Ser Ser
                85                  90                  95

Ser Asn Phe Leu Gly Ile Ser Phe Leu Ile Leu Met Leu Ile Leu
            100                 105                 110

Tyr Ser Phe Ile
        115

<210> SEQ ID NO 46
<211> LENGTH: 6
<212> TYPE: PRT
<213> ORGANISM: Artificial Sequence
<220> FEATURE:
<223> OTHER INFORMATION: synthetic Peptide linker

<400> SEQUENCE: 46

Gly Gly Ser Gly Gly Ser
1               5

<210> SEQ ID NO 47
<211> LENGTH: 5
<212> TYPE: PRT
<213> ORGANISM: Artificial Sequence
<220> FEATURE:
<223> OTHER INFORMATION: synthetic Peptide linker

<400> SEQUENCE: 47

Pro Ser Pro Ser Pro
1               5

<210> SEQ ID NO 48
<211> LENGTH: 5
<212> TYPE: PRT
<213> ORGANISM: Artificial Sequence
<220> FEATURE:
<223> OTHER INFORMATION: synthetic Peptide linker

<400> SEQUENCE: 48

Ala Ser Ala Ser Ala
1               5

<210> SEQ ID NO 49
<211> LENGTH: 5
<212> TYPE: PRT
<213> ORGANISM: Artificial Sequence
<220> FEATURE:
<223> OTHER INFORMATION: synthetic Peptide linker

<400> SEQUENCE: 49
```

Pro Ser Pro Ser Pro
1               5

<210> SEQ ID NO 50
<211> LENGTH: 4
<212> TYPE: PRT
<213> ORGANISM: Artificial Sequence
<220> FEATURE:
<223> OTHER INFORMATION: synthetic Peptide linker

<400> SEQUENCE: 50

Lys Lys Lys Lys
1

<210> SEQ ID NO 51
<211> LENGTH: 4
<212> TYPE: PRT
<213> ORGANISM: Artificial Sequence
<220> FEATURE:
<223> OTHER INFORMATION: synthetic Peptide linker

<400> SEQUENCE: 51

Arg Arg Arg Arg
1

<210> SEQ ID NO 52
<211> LENGTH: 4
<212> TYPE: PRT
<213> ORGANISM: Artificial Sequence
<220> FEATURE:
<223> OTHER INFORMATION: synthetic Peptide linker

<400> SEQUENCE: 52

Gly Gly Gly Gly
1

<210> SEQ ID NO 53
<211> LENGTH: 5
<212> TYPE: PRT
<213> ORGANISM: Artificial Sequence
<220> FEATURE:
<223> OTHER INFORMATION: synthetic Peptide linker

<400> SEQUENCE: 53

Gly Gly Gly Gly Ser
1               5

<210> SEQ ID NO 54
<211> LENGTH: 10
<212> TYPE: PRT
<213> ORGANISM: Artificial Sequence
<220> FEATURE:
<223> OTHER INFORMATION: synthetic peptide linker

<400> SEQUENCE: 54

Gly Gly Gly Gly Ser Gly Gly Gly Gly Ser
1               5                   10

<210> SEQ ID NO 55
<211> LENGTH: 20
<212> TYPE: PRT
<213> ORGANISM: Artificial Sequence
<220> FEATURE:
<223> OTHER INFORMATION: synthetic Peptide linker

<400> SEQUENCE: 55

```
<210> SEQ ID NO 56
<211> LENGTH: 25
<212> TYPE: PRT
<213> ORGANISM: Artificial Sequence
<220> FEATURE:
<223> OTHER INFORMATION: synthetic Peptide linker

<400> SEQUENCE: 56

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 57
<211> LENGTH: 30
<212> TYPE: PRT
<213> ORGANISM: Artificial Sequence
<220> FEATURE:
<223> OTHER INFORMATION: synthetic Peptide linker

<400> SEQUENCE: 57

Gly Gly Gly Gly Ser Gly Gly Gly Gly Ser Gly Gly Gly Gly Ser Gly
1               5                   10                  15

Gly Gly Gly Ser Gly Gly Gly Ser Gly Gly Gly Gly Ser
            20                  25                  30
```